(12) United States Patent
Bougueleret et al.

(10) Patent No.: US 6,582,909 B1
(45) Date of Patent: Jun. 24, 2003

(54) APM1 BIALLELIC MARKERS AND USES THEREOF

(75) Inventors: Lydie Bougueleret, Vanves (FR); Bernard Bihain, Encinitas, CA (US); Blake Denison, San Diego, CA (US); Frances Yen-Potin, San Diego, CA (US)

(73) Assignee: Genset, S.A. (FR)

( * ) Notice: Subject to any disclaimer, the term of this patent is extended or adjusted under 35 U.S.C. 154(b) by 0 days.

(21) Appl. No.: 09/569,852

(22) Filed: May 10, 2000

Related U.S. Application Data

(60) Provisional application No. 60/119,593, filed on Feb. 10, 1999, and provisional application No. 60/107,113, filed on Nov. 4, 1998.

(51) Int. Cl.[7] .............................. C12Q 1/68; C12P 19/34; C07H 21/04
(52) U.S. Cl. ........................ 435/6; 435/91.1; 435/91.2; 536/23.1
(58) Field of Search .................... 435/6, 91.1, 91.2; 536/23.1

(56) References Cited

U.S. PATENT DOCUMENTS

| | | |
|---|---|---|
| 5,270,170 A | 12/1993 | Schatz et al. |
| 5,869,330 A * | 2/1999 | Scherer et al. ............ 435/320.1 |

FOREIGN PATENT DOCUMENTS

| | | |
|---|---|---|
| WO | WO 96/30400 | 10/1996 |
| WO | WO 96/34981 | 11/1996 |
| WO | WO 96/39429 | 12/1996 |
| WO | WO 97/27286 | 7/1997 |
| WO | WO 98/02157 | 1/1998 |
| WO | WO 98/20165 | 5/1998 |
| WO | WO 54311 | 12/1998 |
| WO | WO 99/07736 | 2/1999 |
| WO | WO 99/10492 | 3/1999 |
| WO | WO 99/21577 | 6/1999 |

OTHER PUBLICATIONS

M Stumvoll et al., Diabetes, "Association of the T–G Polymorphism in Adiponectin (Exon 2) with Obesity and Insulin Sensitivity," Jan. 2002, vol. 51, 37–41.*
A Schäffler et al., European Journal of Clinical Investigation," Mutation analysis of the Human adipocyte–specific apM–1 gene," 2000, 30, 879–887.*
Alexeev and Yoon, "Stable and inheritable changes in genotype and phenotype of albino melanocytes induced by an RNA–DNA oligonucleotide," Nature Biotech., 16:1343–1346, 1998.
Arita, et al., "Paradoxical Decrease of an Adipose–Specific Protein, Adiponectin, in Obesity," Biochem. and Biophys. Research Comm. 257:79–83, 1999.
Austin, et al., "Hypertriglyceridemia as a Cardiovascular Risk Factor," Am. J. Cardiol., 81:7B–12B, 1998.

Baldo, et al., "The Adipsin–Acylation Stimulating Protein System and Regulation of Intracellular Triglyceride Synthesis,"J. Clin. Invest., 92:1543–1547 (1993).
Bartles, J.R., et al., "Biogenesis of the Rate Hepatocyte Plasma Membrane," Methods Enzymol., 191: 825–841, 1990.
Bihain, B.E., et al., "Characterization and purification of the lipolysis–stimulated receptor," Elsevier Science B.V., pp. 465–470, 1995.
Bihain, B.E., et al., "Free Fatty Acitds Activate a High–Affinity Saturable Pathway for Degradation of Low–Density Lipoproteins in Fibroblasts from a Subject Homozygous for Familial Hypercholesterolemia" Biochemistry, 31;4628–4636, 1992.
Brendel, V., et al., "Methods and algorithms for statistical analysis of protein sequences," Proc. Natl. Acad. Sci. USA, 89:2002–2006, 1992.
Chen, .W.J., et al., "NPXY, a Sequence Often Found in Cytoplasmic Tails, Is Required for Coated Pit–mediated Internalization of the Low Density Lipoprotein Receptor*", J. Biol. Chem., 265:3116–3123, 1990.
Cole–Strauss et al., "Correction of the Mutation Responsible for Sickle Cell Anemia by an RNA–DNA Oligonucleotide, "Science, 273:1386–1389, 1996.
Costet, P., et al., "Peroxisome Proliferator–activated Receptor α–Isoform Deficiency Leads to Progressive Dyslipidemia with Sexually Dimorphic Obesity and Steatosis*," J. Biol. Chem., 273, 29577–29585, 1998.
Davis, C.G., et al., "The J.D. Mutation in Familial Hypercholesterolemia: Amino Acid Substitution in Cytoplasmic Domain Impedes Internalization of LDL Receptors," Cell, 45:15–24, 1986.
Everhart J.E., "Weight Change and Obesity After Liver Transplantation: Incidence and Risk Factors," Liver Transpl. Surg., 4:285–296, 1998.
Feeman, Jr. W.E. "Hypertriglyceridemia and Atherosclerosis," Annals of Internal Medicine, vol. 128, No. 1, pp. 73–74, 1998.

(List continued on next page.)

Primary Examiner—W. Gary Jones
Assistant Examiner—Jehanne Souaya
(74) Attorney, Agent, or Firm—Saliwanchik, Lloyd & Saliwanchik

(57) ABSTRACT

The invention provides novel APM1 genomic sequences, polypeptides, antibodies, and polynucleotides including biallelic markers derived from the APM1 locus. Primers hybridizing to regions flanking these biallelic markers are also provided. This invention also provides polynucleotides and methods suitable for genotyping a nucleic acid containing sample for one or more biallelic markers of the invention. Additionally, the invention provides methods to detect a statistical correlation between a biallelic marker allele and a phenotype and/or between a biallelic marker haplotype and a phenotype. Further, the invention provides diagnostic methods for early detection of obesity-related disorders.

6 Claims, 8 Drawing Sheets

Ghebrehiwet, et al., "Isolation, cDNA Cloning, and Overexpression of a 33–kD Cell Surface Glycoprotein that Binds to the Globular "Heads"of C1q," *J. Exp. Med.*, 179:1809–1821 (1994).

Goldstein, J. L., et al., "Familial Hypercholesterolemia," *The Metabolic and Molecular Bases of Inherited Disease*, vol. II, 7th Edition (Scriver, C.R., et al., ed.). McGraw–Hill, New York, pp. 1981–2030, 1995.

Goldstein, et al., "Hyperlipidemia in Coronary Heart Disease," *J. Clin, Invest.*, 52:1533–1543, 1973.

Gura, et al., "Obesity Sheds Its Secrets", *Science*, 275:751–753, Feb. 7, 1997.

Hayward, et al., "The cDNA Sequence of Human Endothelial Cell Multimerin," *J. Biol. Chem.*, 270:18246–18251, 1995.

Henrion, et al., "Structure, Sequence, and Chromosomal Location of the Gene for USF2 Transcription Factors in Mouse," Genomics, 25:36–43 (1995).

Herz, J., et al., "Surface location and high affinity for calcium of a 500–kd liver membrane protein closely related to the LDL–receptor suggest a physiological role as lipoprotein receptor," European Molecular Biology Laboratory, 7:4119–4127 (1988).

Honoré, B. et al., "Cloning and expression of a cDNA covering the complete coding region of the P32 subunit of human pre–mRNA splicing factor SF2," *Gene*, 134:283–287 (1993).

Hu, et al., "AdipoQ is a Novel Adipose–specific Gene Dysregulated in Obesity," *J. Biol. Chem.*, 271:10697–10703 (1996).

Huettinger, M., et al., "Characteristics of Chylomicron Remnant Uptake into Rat Liver," *Clin. Biochem.*, 21:87–92 (1988).

Imagawa, et al., "Structure–Function Studies of Human Leptin," *J. Biol. Chem.*, 273:35245–35249, 1998.

Karpe, F., et al., "Clearance of lipoprotein remnant particles in adipose tissue and muscle in humans," *J. Lipid Res.* 38:2335–2343 (1997).

Karpe, F. et al., "Magnitude of alimentary lipemia is related to intima–media thickness of the common carotid artery in middle–aged men," *Elsevier Science Ireland*, 141:307–314, 1998.

Kersten, S., et al., "Peroxisome proliferator–activated receptor β mediates the adaptive response to fasting," *J. Clin. Invest.*, 103:1489–1498, Jun. 1999.

Khallou, et al., "Correction of Delayed Postprandial Plasma Lipid Response in Genetically Obese Mice by Injection Recombinant Leptin," Abstract from the 69th Scientific Sessions, New Orleans, LA; Supplemental to Circulation, American Heart Assoc., vol. 94:8 (1996).

Krainer, A. R., et al., "Functional Expression of Cloned Human Splicing Factor SF2: Homology to RNA–Binding Proteins, U1 70K, and Drosophila Splicing Regulators," *Cell*, 66:383–394, 1991.

Lee, M.G–S., et al., "Characterization of a cDNA Encoding a Cysteine–Rich Cell Surface Protein Located in the Flagellar Pocket of the Protozoan *Trypanosoma brucei*," *Molec. Cell. Biol.*, 10:4506–4517 (1990).

Letourneur, F., et al., "A Novel Di–Leucine Motif and a Tyrosine–Based Motif Independently Mediate Lysosomal Targeting and Endocytosis of CD3 Chains," *Cell*, 69:1143–1157 (1992).

Lewis, G.F., et al., "Postprandial Lipoprotein Metabolism in Normal and Obese Subjects: Comparison after the Vitamin A Fat–Loading Test," *Jr. of Clinic. Endo.*, 71:1041–1050, (1990).

Lin, et al., "Archaic Structure of the Gene Encoding Transcription Factor USF*," *Jr. of Bio. Chem.*, 268:23894–23903, (1994).

Lin, Q., et al., "Design of polydactyl zinc–finger proteins for unique addressing within complex genomes," *Proc. Natl. Acad. Sci. USA*, 94:5525–5530, 1997.

Maeda, et al., "cDNA Cloning and Expression of a Novel Adipose Specific Collagen–like Factor, apM1 (Adipose Most Abundant Gene Transcript 1)," *Biochem. and Biophys. Research Comm.*, 221:286–289, 1996.

Mahley, R.W., et al., "Type III Hyperlipoproteinemia (Dysbetalipoproteinemia): The Role of Apolipoprotein E in Normal and Abnormal Lipoprotein Metabolism," *The Molecular Basis of Inherited Disease*, eds. Scriver, et al., McGraw Hill Inc., New York, pp. 1953–1980, 1995.

Mann, C.J., et al., "Mechanism of Activation and Functional Significance of the Lipolysis–Stimulated Receptor. Evidence for a Role as Chylomicron Remnant Receptor", *Biochemistry*, 34:10421–10431 (1995).

Mann, et al., "ApoCIII Inhibits the Binding of Triglyceride–Rich Lipoproteins to the Lipolysis Stimulated Receptor," Abstract, (1996).

Massie, et al., "Inducible Overexpression of a Toxic Protein by an Adenovirus Vector with a Tetracycline–Regulatable Expression Cassette," *Journal of Virology*, 72:2289–2296, 1998.

Montague, et al., "Congenital leptin deficiency is associated with severe early–onset obesity in humans," *Nature*, 387:903–908, 1997.

Parra–Lopez, C.A., et al., "Presentation on Class II MHC Molecules of Endogenous Lysozyme Targeted to the Endocytic Pathway[1]" *J. Immunol.*, 158:2670–2679, 1997.

Pengue, G., et al., "Repression of transcriptional activity at a distance by the evolutionarily conserved KRAB domain present in a subfamily of zinc finger proteins," *Nucleic Acids Research*, vol. 22, No. 15, 2908–2914 (1994).

Perusse, L., et al., "The Human Obesity Gene Map: The 1998 Update," *Obes. Res.* 7:111–129, Jan. 1999.

Rajput–Williams, J., et al., "Variation of Apolipoprotein–B gene is associated with obesity, high blood cholesterol levels, and increased risk of coronary heart disease," The Lancet, pp. 1442–1446, 1998.

Rutherford, S., et al., "Association of a low density lipoprotein receptor micro–satellite variant with obesity," *Intl. Jr. of Obesity*, 21:1032–1037, 1997.

Saito, et al., "Organization of the gene for gelatin–binding protein (GBP28)," *GENE*, 229:67–73, Jan. 12, 1999.

Schäffler, et al., "Identification and characterization of the human adipocyte apM–1 promoter," *Biochem. and Biophys. Res. Comm.* 1399:187–197, 1998.

Schäffler, et al., "The Human apM–1, an Adipocyte–Specific Gene Linked to the Family of TFN's and to Genes Expressed in Activated T Cells, is Mapped to Chromosome 1q21.3–q23, a Susceptibility Locus Identified for Familial Combined Hyperlipidaemia (FCH), " *Biochem. and Biophys. Res. Comm.* 260:416–425, May 7, 1999.

Scherer, et al., "A Novel Serum Protein Simular to C1q, Produced Excusively in Adipocytes*," *J. Biol. Chem.*, 270:26746–26749, 1995.

Sellar, et al., "Characterization and organization of the genes encoding the A–, B–and C–chains of human complement subcomponent C1q," Biochemical Journal, 274:481–490, (1991).

Shimabukuro, M., et al., "Direct antidiabetic effect of leptin through triglyceride depletion of tissues," Proc. Natl. Acad. Sci. USA, 94:4637–4641, 1997.

Shimano, H., et al., "Overproduction of Cholesterol and Fatty Acids Causes Massive–Liver Enlargement in Transgenic Mice Expressing Truncated SREBP–1a," J. Clin. Invest., 98:1575–1584, 1996.

Shimomura, et al., "Leptin reverses insulin resistance and diabetes mellitus in mice with congenital lipodystrophy," Nature, 401:73–76, Sep. 2, 1999.

Shin, J., et al., "Phosphorylation–dependent Down–modulation of CD4 Requires a Specific Structure within the Cytoplasmic Domain of CD4," Jr. of Biol. Chem., vol. 266:10658–10665, 1991.

Simos, G. et al., "The lamin B receptor–associated protein p34 shares sequence homology and antigenic determinants with the splicing factor 2–associated protein p32," FEBS Letters 346:225–228, 1994.

Steingrimsson, E., et al., "Murine Chromosomal Location of Five bHLH–Zip Transcription Factor Genes," Genomics, 28:179–183, 1995.

Troussard, A.A., et al., "Inhibitory Effect on the Lipolysis–stimulated Receptor of the 39–kDa Receptor–associated Protein*," Jr. of Biol. Chem., 270:17068–71, 1995.

Urade, Y., et al., "Precerebellin is a cerebellum–specific protein with similarity to the globular domain of complement C1q B chain," Proc. Natl. Sci. USA, 88:1069–1073, 1991.

Uotani, S. "Functional Properties of Leptin Receptor Isoforms Internalization and Degradation of Leptin and Ligand–Induced Receptor Downregulation Diabetes," 48:279–286, Feb. 1999.

Vansant, G., et al., "Determinants of postprandial lipemia in obese women," Intl. Jr. of Obesity, 23:Supp. 1, 14–21, 1999.

Verhey, K.J., et al., "A Leu–Leu Sequence is Essential for COOH–terminal Targeting Signal of GLUT4 Glucose Transporter in Fibroblasts," J. Biol. Chem., 269:2353–2356, 1994.

Wang, et al., "Upstream Stimulatory Factor Binding to the E–box at –65 is required for Insulin Regulation of the Fatty Acid Synthase Promoter," J. Biol. Chem., 272:26367–26374, 1997.

Yen, et al., "Molecular Cloning of a Lipolysis–stimulated Remnant Receptor Expressed in the Liver,"J. Biol. Chem., 274:13390–13398, 1999.

Yen, F.T., et al., "Identification of a Lipolysis–Stimulated Receptor That is Distinct from the LDL Receptor and the LDL Receptor–Related Protein," Biochemistry, 33:1172–1180, 1994.

Zhang, M. et al., "Tumor Necrosis Factor," The Cytokine Handbook, Third Ed., pp. 517–548, 1998.

Zhong, G. et al., "Related Leucine–based Cytoplasmic Targeting Signals in Invariant Chain and Major Histocompatibility Complex Class II Molecules Control Endocytic Presentation of Distinct Determinants in a Single Protein," J. Exp. Med., 185:429–438, 1997.

* cited by examiner

FIGURE 3
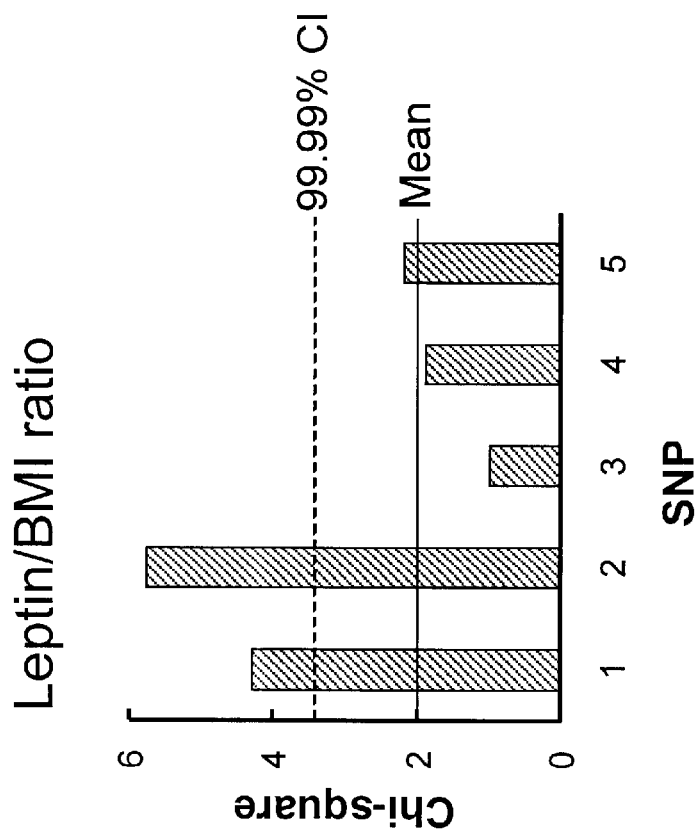
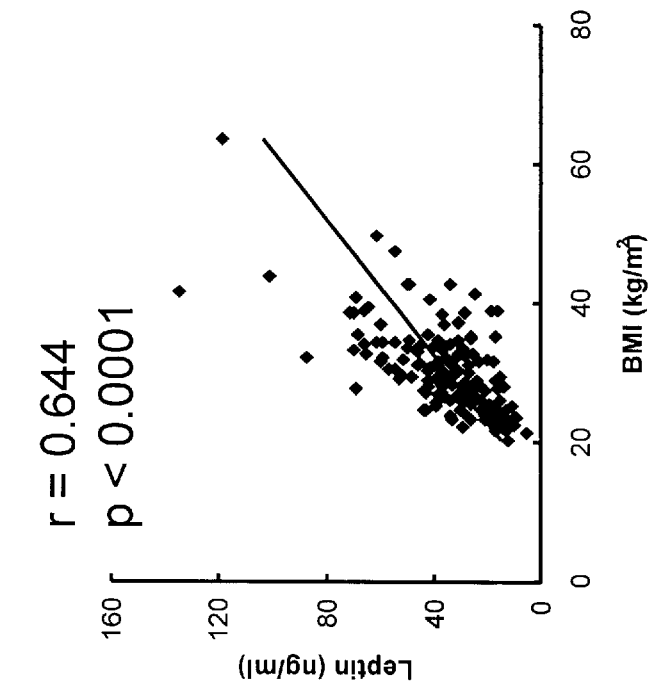

FIGURE 4
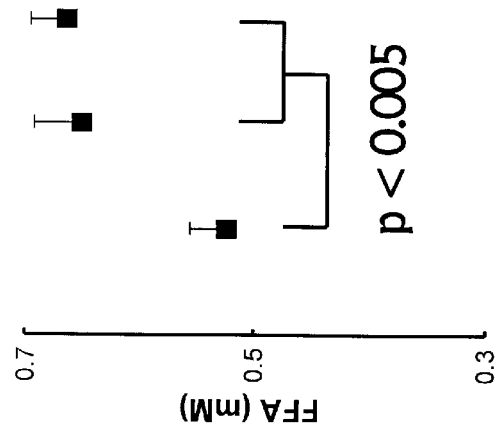
A  Marker #4
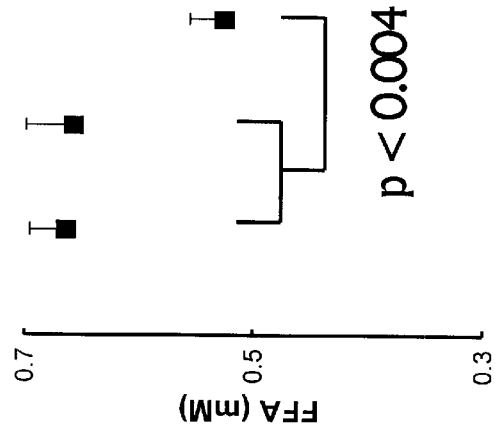
B  Marker #5

SEQUENCE LISTING

<160> NUMBER OF SEQ ID NOS: 8

<210> SEQ ID NO 1
<211> LENGTH: 20966
<212> TYPE: DNA
<213> ORGANISM: Homo sapiens
<220> FEATURE:
<221> NAME/KEY: misc_feature
<222> LOCATION: (1)..(4811)
<223> OTHER INFORMATION: 5' regulatory region
<221> NAME/KEY: primer_bind
<222> LOCATION: (14683)..(14701)
<223> OTHER INFORMATION: 17-34-860.mis
<221> NAME/KEY: primer_bind
<222> LOCATION: (14703)..(14721)
<223> OTHER INFORMATION: 17-34-860.mis complement
<221> NAME/KEY: primer_bind
<222> LOCATION: (14738)..(14756)
<223> OTHER INFORMATION: 17-34-915.mis
<221> NAME/KEY: primer_bind
<222> LOCATION: (14758)..(14776)
<223> OTHER INFORMATION: 17-34-915.mis complement
<221> NAME/KEY: primer_bind
<222> LOCATION: (14796)..(14814)
<223> OTHER INFORMATION: 17-35-71.mis
<221> NAME/KEY: primer_bind
<222> LOCATION: (14816)..(14834)
<223> OTHER INFORMATION: 17-35-71.mis complement
<221> NAME/KEY: primer_bind
<222> LOCATION: (15031)..(15049)
<223> OTHER INFORMATION: 17-35-306.mis
<221> NAME/KEY: primer_bind
<222> LOCATION: (15051)..(15069)
<223> OTHER INFORMATION: 17-35-306.mis complement
<221> NAME/KEY: primer_bind
<222> LOCATION: (15101)..(15119)
<223> OTHER INFORMATION: 9-12-48.mis
<221> NAME/KEY: primer_bind
<222> LOCATION: (15121)..(15139)
<223> OTHER INFORMATION: 9-12-48.mis complement
<221> NAME/KEY: primer_bind
<222> LOCATION: (15177)..(15195)
<223> OTHER INFORMATION: 9-12-124.mis
<221> NAME/KEY: primer_bind
<222> LOCATION: (15197)..(15215)
<223> OTHER INFORMATION: 9-12-124.mis complement
<221> NAME/KEY: primer_bind
<222> LOCATION: (15408)..(15426)
<223> OTHER INFORMATION: 9-12-355.mis
<221> NAME/KEY: primer_bind
<222> LOCATION: (15428)..(15446)
<223> OTHER INFORMATION: 9-12-355.mis complement
<221> NAME/KEY: primer_bind
<222> LOCATION: (15481)..(15499)
<223> OTHER INFORMATION: 9-12-428.mis
<221> NAME/KEY: primer_bind
<222> LOCATION: (15501)..(15519)
<223> OTHER INFORMATION: 9-12-428.mis complement
<221> NAME/KEY: primer_bind
<222> LOCATION: (15661)..(15679)
<223> OTHER INFORMATION: 17-36-47.mis
<221> NAME/KEY: primer_bind
<222> LOCATION: (15681)..(15699)
<223> OTHER INFORMATION: 17-36-47.mis complement
<221> NAME/KEY: primer_bind
<222> LOCATION: (15771)..(15789)
<223> OTHER INFORMATION: 17-36-120.mis
<221> NAME/KEY: primer_bind
<222> LOCATION: (15791)..(15809)
<223> OTHER INFORMATION: 17-36-120.mis complement
<221> NAME/KEY: primer_bind
<222> LOCATION: (15844)..(15862)
<223> OTHER INFORMATION: 99-14405-105.mis
<221> NAME/KEY: primer_bind
<222> LOCATION: (15864)..(15882)
<223> OTHER INFORMATION: 99-14405-105.mis complement -continued

```
<221> NAME/KEY: primer_bind
<222> LOCATION: (17151)..(17169)
<223> OTHER INFORMATION: 9-16-189.mis
<221> NAME/KEY: primer_bind
<222> LOCATION: (17171)..(17189)
<223> OTHER INFORMATION: 9-16-189.mis complement
<221> NAME/KEY: primer_bind
<222> LOCATION: (17810)..(17828)
<223> OTHER INFORMATION: 17-37-629.mis
<221> NAME/KEY: primer_bind
<222> LOCATION: (17830)..(17848)
<223> OTHER INFORMATION: 17-37-629.mis complement
<221> NAME/KEY: primer_bind
<222> LOCATION: (17992)..(18010)
<223> OTHER INFORMATION: 17-37-811.mis
<221> NAME/KEY: primer_bind
<222> LOCATION: (18012)..(18030)
<223> OTHER INFORMATION: 17-37-811.mis complement
<221> NAME/KEY: primer_bind
<222> LOCATION: (18470)..(18488)
<223> OTHER INFORMATION: 17-38-349.mis
<221> NAME/KEY: primer_bind
<222> LOCATION: (18490)..(18508)
<223> OTHER INFORMATION: 17-38-349.mis complement
<221> NAME/KEY: primer_bind
<222> LOCATION: (926)..(944)
<223> OTHER INFORMATION: 17-30-216.mis
<221> NAME/KEY: primer_bind
<222> LOCATION: (946)..(964)
<223> OTHER INFORMATION: 17-30-216.mis complement
<221> NAME/KEY: primer_bind
<222> LOCATION: (3719)..(3737)
<223> OTHER INFORMATION: 9-27-211.mis
<221> NAME/KEY: primer_bind
<222> LOCATION: (3739)..(3757)
<223> OTHER INFORMATION: 9-27-211.mis complement
<221> NAME/KEY: primer_bind
<222> LOCATION: (3754)..(3772)
<223> OTHER INFORMATION: 9-27-246.mis
<221> NAME/KEY: primer_bind
<222> LOCATION: (3774)..(3792)
<223> OTHER INFORMATION: 9-27-246.mis complement
<221> NAME/KEY: primer_bind
<222> LOCATION: (3768)..(3786)
<223> OTHER INFORMATION: 9-27-261.mis
<221> NAME/KEY: primer_bind
<222> LOCATION: (3788)..(3806)
<223> OTHER INFORMATION: 9-27-261.mis complement
<221> NAME/KEY: primer_bind
<222> LOCATION: (5076)..(5094)
<223> OTHER INFORMATION: 17-31-298.mis
<221> NAME/KEY: primer_bind
<222> LOCATION: (5096)..(5114)
<223> OTHER INFORMATION: 17-31-298.mis complement
<221> NAME/KEY: primer_bind
<222> LOCATION: (5191)..(5209)
<223> OTHER INFORMATION: 17-31-413.mis
<221> NAME/KEY: primer_bind
<222> LOCATION: (5211)..(5229)
<223> OTHER INFORMATION: 17-31-413.mis complement
<221> NAME/KEY: primer_bind
<222> LOCATION: (5364)..(5385)
<223> OTHER INFORMATION: 17-31.rp complement
<221> NAME/KEY: primer_bind
<222> LOCATION: (10618)..(10636)
<223> OTHER INFORMATION: 17-32-24.mis
<221> NAME/KEY: primer_bind
<222> LOCATION: (10638)..(10656)
<223> OTHER INFORMATION: 17-32-24.mis complement
<221> NAME/KEY: primer_bind
<222> LOCATION: (11020)..(11038)
<223> OTHER INFORMATION: 99-14387-50.mis
<221> NAME/KEY: primer_bind
<222> LOCATION: (11040)..(11058)
<223> OTHER INFORMATION: 99-14387-50.mis complement
<221> NAME/KEY: primer_bind
<222> LOCATION: (11099)..(11117)
<223> OTHER INFORMATION: 99-14387-129.mis
<221> NAME/KEY: primer_bind
```

```
<222> LOCATION: (11119)..(11137)
<223> OTHER INFORMATION: 99-14387-129.mis complement
<221> NAME/KEY: primer_bind
<222> LOCATION: (11169)..(11187)
<223> OTHER INFORMATION: 99-14387-199.mis
<221> NAME/KEY: primer_bind
<222> LOCATION: (11189)..(11207)
<223> OTHER INFORMATION: 99-14387-199.mis complement
<221> NAME/KEY: primer_bind
<222> LOCATION: (13954)..(13972)
<223> OTHER INFORMATION: 17-33-TGAGACT.mis
<221> NAME/KEY: primer_bind
<222> LOCATION: (13974)..(13992)
<223> OTHER INFORMATION: 17-33-TGAGACT.mis complement
<221> NAME/KEY: exon
<222> LOCATION: (4812)..(4851)
<223> OTHER INFORMATION:
<221> NAME/KEY: exon
<222> LOCATION: (15144)..(15365)
<223> OTHER INFORMATION:
<221> NAME/KEY: exon
<222> LOCATION: (16277)..(20559)
<223> OTHER INFORMATION:
<221> NAME/KEY: misc_feature
<222> LOCATION: (20560)..(20966)
<223> OTHER INFORMATION: 3' regulatory region
<221> NAME/KEY: misc_feature
<222> LOCATION: (15194)..(15196)
<223> OTHER INFORMATION: Amino acid at position 31 (Xaa) means Gly
<221> NAME/KEY: misc_feature
<222> LOCATION: (31)..(31)
<223> OTHER INFORMATION: The 'Xaa' at location 31 stands for Gly.
<221> NAME/KEY: misc_feature
<222> LOCATION: (18010)..(18012)
<223> OTHER INFORMATION: Amino acid at position 647 (Xaa) means Arg or
      His
<221> NAME/KEY: misc_feature
<222> LOCATION: (647)..(647)
<223> OTHER INFORMATION: The 'Xaa' at location 647 stands for Arg or
      His.
<221> NAME/KEY: allele
<222> LOCATION: (945)..(945)
<223> OTHER INFORMATION: 17-30-216 : polymorphic base A or G
<221> NAME/KEY: allele
<222> LOCATION: (3738)..(3738)
<223> OTHER INFORMATION: 9-27-211 : polymorphic base A or G
<221> NAME/KEY: allele
<222> LOCATION: (3773)..(3773)
<223> OTHER INFORMATION: 9-27-246 : polymorphic base A or G
<221> NAME/KEY: allele
<222> LOCATION: (3787)..(3787)
<223> OTHER INFORMATION: 9-27-261 : polymorphic base G or C
<221> NAME/KEY: allele
<222> LOCATION: (5095)..(5095)
<223> OTHER INFORMATION: 17-31-298 : polymorphic base A or G
<221> NAME/KEY: allele
<222> LOCATION: (5210)..(5210)
<223> OTHER INFORMATION: 17-31-413 : polymorphic base C or T
<221> NAME/KEY: allele
<222> LOCATION: (10637)..(10637)
<223> OTHER INFORMATION: 17-32-24 : polymorphic base C or T
<221> NAME/KEY: allele
<222> LOCATION: (11039)..(11039)
<223> OTHER INFORMATION: 99-14387-50 : polymorphic base A or C
<221> NAME/KEY: allele
<222> LOCATION: (11118)..(11118)
<223> OTHER INFORMATION: 99-14387-129 : polymorphic base A or C
<221> NAME/KEY: allele
<222> LOCATION: (11188)..(11188)
<223> OTHER INFORMATION: 99-14387-199 : polymorphic base A or G
<221> NAME/KEY: allele
<222> LOCATION: (13973)..(13973)
<223> OTHER INFORMATION: 17-33-TGAGACT : polymorphic base insertion of
      TGAGACT
<221> NAME/KEY: allele
<222> LOCATION: (14702)..(14702)
<223> OTHER INFORMATION: 17-34-860 : polymorphic base A or G
<221> NAME/KEY: allele
<222> LOCATION: (14757)..(14757)
```

-continued

```
<223> OTHER INFORMATION: 17-34-915 : polymorphic base A or G
<221> NAME/KEY: allele
<222> LOCATION: (14815)..(14815)
<223> OTHER INFORMATION: 17-35-71 : polymorphic base C or T
<221> NAME/KEY: allele
<222> LOCATION: (15050)..(15050)
<223> OTHER INFORMATION: 17-35-306 : polymorphic base G or T
<221> NAME/KEY: allele
<222> LOCATION: (15120)..(15120)
<223> OTHER INFORMATION: 9-12-48 : polymorphic base C or T
<221> NAME/KEY: allele
<222> LOCATION: (15196)..(15196)
<223> OTHER INFORMATION: 9-12-124 : polymorphic base G or T
<221> NAME/KEY: allele
<222> LOCATION: (15427)..(15427)
<223> OTHER INFORMATION: 9-12-355 : polymorphic base G or T
<221> NAME/KEY: allele
<222> LOCATION: (15500)..(15500)
<223> OTHER INFORMATION: 9-12-428 : polymorphic base A or G
<221> NAME/KEY: allele
<222> LOCATION: (15680)..(15680)
<223> OTHER INFORMATION: 17-36-47 : polymorphic base G or C
<221> NAME/KEY: allele
<222> LOCATION: (15790)..(15790)
<223> OTHER INFORMATION: 17-36-120 : polymorphic base C or T
<221> NAME/KEY: allele
<222> LOCATION: (15863)..(15863)
<223> OTHER INFORMATION: 99-14405-105 : polymorphic base A or G
<221> NAME/KEY: allele
<222> LOCATION: (17170)..(17170)
<223> OTHER INFORMATION: 9-16-189 : polymorphic base deletion of A
<221> NAME/KEY: allele
<222> LOCATION: (17829)..(17829)
<223> OTHER INFORMATION: 17-37-629 : polymorphic base A or G
<221> NAME/KEY: allele
<222> LOCATION: (18011)..(18011)
<223> OTHER INFORMATION: 17-37-811 : polymorphic base A or G
<221> NAME/KEY: allele
<222> LOCATION: (18489)..(18489)
<223> OTHER INFORMATION: 17-38-349 : polymorphic base C or T
<221> NAME/KEY: primer_bind
<222> LOCATION: (730)..(752)
<223> OTHER INFORMATION: 17-30.pu
<221> NAME/KEY: primer_bind
<222> LOCATION: (1117)..(1137)
<223> OTHER INFORMATION: 17-30.rp complement
<221> NAME/KEY: primer_bind
<222> LOCATION: (3528)..(3545)
<223> OTHER INFORMATION: 9-27.pu
<221> NAME/KEY: primer_bind
<222> LOCATION: (3928)..(3946)
<223> OTHER INFORMATION: 9-27.rp complement
<221> NAME/KEY: primer_bind
<222> LOCATION: (4798)..(4819)
<223> OTHER INFORMATION: 17-31.pu
<221> NAME/KEY: primer_bind
<222> LOCATION: (10614)..(10635)
<223> OTHER INFORMATION: 17-32.pu
<221> NAME/KEY: primer_bind
<222> LOCATION: (10990)..(11008)
<223> OTHER INFORMATION: 99-14387.pu
<221> NAME/KEY: primer_bind
<222> LOCATION: (11093)..(11114)
<223> OTHER INFORMATION: 17-32.rp complement
<221> NAME/KEY: primer_bind
<222> LOCATION: (11423)..(11442)
<223> OTHER INFORMATION: 99-14387.rp complement
<221> NAME/KEY: primer_bind
<222> LOCATION: (13843)..(13865)
<223> OTHER INFORMATION: 17-33.pu
<221> NAME/KEY: primer_bind
<222> LOCATION: (13843)..(13865)
<223> OTHER INFORMATION: 17-34.pu
<221> NAME/KEY: primer_bind
<222> LOCATION: (14496)..(14517)
<223> OTHER INFORMATION: 17-33.rp complement
<221> NAME/KEY: primer_bind
<222> LOCATION: (14745)..(14766)
<223> OTHER INFORMATION: 17-35.pu
```

```
<221> NAME/KEY: primer_bind
<222> LOCATION: (14839)..(14859)
<223> OTHER INFORMATION: 17-34.rp complement
<221> NAME/KEY: primer_bind
<222> LOCATION: (15073)..(15092)
<223> OTHER INFORMATION: 9-12.pu
<221> NAME/KEY: primer_bind
<222> LOCATION: (15199)..(15219)
<223> OTHER INFORMATION: 17-35.rp complement
<221> NAME/KEY: primer_bind
<222> LOCATION: (15381)..(15402)
<223> OTHER INFORMATION: 17-36.pu
<221> NAME/KEY: primer_bind
<222> LOCATION: (15503)..(15520)
<223> OTHER INFORMATION: 9-12.rp complement
<221> NAME/KEY: primer_bind
<222> LOCATION: (15759)..(15776)
<223> OTHER INFORMATION: 99-14405.pu
<221> NAME/KEY: primer_bind
<222> LOCATION: (15966)..(15987)
<223> OTHER INFORMATION: 17-36.rp complement
<221> NAME/KEY: primer_bind
<222> LOCATION: (16191)..(16211)
<223> OTHER INFORMATION: 99-14405.rp complement
<221> NAME/KEY: primer_bind
<222> LOCATION: (16982)..(17001)
<223> OTHER INFORMATION: 9-16.pu
<221> NAME/KEY: primer_bind
<222> LOCATION: (17201)..(17222)
<223> OTHER INFORMATION: 17-37.pu
<221> NAME/KEY: primer_bind
<222> LOCATION: (17384)..(17402)
<223> OTHER INFORMATION: 9-16.rp complement
<221> NAME/KEY: primer_bind
<222> LOCATION: (18141)..(18163)
<223> OTHER INFORMATION: 17-38.pu
<221> NAME/KEY: primer_bind
<222> LOCATION: (18240)..(18261)
<223> OTHER INFORMATION: 17-37.rp complement
<221> NAME/KEY: primer_bind
<222> LOCATION: (19314)..(19336)
<223> OTHER INFORMATION: 17-38.rp complement
<221> NAME/KEY: misc_binding
<222> LOCATION: (933)..(957)
<223> OTHER INFORMATION: 17-30-216.probe
<221> NAME/KEY: misc_binding
<222> LOCATION: (3726)..(3750)
<223> OTHER INFORMATION: 9-27-211.probe
<221> NAME/KEY: misc_binding
<222> LOCATION: (3761)..(3785)
<223> OTHER INFORMATION: 9-27-246.probe
<221> NAME/KEY: misc_binding
<222> LOCATION: (3775)..(3799)
<223> OTHER INFORMATION: 9-27-261.probe
<221> NAME/KEY: misc_binding
<222> LOCATION: (5083)..(5107)
<223> OTHER INFORMATION: 17-31-298.probe
<221> NAME/KEY: misc_binding
<222> LOCATION: (5198)..(5222)
<223> OTHER INFORMATION: 17-31-413.probe
<221> NAME/KEY: misc_binding
<222> LOCATION: (10625)..(10649)
<223> OTHER INFORMATION: 17-32-24.probe
<221> NAME/KEY: misc_binding
<222> LOCATION: (11027)..(11051)
<223> OTHER INFORMATION: 99-14387-50.probe
<221> NAME/KEY: misc_binding
<222> LOCATION: (11106)..(11130)
<223> OTHER INFORMATION: 99-14387-129.probe
<221> NAME/KEY: misc_binding
<222> LOCATION: (11176)..(11200)
<223> OTHER INFORMATION: 99-14387-199.probe
<221> NAME/KEY: misc_binding
<222> LOCATION: (13961)..(13985)
<223> OTHER INFORMATION: 17-33-TGAGACT.probe
<221> NAME/KEY: misc_binding
<222> LOCATION: (14690)..(14714)
<223> OTHER INFORMATION: 17-34-860.probe
<221> NAME/KEY: misc_binding
```

```
<222> LOCATION: (14745)..(14769)
<223> OTHER INFORMATION: 17-34-915.probe
<221> NAME/KEY: misc_binding
<222> LOCATION: (14803)..(14827)
<223> OTHER INFORMATION: 17-35-71.probe
<221> NAME/KEY: misc_binding
<222> LOCATION: (15038)..(15062)
<223> OTHER INFORMATION: 17-35-306.probe
<221> NAME/KEY: misc_binding
<222> LOCATION: (15108)..(15132)
<223> OTHER INFORMATION: 9-12-48.probe
<221> NAME/KEY: misc_binding
<222> LOCATION: (15184)..(15208)
<223> OTHER INFORMATION: 9-12-124.probe
<221> NAME/KEY: misc_binding
<222> LOCATION: (15415)..(15439)
<223> OTHER INFORMATION: 9-12-355.probe
<221> NAME/KEY: misc_binding
<222> LOCATION: (15488)..(15512)
<223> OTHER INFORMATION: 9-12-428.probe
<221> NAME/KEY: misc_binding
<222> LOCATION: (15668)..(15692)
<223> OTHER INFORMATION: 17-36-47.probe
<221> NAME/KEY: misc_binding
<222> LOCATION: (15778)..(15802)
<223> OTHER INFORMATION: 17-36-120.probe
<221> NAME/KEY: misc_binding
<222> LOCATION: (15851)..(15875)
<223> OTHER INFORMATION: 99-14405-105.probe
<221> NAME/KEY: misc_binding
<222> LOCATION: (17158)..(17182)
<223> OTHER INFORMATION: 9-16-189.probe
<221> NAME/KEY: misc_binding
<222> LOCATION: (17817)..(17841)
<223> OTHER INFORMATION: 17-37-629.probe
<221> NAME/KEY: misc_binding
<222> LOCATION: (17999)..(18023)
<223> OTHER INFORMATION: 17-37-811.probe
<221> NAME/KEY: misc_binding
<222> LOCATION: (18477)..(18501)
<223> OTHER INFORMATION: 17-38-349.probe

<400> SEQUENCE: 1
gctgatctgc tgcctcagcc ttcccaaagt gctgtaattt attaggcata agccactgtg      60
cctgcctagt gttgtacatt ctgtgggttt tgacaattgt atgcatctac atgtatgtac     120
catttatagt attcctgttt ttaatttttag ccattctagt aggcatgtag tgatatctca     180
tggtgatttt aatttgcgtt tccgtaatgg ttaataatgc tgaacatctt tgcatgtgct     240
tgtttgtcat ttgtgtttcc tacttggtga ataattgtt catgtccttt gtccattttc      300
taattgaatt ttttttttacc atttagtttt gagatttctt tatacaatct agatccaaat     360
ctcttgtctc aaatatggtt tgcaaataca ttcctctaat tcatatattg ccttttcctc     420
ctcttaacag gatgtttcac agagcaaaag tttttagtttt gttgaaatct cacttttcat     480
ttttttcttt agtggattgt gcttttgttg tcatatgtaa gaactcttca ctggccctag     540
atccttgtat tggtttccta agattgccat agcaaatcac catgaactta gtgacaaaaa     600
gacagaaatt tattttcact tcctactgtg ggcagactag acgttaatta ttttcatgta     660
tgctcattcc tatgacatct ttctgatata ataattatag ttattcttaa gcttcaccct     720
tttttctatt agctttgtta ccttgggtgt cacttttttct tttttgacat tgtgacctat     780
gccagatcat gtctgttagt acttagccct ccattcacct ctccataatc ccttttgtat     840
tcctggagct tgatgcctga aatgacacat cctacattcc tttgccagat gggtaccagt     900
tagcttgtgc acatgggaga caaccgtgaa aagactgaag tgggraagaa gggaggagct     960
gttgtgtttc agtgagcgcc cttggcagtg gcggtgacag tggctcctgt tcagtggcaa    1020
tggtggagca gctagcaaga catgcagtaa gcgcaggctc ataggctatg gtccaggagc    1080
```

-continued

```
agtcaccgat tcctggtctt taggcaatat catctccctt tgcttctcca gcctttctaa    1140
aattattgta ccttgactag tacaattttt tagtattggg ggtagtccaa ggacacaggc    1200
tttaaaaagt atgaattcag ggttgcctac ctgcattgac tgcgcttgaa tcatgatggc    1260
cttctggtcg gtggcaggag gtgacagtcc aaatcatgca gtagcaaacc agatacttaa    1320
attatcatct gagatacttc agaagtacag ccgtagccat accttcagaa gagataaaga    1380
aatgttctcc tggccaggcg cggtggctca cgcctgtcat tccagcactt gggaggccg     1440 aggggtgga tcacctgagg tcgggagttc gagaccagcc tgaccaacat ggggaaaccc     1500
tgtctctact aaaaatacaa aattagcggg gcgtggtggc acatgcccat aatcccagct    1560
actcgggagg ctaaggcagg ataatcgctt gaacctgaga ggcagaggtt gcggtgaact    1620
gagatcatgc catagtactc cagcctgggc aacaagagtg aaactccatc tcaaaaaaaa    1680 aaaaagaaa aaaagataaa gaaatgttct cctttcttgc catttctagg ggtttgggga    1740
tggcgtacat tgctgcaggg cgtgctcact ctaccatctt gctccaatct ttattttca    1800 aaatacagtg cttatgcttg gttacttcag ttaagattat ttttaaaaat cataattaag    1860
caaaaatata tggccatgct taaacatatt taagataaat taagtgattt ggcctgtttc    1920
agtatcccaa ctcacatgct aacagggggct tgacctgtag ctacggtacc ctggaggaaa    1980
tgatcgcatt tatttggtta tttcggtcta agtagtaata gttctgtcct gggaaaaga    2040 ctagcctcaa ggcatttctg attgaatgtt tttcaattac agtctttaaa ccagtatgcc    2100
acagaactgg ctcttccac atgacggcct ttgtggtggg tggcagattg ccctgaggcc     2160
tcgcaaaatg ctaggctttc acaatgtcac tgactgacag ccaggcccag cacagtcttg    2220
gtgtgattgt ggggctaaag ttattccacc ttgtgcaata gctacagcct tctctaacca    2280
gctgcattct tataaagtta gaagaaaata cttttttttt tttgagatgg attctcgctc    2340
tgttgcccag gctggagtgc aatggtgcga tctcggctcg ctgcaacctc cgcctcctgg    2400
gttcaaacga ttctcctccc tcagaccccc gagtagctgg gattgcaggt gcctgccacc    2460
acgcccggct aactttttg tattttagt ggagacgggg tttcaccatc ttcgtcaggc      2520
tggtctcaga ctcctgacct caagtgatct gcccgcctca gcctcccaaa atgctgggat    2580
tacaggcatg agctactgtg cccggccaaa gaaaatactt tttatgccag ccctgaaact    2640
accctgaagc acatacatca accttgaggc ctcacactcc atcaagaggg gtgaagggca    2700
tgaggaatta gaaagcatag ggattttag ttagacagat ctggttcaaa tcctagactt     2760
gtgccttgaa caaattattt accctcattg aactctagat tcattatttg taaaatgaaa    2820
gacaataata gttatctcca aaggaaagtt gaatatgatc attcatttat tcattaattc    2880
aacatttatt attgcctact ttgtgccagg ttctattcta ggaactaagg gatacaactt    2940
tgaataggca aaatctctgc tctcctgaag tttacttttt tttttttttt ttgagacaga    3000
gtttcactct tgtcacccag gctggagcgc aatggtgctc ttggctcact gcaacctcca    3060
cctcctgggt tcaagtgatt ctcttgtctc agcctcccaa gtagctggga ctacaggtat    3120
gtgccaccac gcccggctat ttctgcattt ttagtagaga tggggtttca ccatgttggc    3180
cagactggtc tcaaactcct gatctcaggt gatatgcctg tcttggcctt ccaaagtact    3240
gggattacag gcctgagcca ctgcacctga cctgaagttt atgttctatt aaatagcaac    3300
agacagtaac ataaaccaaa aataaatagg aaaacaccat aacaaaaatc aaacagtgat    3360
ataattgaga gttgcttcta tttcttttg ttgtcttctt ggttcaatca gcctgctaaa     3420
```

```
ctatatggaa cctcatttc atgggccact tatttaagcc gggggacctt ggaaagtctc  3480
tcatgtctct catctcaacg gcctaatgtg acttctcttg aaatatttgg acattagcag  3540
gaagctgagg ctttacatca gatctttact ttaatggtgg acttgacttt actggtagat  3600
ttttaggctc tgtgtggact gtggagatga tatctggggg gcaggcagac acttgccctg  3660
cctctgtctg agaaaattct gttttggatg tcttgttgaa gttggtgctg gcatcctaag  3720
cccttgctgg ggtcgtartt taattcatca gaatgtgtgg cttgcaagaa ccrgctcaga  3780
tcctgcscct caaaaacaaa acatgagcgt gccaagaaag tccaaggtgt tgaatgttgc  3840
cacttcaagc ctaaactttc taggaacacc taagtgggtg gcagcttcca gttctccagg  3900
ctgcttctag gccagagctg ggttccacaa gagacagaat aggcatatat atgcttaagg  3960
aactggaaaa acaggctctc tctctctcac aaacacacac acacacatac caaggtagct  4020
gtcaaaatgt tatccgaaat tttgaaacca aaaaatcttg aaagatggta ttccaatatc  4080
acatttatg taagttttct attatattag attcaaatta cgattcgagg ccacaagctt  4140
taagaattca gggcctttt aacttgccaa gccccacacc actccaggaa cttccccaca  4200
ccccagttct cagaattcat gtgcaaggtc tttcctaaat ccagggtcca ggtcagagag  4260
tggaggatgt gctctatttc ttacctgatt gcagacccct ctgacagtgc tcccttctga  4320
agcactcact gtctgaacgt acacagtctc agacttaatc atgcacagtg agcaagactg  4380
tggtgtgata attggcgtcc ctgacttatt agggcaaatc tatgggaggg ggagacctcc  4440
tggaccactg agcaattaat tcatttacat taggaagttt ctccgtcaga tgcaggaaaa  4500
aaatcttgtt ttcctgctgt ggttttgact tttgccccat cttctgttgc tgttgtagga  4560
ggcaaaataa gggtcaaggc ctggaaacac aagtgctttg actgaagctc cacttggctt  4620
ccgaagccca agctgggttg taccaggttc cctagggtgc aggctgtggg caactgccag  4680
ggacatgtgc ctgcccaccg gcctctggcc ctcactgagt tggccaatgg gaaatgacaa  4740
ttgtgaggtg gggactgcct gccccgtga gtaccaggct gttgaggctg gccatctcc  4800
tcctcacttc c att ctg act gca gtc tgt ggt tct gat tcc ata cca gag  4850
              Ile Leu Thr Ala Val Cys Gly Ser Asp Ser Ile Pro Glu
                1           5                  10
g gtaagagcaa ttcgtgaag ttccaggctg ggtggggat gcatgcatag             4901
cctctggctg ggatcaccca ggctctcccg tccgtagtag tgtgggagtg gatacaggtg  4961
gatactctgg tcagagcagc actggtggag gcagatatgc actgggcttc ttcctccgtt  5021
ctcccacagc cccaagagag aaagggttat ttcagacatt ccttctaaga tgcatggaac  5081
cattctgaat tttrcccagt tcgctctgta gcaggatacc tattgagaaa agttagggt  5141
cagtaaggtg gaagggtctg tccacagatg aagtccaatt cgattaaggg ggataaggga  5201
atacattgyc tcttagcttg accaggtagg gcaaaggaag aagcatatat gaaggcagct  5261
tcagaaaagt caagctgagc actgacttca gactggaatt aggaatccag ctctgccact  5321
ttattctact cagcaaatat ttactgagca aattctatgg gctagacagt ggattgggtt  5381
cacaagatac aatgagtgtg acatggttgt tgtctatgga tttggggata tatgtaggta  5441
tagggatatc ttacaaggta atcaagaggt tctaatgagg ccagccatgg tggctcacac  5501
ctgtaatccc agcaatttgg gagaccgagg cgggtggatc acctgaggtc aggagttcca  5561
gactagcctg accaacatgg tgaaacccg cctctaccaa aaatacaaaa attagttggg  5621
cgtgatggca ggtgcctgta atcccagctt ctcgggaggc tgaggcagga gaattgtctg  5681
aacctgggag gcagaggttg cagtgagccg agattgttgc cactgcattc cagcctgggt  5741
```

-continued

```
gacagagcga gactttgtgt caaaaaaaaa aaaaaaaga aagaaaagaa aaagaggctc   5801
taatgagata aaatgagaaa agcctggcat gtagtggcaa cttatgaaaa attgtaatta   5861
aaaaaaaaca ttttctgaca gaagaaactg gatctacctg gttttctga agcctaatcc    5921
tgctcgcccc agtgagtgct gtttctgagg catcctggtt gttttgagct gtggatgctg   5981
aaggttagag tgggagggat tttagaggtt aggtctgccc ctcttgtgtt agaggacatg   6041
gatccctggt ctggagaggt tctggttttt ggatcaagcc tcacaagggg tggcaccaac   6101
tcactcctag gaactccgct agaaggaagg ccagctctgc ctaattcggt tggggagatg   6161
ggggtccctt tatgctagca gaatatgtcc gaaggagcat gatggtgtca gctttgttca   6221
tgaaggccag tggtacacag ggagcccggc agcttcctca gcagtccctg ctgccactct   6281
tccttaagtc ttgaggagtc tttttttggc acaatctcag ctcactgcaa cctccgcctc   6341
ccaggttcaa gcgattctcc tgcctcagtc tcccaagtag ctgagactac aggcatgcgc   6401
caccacgccc agctaatttt tatattttta gtagagatgg ggttcaccat attggccagg   6461
atggtctcga tctcttgacc tcatattcca cctgcctcgg cctcccaaag tgctggtatt   6521
acaggtgtga gccactgcgc ctggccgagg agtcttaagc tgagatcaca gcattgcact   6581
ccagcctggg caaaaagagc aaaactccat ctcaaaaaaa aaaaaaaat agacacaaga    6641
ctggctcctt gtcttttttg gggacagggt ctcactctat cacccaggct ggagtgcagt   6701
ggtgcaatca cagctcactg cagcctcgat ttcccaggct caagtgaccc tcccatctta   6761
gcctcctgag tagctgggac tacaggtgtg tgcaaccatg cctggctaat tttaaaaat   6821
ttttgtaga gatgaggtct cactatattg gctgggggc ctcaaactcc tgggctcagc     6881
agtcctccca cctcagcctc ccaaaaggct gggattatat gcttgctctt tttaaggtgg   6941
ctgtagggac aaactttcca cctactcctt gtcaagccag tggaccggtg gtcccagaca   7001
tacggctaaa gtcaagaggt gatgtctttt ggagagatac tttcaatcag gaatttcaat   7061
cagaaattca atcatgtgga gagagactta tcctaaaaat gtggtggtgc gtgggatgct   7121
ctgtttatt agttccttga cagtatgtat gtgtgtgagt gtgtgtgtgt gcgcgcgcac    7181
actcatttgg atgggtgtgt atgtgtgtgg ggggtggtg cgtacgtatg tggatgtgtg    7241
gatgtggtgt gtgggtgtgc gcgtgcatag gtggaggtgt gtgtatgggt gcgggtatgt   7301
gtgtgtgttg ggcatggaga tattgacagc tctcccaggg ctgagtgaag gctttcgggc   7361
aaagctcctg ggagctaggc aaagctgagt tgattcctgg ttatgccatt tattattggg   7421
ttgcaccgtg tgaaactgcc aatattctac actttgactt ttatttattt ttatttttat   7481
tttttttgag acagagtttc acacttgtca cctaggctgg agtgcagtgg cgcgatctca   7541
gctcactgca acctctgcct catggattca agtgattctc ctgcctcagc ctcccaagta   7601
gctggaatta caggtgcccg ctaccacgcc tgactaattt ttgtattttt ggtagagacg   7661
ggatttcacc atgttgtcca ggctggtctg aaactcctga catcaggtaa tccacccacc   7721
tcagcctccc aaagtgctgg gattacaggc atgagccact gcgcccggcc cattttgact   7781
tttaaaaatg ggagtttgat ataattcaat ccagtggttg aattagctag catcgttccc   7841
tctccaagtc tcaggttctc ctacacgtta gagtcaaaag cagggctatg ggaagattaa   7901
gtaaaataaa ttttgaaaat gccttatgaa aattacactc caaagaactc gcgccagtgt   7961
cagtgttctc atgttcctca tctcacatga tcacatttcg cggattagga agctgagtct   8021
gagaagctcc gtgtagtgct ttttcggagg caccgtgatg tgatggaagg ctcactcgtt   8081
```

```
aggaagtcag aacagagtct ctgagggatc atttccttaa tctgtcagtt tcctcatctc  8141
tgaagttggg ctcatttcct tccttcatgg agttattgta aagatgaaga taaataacgt  8201
gtaaaatcta gcatgggaac tggcttctat aaggttctaa taagtgcatt cctactcctt  8261
cccctcagcc ttcccatttg taaaagcaag gcaggggtga ggtgatttct ggggctcctt  8321
ttggctctga catttgagga ttttgtatcc tttttttttt cagagtcttg ctctgtcacc  8381
caggttggag tgcagctcaa tgcaaattcc gcctcccagg ctcaagcaat tcttatgtct  8441
cagcctcctg agtacctggg attacaggca ggcaccacca cccccagcta attttttgta  8501
ttttcagtag agacggggtt ttgccatatt ggccaggctg gtcttgaact cctgacttca  8561
tgtgacccac ccatctcagc ctcccaaagt gctgagatga caggtgtgag ctaccgtgcc  8621
tggccaattt tgtgtgcttt aatgcccttt tctgctggaa gagttggcac caggtttggt  8681
gatctctttc ccccacacgg ctctgcctcc tgccagtccc agaggggacc ctgtccttgc  8741
atttcacagg attctgctgt tgcaactgaa attccagtag gtcaaagtga aatttctcat  8801
acactttaac atgaagataa atgatcacag tatggcccctt taggatcctg agaacatcac  8861
ggtcatcccc tggtataatt ttaaaagcag atgaatccat gcctgtgcga ggtttgccag  8921
gaaagccagt gctgggatta cagtggaagt cttttttatgc tacttttttc ttgtatccct  8981
caccccatgg ggtggcatat tgaaaggcag gatgtgtgac cacgatactt ttctcctcct  9041
ggactatgtc taagagtctg ttattgggtt ctgaagatca gagtttaatt tccgactcct  9101
ctctgtgtag ctctgggatc ttggaaagcc acttaacctt tctgaagtcc cctttcctca  9161
tctctaaaat gcatacactc atcactaaca tttactgagc actgacatgt gccagacacc  9221
attctaagca ttttacacag actacaccat ttgatcttcc aacaaacaga acactgaaac  9281
gcattacagg tcagaacaaa tgatttgtgc ctaagcacca agaccgtaga gcccgtgctc  9341
cctattctac cctatcctgt ctctcaaaat gattgtgaga atcgaatgag acactaggtg  9401
agaaagggt tttataaata gcattttaaa aattttttaa agtccacaaa attttttaatt  9461
ttaatacaga taaaatagat cccttttgttt tataaaaagt aacaaaattt gttatacaac  9521
aactatgtta tttattaatt ttgccttttt gtatgctgcc aggaaagaaa cattaagaaa  9581
tcttaaattg attatggtga atcagaaggt ctgcctggac ttttttattgc tctaactgta  9641
cagctgatca tactacctca ttttttttta tgacacttca agggtgcgct tagcttcatc  9701
actccttcgt tgccaaaagc tttgtgacca aaaacaatta agcagattcc tgagtcacta  9761
aatgacacat aaccagagtt gagacttagg aactttttagt gccatgctaa gcccacaggg  9821
acacaacaaa tagcatttta caaaggcaaa gaattgtgac acttgagatt tagcttgttg  9881
atccttgtaa aagttttctt tttaggcata attgagtttt agatcatagt actcactatt  9941
acttagtaat aattttttttc tgatagaaat acagtgtaac aggccgggcg cagtggctca  10001
tgcctgtaat cccagcactt gggaggccg aggcggcgg atcacttgag gtcaggagtt  10061
tgagaccagc ccggccaaca tggtgaaatc ccatctctac taaaaataca aaaaattagc  10121
caggtgtggt cgtggattcc tgtgatccca gctacttggg agggtgaggc aggagcatca  10181
gttgaaccca ggaggcggag gttgcagtga gccaagatgg tgccattgca ctccagcctg  10241
ggccacaaag cgagactcca cttcagaaac aaaaaaaaaa agagagagag agaaaagaag  10301
gaaggaagga aggaaggaag gaagaaggaa aggaaggaag gaaggaagga aggaaggaag  10361
gaaggaaaga aggaaggaag gaaagaagga aggaaggaaa gaaggaagga aggaaggaag  10421
gaagggtaac aagcaaagtg taacaatggc aatatctaaa aaaataggta ttttatatg  10481
```

```
tttgtcgttt tatatatatg accccccactt tagagatgag gaaactgaga gattaaggaa   10541
acgatccctg agagactctg ttctgacttc caaatcggtg agctttccat cgcatcacgg   10601
tgcctccgaa agcatgacac ggagcttctc agactyagct tcctaatccg ctaaacggga   10661
ttatgtgaga tgaggaacat gagaacgctg acatgggtga gggttccttg gagtatcatt   10721
ttcatgtggc attttcaaaa cttattttac ctaatcttcc caaagccctg cttttgactc   10781
taatgtgtct cctgagactt ggagagcgca agatgctagc gacagagcaa gactccatct   10841
ccagataaat aaataagtaa aataaaaaag aacacaaata attttgaaaa tttttttgaa   10901
aattaggcac gtttgcactg accttcaatt gttattaatt gctggtttcc cacccagaat   10961
taagttggaa tgcaactttc ttttacaatc agagtccgtt cttggtcttg gaaacttctg   11021
aggctcctgt gctaatcmca ctcttgtatt tttggcacct ctacccgtg ccactgtcat   11081 ggaacccagg ctgatcgcac ctattagtgg agaaatmtgt ccataatact gaagtttggg   11141
gacaaacagt gttcccttag ggtaggagaa agagatcttt attttttraca aaggggagg   11201 agccagaaaa ctccagagac ccctgagttt gccctctctc caaggtttgg ggtaagcccc   11261
ccgtcaccct ttatctctgg ggctttcaca tattctggat tctctcctcc tgtttcccag   11321
cagaaaagga tggagcctca cagattcttc ccatttctgg agaaaaacat gcatggagct   11381
caaagttctt ctcaggagtt ttattgccaa agccataata agaaagggtg gaggtgacaa   11441
gcagtgagga agtttaaaga tgcatgaaat ctgtaaagtc tcagaacaag aattctccta   11501
aaatgcaaaa ggggctttgc tggtctcccc ttggcttctc atgtagctca cctcttttttt   11561 cttatcttga gactagtcaa acctaagctg tttctcattt tatttccaga agctattgag   11621
aacactctcc tgaattcttc aaattcagta gagggcgaca aatgtacata taaatgatgg   11681
tagtgggtct taaataaaga ctcatgacac ctaaaggggc agcacctgag tctgattgca   11741
cctgtttctg ttgctgtttc tgtctctctt ctctctgtct gccatttcat tatcaatggt   11801
tactttactt ataagatcat attagaacct gatatttgat aaatgatgca tcagatctat   11861
agtgagagaa aaaattaatg caattaaagg tgttgtaaca gctagtcttc aagtgggggag   11921 aaatcatttg agtaccttag gtcacagctt acatcaaaac aaaaaatcag agctacatta   11981
aaaagtgaaa ttttaactat atcaaacaat agaaaaaaac agaagaaaat tgaatactta   12041
ctaaatctta gcatgaataa gaactgttta acacttagag gcaaggactg ggcgtggtgg   12101
ctcatgcttt taatcccagg actttgggag cccaaggcgg gcggatcacc tgaggtcagg   12161
agtttgagac tagcctggcc aacatggtga accccgtctc tactaaaaaa atgcaaaaat   12221
tagctgcgtg tggtggtgca tgcctgtaat ctcagctact gggaggcta aggcatgaga   12281 atcgcttgaa cctgggaggt ggaggctgta gtgagccgag attgtgccac tgcactacag   12341
cctgggtgac agtgtgaaat cctctctctc aaaaaaaaaa aaaaaaaaaa gcaaactaga   12401
gcagtgaggt accattattt cctttgctca ctaaactgac aacacacaaa tgttttttat   12461
aatacccaaa gctgatgagg gtagttaagg tatgcccttt tatacacaca ctaatgatgt   12521
actactggtt ggcagtataa catatgctgc catgtgggga tatgtatcag gagacttaaa   12581
aatgtgcata ccttttggtc cagtaattta cttctgggaa tctgtcataa cagaataata   12641
atcttgggga aagctacatg cctaaggata tttaaaatat tatttaaaaa tcaaagtata   12701
atttcttaca gaatataaaa taatatttta aaatgaaaat atgctaaaag tttgatgaaa   12761
tataaatggt caaatatata ttgattatat ccacttacta gactagcact cactctgaga   12821
```

-continued

```
cgttaaaaat agtcattata aaaactagaa aatgccaaag acaaaataaa ggaataaagt   12881
tttacataaa gtatgattcc actatgttta aaaataaaca gagacattct tggagttgag   12941
tattgttttc ttttctgtca tgtccaaaga actatataac tattattttt aatgaactat   13001
atatgtaata tatacatata gtttatatgt atatacaaaa tttatctcat atatatgata   13061
aagatgaaaa atgagttgga tgtgccacgt gaagtgggta gtatagaaac ccaggtaatg   13121
gggcatagga gtgggattcc agataccagg cccatgtttt tggggtgaga ttgccaatca   13181
cggtctttct tccatccctc acagaggagt aggtttgtct tcaacaaacc ttcagttgtc   13241
ctgaagacaa acctaattct ggagacttca tataatctag aagagacaag caaactgatg   13301
aaaaatagtg aatttttaag gtaaaataaa gtacatggac tacactttgt ttagaatcag   13361
attcttggga ttaaccacat taacccacag agggtcttag tgatgcctct aatccaggat   13421
cctaggacct atttctctct gtgagatgct ttctcccaac tccttggtga gagtgggaag   13481
actaagacct cagcaatctg aggtggaggc ctaagatccc cctaagatcg gaggcagaat   13541
ctgagagggg ataaaagtcc ctatacctgt attgggcccct tttctgggag ggggatatca   13601
aagaatgatt ttgagacagg gaggcttttg actacctgtg ccacttgagc tctttgctag   13661
ggctccagaa tacatatttc aaatacattc cccctccctc cttccttccc tcttccactc   13721 ttcctttta tcttccttc ttcttttcct tcctccttcc cttcctttct ctggctctct   13781
catgatttct tttcctcatt ataaaagtgc ttatttagtc cctactctgc tattagtgtg   13841
ttagtctttg tcccctggta cttgctgttt aatggagaaa tgggtgagca aaacagaaat   13901
tacagcagag tgcaataata gagctaagcc aggtgtataa atccattctc acactgctgt   13961
aaaaaactac tgggtaattt ataaagaaaa gaggtttaat tgactcacag ttccacaggc   14021
tgtacaggaa gcatggctgg ggaggcctca gaaaacttac aatcatggtg gaagaaagag   14081
cgaaggggaa gcaagcacat cacacagcag caggagagag agagagaaag agagagagag   14141
agaatatagg ggaagtgcta cacactttca accagatctt gtgagaattc acctactatc   14201
atgagaacag caagggataa gtctgcctcc atgattcagt cacctcctac caggcccctt   14261
ctccaacaca tgtcgacgtg ctatttgggt ggggacacag acccaaacca tattaccagg   14321
gcactggaga aacacagagg ggaaagaacc agccaaggag tgagatggag aacaaggagg   14381
acttcttgaa acagatgaca tccaaactgg gtcctgaaag ctgaatagag attagacagg   14441
ggaggagggg cagctaaaga tggctcaggc aaacaaaggg ccaggggata tgttcatggg   14501
atgatgtgtc tctcgttgtc tgcttaacac aaggtgagtc tctccctccc tctctctctc   14561
tttttctctg tgtgtgtttg tgtgtgtgca tgtgtgcaaa tgtaatatac ccaatagtca   14621
aacatgtgcc ccaggagagg ggtagaggaa gaaagagaat gagagagtaa gaaggaggaa   14681
tagacacaga aaatgagaga raaggggga aagaaaaaga agaaaggagc cagaggagag   14741
aagctggtta gcattraatg gagcaatctg tgtcatcgta cttgggaaac ccaaggatgg   14801
attcttggca agtygactct tggagctttc cctgtgcttg gtcctgtgct cagacatggg   14861
aaaattagag gagtgtcatc tgtgcaatca ctgaattcat aatcttggtg aggaaaggag   14921
actacacaca gggaataatg ctaagtatta cagatttcag ggcagaaaga gatcaaggtg   14981
ggctgcaata ttcagaaaag tcttcctgga aaagttgaat acttagaaag cagctcctag   15041
aagtagackc tgctgagatg gacggagtcc tttgtaggtc ccaactgggt gtgtgtgtgg   15101
ggtctgtctc tccatggcyg acagtgcaca tgtggattcc ag gg  ctc agg atg       15154
                                                  Gly Leu Arg Met
                                                   15
```

| | |
|---|---|
| ctg ttg ctg gga gct gtt cta ctg cta tta gct ctg ccc ggk cat gac<br>Leu Leu Leu Gly Ala Val Leu Leu Leu Ala Leu Pro Xaa His Asp<br>20                        25                     30 | 15202 |
| cag gaa acc acg act caa ggg ccc gga gtc ctg ctt ccc ctg ccc aag<br>Gln Glu Thr Thr Thr Gln Gly Pro Gly Val Leu Leu Pro Leu Pro Lys<br>35                    40                    45 | 15250 |
| ggg gcc tgc aca ggt tgg atg gcg ggc atc cca ggg cat ccg ggc cat<br>Gly Ala Cys Thr Gly Trp Met Ala Gly Ile Pro Gly His Pro Gly His<br>50                      55                  60                  65 | 15298 |
| aat ggg gcc cca ggc cgt gat ggc aga gat ggc acc cct ggt gag aag<br>Asn Gly Ala Pro Gly Arg Asp Gly Arg Asp Gly Thr Pro Gly Glu Lys<br>70                        75                    80 | 15346 |
| ggt gag aaa gga gat cca g gtaagaatgt ttctggcctc tttcatcaca<br>Gly Glu Lys Gly Asp Pro<br>85 | 15395 |
| gacctcctac actgatataa actatatgaa gkcattcatt attaactaag gcctagacac | 15455 |
| agggagaaag caaagctttt ttatgttaac cataagcaac ctgargtgat ttggggttgg | 15515 |
| tcttccaagg atgagtgtag atggtgcctc tataaccaag actttggctt tgctgcatct | 15575 |
| gcagctcctt ttccatcccc tttcccatct tcaccctcat ccctattccc agtacattca | 15635 |
| tattctgatt cctctttctg tctgcttaac ttccatttca cccastggca ttcaaccaca | 15695 |
| tttactgcac accccctgaa aggctcagtc ctgcctttgg ggaactcttg atctaggtaa | 15755 |
| gatgtctaat gtgcaaggct ctgttggtgg ttacyacaag aaagtctact ctaaaaatgt | 15815 |
| caaactgaat gtgaacaagt attcaaagta tggagcatag agaaaatrta ctcaccgtgg | 15875 |
| acctgatgaa gaatgaaggc ttcaaggagg aggcagagct tcagctaggc cttgaatgat | 15935 |
| gggtaggcag aatagaggag gagagacatc ctagatggag ggggtagaat tgcaaaacca | 15995 |
| gggttgatgg tgccagcaca taagggctg gcagggtgga gggtctatga tagagaccta | 16055 |
| taggagataa agatagagtt gaaattatgg gagcctccat gtctgtggga gatatagaag | 16115 |
| gaggaggtaa cacctctctc cttttgggag ctcttattgg tttcttgatc tataagtcaa | 16175 |
| gaaggttgtg agtgggagcc acaggatgg taatttaggc tgtaaccaac ctaggcagga | 16235 |
| gttctgttct ttgtagtcac tgaggtcttc tcattcctta g gt   ctt att ggt cct<br>                                                                              Gly Leu Ile Gly Pro<br>                                                                                     90 | 16290 |
| aag gga gac atc ggt gaa acc gga gta ccc ggg gct gaa ggt ccc cga<br>Lys Gly Asp Ile Gly Glu Thr Gly Val Pro Gly Ala Glu Gly Pro Arg<br>95                        100                     105 | 16338 |
| ggc ttt ccg gga atc caa ggc agg aaa gga gaa cct gga gaa ggt gcc<br>Gly Phe Pro Gly Ile Gln Gly Arg Lys Gly Glu Pro Gly Glu Gly Ala<br>110                   115                    120 | 16386 |
| tat gta tac cgc tca gca ttc agt gtg gga ttg gag act tac gtt act<br>Tyr Val Tyr Arg Ser Ala Phe Ser Val Gly Leu Glu Thr Tyr Val Thr<br>125                   130                    135                    140 | 16434 |
| atc ccc aac atg ccc att cgc ttt acc aag atc ttc tac aat cag caa<br>Ile Pro Asn Met Pro Ile Arg Phe Thr Lys Ile Phe Tyr Asn Gln Gln<br>                     145                    150                    155 | 16482 |
| aac cac tat gat ggc tcc act ggt aaa ttc cac tgc aac att cct ggg<br>Asn His Tyr Asp Gly Ser Thr Gly Lys Phe His Cys Asn Ile Pro Gly<br>                 160                    165                    170 | 16530 |
| ctg tac tac ttt gcc tac cac atc aca gtc tat atg aag gat gtg aag<br>Leu Tyr Tyr Phe Ala Tyr His Ile Thr Val Tyr Met Lys Asp Val Lys<br>                 175                    180                    185 | 16578 |
| gtc agc ctc ttc aag aag gac aag gct atg ctc ttc acc tat gat cag<br>Val Ser Leu Phe Lys Lys Asp Lys Ala Met Leu Phe Thr Tyr Asp Gln | 16626 |

```
          190                 195                 200
tac cag gaa aat aat gtg gac cag gcc tcc ggc tct gtg ctc ctg cat         16674
Tyr Gln Glu Asn Asn Val Asp Gln Ala Ser Gly Ser Val Leu Leu His
205                 210                 215                 220 ctg gag gtg ggc gac caa gtc tgg ctc cag gtg tat ggg gaa gga gag         16722
Leu Glu Val Gly Asp Gln Val Trp Leu Gln Val Tyr Gly Glu Gly Glu
                225                 230                 235 cgt aat gga ctc tat gct gat aat gac aat gac tcc acc ttc aca ggc         16770
Arg Asn Gly Leu Tyr Ala Asp Asn Asp Asn Asp Ser Thr Phe Thr Gly
                240                 245                 250 ttt ctt ctc tac cat gac acc aac tga tca cca cta act cag agc ctc         16818
Phe Leu Leu Tyr His Asp Thr Asn     Ser Pro Leu Thr Gln Ser Leu
                255                 260                 265 ctc cag gcc aaa cag ccc caa agt caa tta aag gct ttc agt acg gtt         16866
Leu Gln Ala Lys Gln Pro Gln Ser Gln Leu Lys Ala Phe Ser Thr Val
                270                 275                 280 agg aag ttg att att att tag ttg gag gcc ttt aga tat tat tca ttc         16914
Arg Lys Leu Ile Ile Ile     Leu Glu Ala Phe Arg Tyr Tyr Ser Phe
285                 290                 295 att tac tca ttc att tat tca ttc att cat caa gta act tta aaa aaa         16962
Ile Tyr Ser Phe Ile Tyr Ser Phe Ile His Gln Val Thr Leu Lys Lys
                300                 305                 310 tca tat gct atg ttc cca gtc ctg gga agc ttc aca aac atg acc aga         17010
Ser Tyr Ala Met Phe Pro Val Leu Gly Ser Phe Thr Asn Met Thr Arg
315                 320                 325                 330 taa ctg act aga aag aag tag ttg aca gtg cta ttt tgt gcc cac tgt         17058
    Leu Thr Arg Lys Lys     Leu Thr Val Leu Phe Cys Ala His Cys
                335                     340 ctc tcc tga tgc tca tat caa tcc tat aag gca cag gga aca agc att         17106
Leu Ser     Cys Ser Tyr Gln Ser Tyr Lys Ala Gln Gly Thr Ser Ile
345                 350                 355 ctc ctg ttt tta cag att gta tcc tga ggc tga gag agt taa gtg aat         17154
Leu Leu Phe Leu Gln Ile Val Ser     Gly     Glu Ser     Val Asn
360                 365                                 370 gtc taa ggt cac aca agt att aag tga cag tgc tag aaa tca aac cca         17202
Val     Gly His Thr Ser Ile Lys     Gln Cys     Lys Ser Asn Pro
                375                 380                 385 gag ctg tgg act ttg ttc act aga ctg tgc cct ttt ata gag gta cat         17250
Glu Leu Trp Thr Leu Phe Thr Arg Leu Cys Pro Phe Ile Glu Val His
                390                 395                 400 gtt ctc ttt gga gtg ttg gta ggt gtc tgt ttc cca cct cac ctg aga         17298
Val Leu Phe Gly Val Leu Val Gly Val Cys Phe Pro Pro His Leu Arg
                405                 410                 415 gcc att gaa ttt gcc ttc ctc atg aat taa aac ctc ccc caa gca gag         17346
Ala Ile Glu Phe Ala Phe Leu Met Asn     Asn Leu Pro Gln Ala Glu
                420                 425                 430 ctt cct cag aga aag tgg ttc tat gat gaa gtc ctg tct tgg aag gac         17394
Leu Pro Gln Arg Lys Trp Phe Tyr Asp Glu Val Leu Ser Trp Lys Asp
                435                 440                 445 tac tca atg gcc cct gca cta ctc tac ttc ctc tta cct atg tcc         17442
Tyr Tyr Ser Met Ala Pro Ala Leu Leu Tyr Phe Leu Leu Pro Met Ser
                450                 455                 460 ctt ctc atg cct ttc cct cca acg ggg aaa gcc aac tcc atc tct aag         17490
Leu Leu Met Pro Phe Pro Pro Thr Gly Lys Ala Asn Ser Ile Ser Lys
465                 470                 475                 480 tgc tga act cat ccc tgt tcc tca agg cca cct ggc cag gag ctt ctc         17538
Cys     Thr His Pro Cys Ser Ser Arg Pro Pro Gly Gln Glu Leu Leu
                485                 490                 495 tga tgt gat atc cac ttt ttt ttt ttt ttg aga tgg agt ctc act ctg         17586
```

```
                Cys Asp Ile His Phe Phe Phe Leu Arg Trp Ser Leu Thr Leu
                                500             505             510
tca ccc agg ctg gag tac agt gac acg acc tcg gct cac tgc agc ctc         17634
Ser Pro Arg Leu Glu Tyr Ser Asp Thr Thr Ser Ala His Cys Ser Leu
                515             520             525
ctt ctc ctg ggt cca agc aat tat tgt gcc tca gcc tcc cga gta gct         17682
Leu Leu Leu Gly Pro Ser Asn Tyr Cys Ala Ser Ala Ser Arg Val Ala
                530             535             540
gag act tca ggt gca ttc cac cac aca tgg cta att ttt gta ttt tta         17730
Glu Thr Ser Gly Ala Phe His His Thr Trp Leu Ile Phe Val Phe Leu
                545             550             555
gta gaa atg ggg ttt cgt cat gtt ggc cag gct ggt ctc gaa ctc ctg         17778
Val Glu Met Gly Phe Arg His Val Gly Gln Ala Gly Leu Glu Leu Leu
                560             565             570
gcc tag gtg atc cac ccg cct cga cct ccc aaa gtg ctg gga tta cag         17826
Ala     Val Ile His Pro Pro Arg Pro Pro Lys Val Leu Gly Leu Gln
575                         580             585
gcr tga gcc acc atg ccc agt cga tat ctc act ttt tat ttt gcc atg         17874
Ala     Ala Thr Met Pro Ser Arg Tyr Leu Thr Phe Tyr Phe Ala Met
590             595                 600
gat gag agt cct ggg tgt gag gaa cac ctc cca cca ggc tag agg caa         17922
Asp Glu Ser Pro Gly Cys Glu Glu His Leu Pro Pro Gly     Arg Gln
605             610             615
ctg ccc agg aag gac tgt gct tcc gtc acc tct aaa tcc ctt gca gat         17970
Leu Pro Arg Lys Asp Cys Ala Ser Val Thr Ser Lys Ser Leu Ala Asp
620             625             630             635
cct tga taa atg cct cat gaa gac caa tct ctt gaa tcc crt atc tac         18018
Pro         Met Pro His Glu Asp Gln Ser Leu Glu Ser Xaa Ile Tyr
                            640             645
cca gaa tta act cca ttc cag tct ctg cat gta atc agt ttt atc cac         18066
Pro Glu Leu Thr Pro Phe Gln Ser Leu His Val Ile Ser Phe Ile His
650             655             660             665
aga aac att ttc att tta gga aat ccc tgg ttt taa gta tca atc ctt         18114
Arg Asn Ile Phe Ile Leu Gly Asn Pro Trp Phe     Val Ser Ile Leu
                670             675                 680
gtt cag ctg gac aat atg aat ctt ttc cac tga agt tag gga tga ctg         18162
Val Gln Leu Asp Asn Met Asn Leu Phe His     Ser     Gly     Leu
                685             690
tga ttt tca gaa cac gtc cag aat ttt tca tca aga agg tag ctt gag         18210
    Phe Ser Glu His Val Gln Asn Phe Ser Ser Arg Arg     Leu Glu
        695             700             705
cct gaa atg caa aac cca tgg agg aat tct gaa gcc att gtc tcc ttg         18258
Pro Glu Met Gln Asn Pro Trp Arg Asn Ser Glu Ala Ile Val Ser Leu
                710             715             720
agt acc aac agg gtc agg gaa gac tgg gcc tcc tga att tat tat tgt         18306
Ser Thr Asn Arg Val Arg Glu Asp Trp Ala Ser     Ile Tyr Tyr Cys
725             730                 735
tct tta aga att aca ggt tga ggt agt tga tgg tgg taa aca ttc tct         18354
Ser Leu Arg Ile Thr Gly     Gly Ser     Trp Trp     Thr Phe Ser
740                 745                         750
cag gag aca ata act cca gtg atg ttc ttc aaa gat ttt agc aaa aac         18402
Gln Glu Thr Ile Thr Pro Val Met Phe Phe Lys Asp Phe Ser Lys Asn
                755             760             765
aga gta aat agc att ctc tat caa tat ata aat tta aaa aac tat ctt         18450
Arg Val Asn Ser Ile Leu Tyr Gln Tyr Ile Asn Leu Lys Asn Tyr Leu
                770             775             780
ttt gct tac agt ttt aaa tcc tga aca att ctc tct tay atg tgt att         18498
Phe Ala Tyr Ser Phe Lys Ser     Thr Ile Leu Ser Tyr Met Cys Ile
785             790                 795
```

```
gct aat cat taa ggt att att ttt tcc aca tat aaa gct ttg tct ttt    18546
Ala Asn His     Gly Ile Ile Phe Ser Thr Tyr Lys Ala Leu Ser Phe
800                 805                 810 tgt tgt tgt tgt tgt ttt taa gat gga gtt tcc ctc tgt tgc cag gct    18594
Cys Cys Cys Cys Cys Phe     Asp Gly Val Ser Leu Cys Cys Gln Ala
815                         820                 825 aga gtg cag tgg cat gat ctc ggc tta ctg caa cct ttg cct ccc agg    18642
Arg Val Gln Trp His Asp Leu Gly Leu Leu Gln Pro Leu Pro Pro Arg
830                 835                 840 ttc aag cga ttc ttc tgc ctc agc ctc ccg agt agc tgg gac cac agg    18690
Phe Lys Arg Phe Phe Cys Leu Ser Leu Pro Ser Ser Trp Asp His Arg
845                 850                 855                 860 tgc cta cca cca tgc cag gct aat ttt tgt att ttt agt aaa gac agg    18738
Cys Leu Pro Pro Cys Gln Ala Asn Phe Cys Ile Phe Ser Lys Asp Arg
                865                 870                 875 gtt tca cca tat tgg cca ggc tgg tct cga act cct gac ctt gtg atc    18786
Val Ser Pro Tyr Trp Pro Gly Trp Ser Arg Thr Pro Asp Leu Val Ile
            880                 885                 890 tgc cca cct cca ttt ttg ttg tta ttt ttt gag aaa gat aga tat gag    18834
Cys Pro Pro Pro Phe Leu Leu Leu Phe Phe Glu Lys Asp Arg Tyr Glu
            895                 900                 905 gtt tag aga ggg atg aag agg tga gag taa gcc ttg tgt tag tca gaa    18882
Val     Arg Gly Met Lys Arg     Glu     Ala Leu Cys     Ser Glu
        910                 915                         920 ctc tgt gtt gtg aat gtc att cac aac aga aaa ccc aaa ata tta tgc    18930
Leu Cys Val Val Asn Val Ile His Asn Arg Lys Pro Lys Ile Leu Cys
                925                 930                 935 aaa cta ctg taa gca aga aaa ata aag gaa aaa tgg aaa cat tta ttc    18978
Lys Leu Leu     Ala Arg Lys Ile Lys Glu Lys Trp Lys His Leu Phe
                940                 945                 950 ctt tgc ata ata gaa att acc aga gtt gtt ctg tct tta gat aag gtt    19026
Leu Cys Ile Ile Glu Ile Thr Arg Val Val Leu Ser Leu Asp Lys Val
            955                 960                 965 tga acc aaa gct caa aac aat caa gac cct ttt ctg tat gtc ctt ctg    19074
    Thr Lys Ala Gln Asn Asn Gln Asp Pro Phe Leu Tyr Val Leu Leu
        970                 975                 980 ttc tgc ctt ccg cag tgt agg ctt tac cct cag gtg cta cac agt ata    19122
Phe Cys Leu Pro Gln Cys Arg Leu Tyr Pro Gln Val Leu His Ser Ile
        985                 990                 995 gtt cta ggg ttt ccc tcc cga tat caa aaa gac tgt  ggc ctg ccc      19167
Val Leu Gly Phe Pro Ser Arg Tyr Gln Lys Asp Cys  Gly Leu Pro
1000                1005                1010 agc tct cgt atc ccc aag cca cac cat ctg gct aaa tgg aca tca       19212
Ser Ser Arg Ile Pro Lys Pro His His Leu Ala Lys Trp Thr Ser
1015                1020                1025 tgt ttt ctg gtg atg ccc aaa gag gag aga gga agc tct ctt tcc       19257
Cys Phe Leu Val Met Pro Lys Glu Glu Arg Gly Ser Ser Leu Ser
1030                1035                1040 cag atg ccc cag caa gtg taa cct tgc atc tca ttg ctc tgg ctg       19302
Gln Met Pro Gln Gln Val     Pro Cys Ile Ser Leu Leu Trp Leu
1045                    1050                1055 agt tgt gtg cct gtt tct gac caa tca ctg agt cag gag gat gaa       19347
Ser Cys Val Pro Val Ser Asp Gln Ser Leu Ser Gln Glu Asp Glu
        1060                1065                1070 ata ttc ata ttg act taa ttc cag ctt aag tta ggg gta tgt aga       19392
Ile Phe Ile Leu Thr     Leu Gln Leu Lys Leu Gly Val Cys Arg
        1075                1080                1085 ggt att ttc cct aaa gca aaa ttg gga cac tgt tat cag aaa tag       19437
Gly Ile Phe Pro Lys Ala Lys Leu Gly His Cys Tyr Gln Lys
        1090                1095                1100
```

-continued

```
gag agt gga tga tag atg caa aat aat acc tgt cca caa caa act ctt    19485
Glu Ser Gly     Met Gln Asn Asn Thr Cys Pro Gln Gln Thr Leu
            1105                1110 aat gct gtg ttt gag ctt tca tga gtt tcc cag aga gac ata gct        19530
Asn Ala Val Phe Glu Leu Ser     Val Ser Gln Arg Asp Ile Ala
1115                1120                1125 gga aaa ttc cta ttg att ttc tct aaa att tca aca agt agc taa        19575
Gly Lys Phe Leu Leu Ile Phe Ser Lys Ile Ser Thr Ser Ser
    1130                1135                1140 agt ctg gct atg ctc aca gtc tca cat ctg gtt ggg gtg ggc tcc        19620
Ser Leu Ala Met Leu Thr Val Ser His Leu Val Gly Val Gly Ser
        1145                1150                1155 tta cag aac acg ctt tca cag tta ccc taa act ctc tgg ggc agg        19665
Leu Gln Asn Thr Leu Ser Gln Leu Pro     Thr Leu Trp Gly Arg
        1160                1165                1170 gtt att cct ttg tgg aac cag agg cac aga gag agt caa ctg agg        19710
Val Ile Pro Leu Trp Asn Gln Arg His Arg Glu Ser Gln Leu Arg
        1175                1180                1185 cca aaa gag gcc tga gag aaa ctg agg tca aga ttt cag gat taa        19755
Pro Lys Glu Ala     Glu Lys Leu Arg Ser Arg Phe Gln Asp
        1190                1195 tgg tcc tgt gat gct ttg aag tac aat tgt gga ttt gtc caa ttc        19800
Trp Ser Cys Asp Ala Leu Lys Tyr Asn Cys Gly Phe Val Gln Phe
1200                1205                1210 tct tta gtt ctg tca gct ttt gct tca tat att tta gcg ctc tat        19845
Ser Leu Val Leu Ser Ala Phe Ala Ser Tyr Ile Leu Ala Leu Tyr
1215                1220                1225 tat tag ata tat aca tgt tta gta tta tgt ctt att ggt gca ttt        19890
Tyr     Ile Tyr Thr Cys Leu Val Leu Cys Leu Ile Gly Ala Phe
1230                1235                1240 act ctc tta tca tta tgt aat gtc ctt ctt tat ctg tga taa ttt        19935
Thr Leu Leu Ser Leu Cys Asn Val Leu Leu Tyr Leu         Phe
    1245                1250                1255 tct gtg ttc tga agt cta ctt tgt cta aaa ata aca tac gca ctc        19980
Ser Val Phe     Ser Leu Leu Cys Leu Lys Ile Thr Tyr Ala Leu
            1260                1265                1270 aac ttc ctt ttc ttt ctt cct tcc ttt ctt tct tcc ttc ctt tct        20025
Asn Phe Leu Phe Phe Leu Pro Ser Phe Leu Ser Ser Phe Leu Ser
            1275                1280                1285 ttc tct ctc tct ctc ttt cct tcc ttc ctt cct cct ttt ctt tct        20070
Phe Ser Leu Ser Leu Phe Pro Ser Phe Leu Pro Pro Phe Leu Ser
            1290                1295                1300 ctc tct ctc tct ctc tct ttt ttt gac aga ctc tcg ttc tgt ggc        20115
Leu Ser Leu Ser Leu Ser Phe Phe Asp Arg Leu Ser Phe Cys Gly
            1305                1310                1315 cct ggc tgg agt tca gtg gtg tga tct tgg ctc act gct acc tct        20160
Pro Gly Trp Ser Ser Val Val     Ser Trp Leu Thr Ala Thr Ser
            1320                1325 acc atg agc aat tct cct gcc tca gcc tcc caa gta gct gga act        20205
Thr Met Ser Asn Ser Pro Ala Ser Ala Ser Gln Val Ala Gly Thr
1330                1335                1340 aca ggc tca tgc cac tgc gcc cag cta att ttt gta ttt ttc gta        20250
Thr Gly Ser Cys His Cys Ala Gln Leu Ile Phe Val Phe Phe Val
1345                1350                1355 gag acg ggg ttt cac cac att cgt cag gtt ggt ttc aaa ctc ctg        20295
Glu Thr Gly Phe His His Ile Arg Gln Val Gly Phe Lys Leu Leu
1360                1365                1370 act ttg tga tcc acc cgc ctc ggc ctc cca aag tgc tgg gat tac        20340
Thr Leu     Ser Thr Arg Leu Gly Leu Pro Lys Cys Trp Asp Tyr
```

-continued

| | | | | | | | | | | | | |
|---|---|---|---|---|---|---|---|---|---|---|---|---|
|1375| | | |1380| | | |1385| | | | |
|agg|cat|gag|cca|tca|cac|ctg|gtc|aac|ttt|ctt|ttg|att agt gtt|
|Arg|His|Glu|Pro|Ser|His|Leu|Val|Asn|Phe|Leu|Leu|Ile Ser Val|
| |1390| | | | |1395| | | |1400| | |

Line numbers and translations:

```
        1375              1380              1385
agg cat gag cca tca cac ctg gtc aac ttt ctt ttg att agt gtt    20385
Arg His Glu Pro Ser His Leu Val Asn Phe Leu Leu Ile Ser Val
    1390              1395              1400 ttt gtg gta tat ctt ttt cca tca tgt tac ttt aaa tat atc tat    20430
Phe Val Val Tyr Leu Phe Pro Ser Cys Tyr Phe Lys Tyr Ile Tyr
    1405              1410              1415 att att gta ttt aaa atg tgt ttc tta cag act gca tgt agt tgg    20475
Ile Ile Val Phe Lys Met Cys Phe Leu Gln Thr Ala Cys Ser Trp
    1420              1425              1430 gta taa ttt tta tcc agt cta aaa ata tct gtc ttt taa ttg gtg    20520
Val     Phe Leu Ser Ser Leu Lys Ile Ser Val Phe     Leu Val
        1435              1440              1445 ttt aga caa ttt ata ttt aat aaa att gtt gaa ttt aag atggatgact  20569
Phe Arg Gln Phe Ile Phe Asn Lys Ile Val Glu Phe Lys
            1450              1455 gttttatttg tttgctgttc accacttctg ttttattctc tttccagaat tcttttggat 20629 tgtttaaata tttcataata ttttatctta atttatttat tgggtatttg cctatatctc  20689
tttgtggtat tttttagtgg ttgcttgagg gattacaatg tacttaactt ttcacagtgt  20749
gcataaagtt aatattttgc cacttgcagt aaaccgtaga aggcttataa tcatattagt  20809
acctctatcc actttctttt atgttgtagt tgtcatatat attacatcta tatacactga  20869
aacattatag gcaatgttat gattttttgca ttcgtcagtc atatatatat tttaaagaat  20929
ttaagaggag aaaaatacat attcagatat tcatcat                           20966
```

<210> SEQ ID NO 2
<211> LENGTH: 4811
<212> TYPE: DNA
<213> ORGANISM: Homo sapiens

<400> SEQUENCE: 2

```
gctgatctgc tgcctcagcc ttcccaaagt gctgtaattt attaggcata agccactgtg    60
cctgcctagt gttgtacatt ctgtgggttt tgacaattgt atgcatctac atgtatgtac   120
catttatagt attcctgttt ttaattttag ccattctagt aggcatgtag tgatatctca   180
tggtgatttt aatttgcgtt tccgtaatgg ttaataatgc tgaacatctt tgcatgtgct   240
tgtttgtcat ttgtgtttcc tacttggtga ataattgtt catgtccttt gtccattttc    300
taattgaatt ttttttttacc atttagtttt gagatttctt tatacaatct agatccaaat   360
ctcttgtctc aaatatggtt tgcaaataca ttcctctaat tcatatattg ccttttcctc   420
ctcttaacag gatgtttcac agagcaaaag ttttagttttt gttgaaatct cacttttcat   480
tttttctttt agtggattgt gcttttgttg tcatatgtaa gaactcttca ctggccctag    540
atccttgtat tggtttccta agattgccat agcaaatcac catgaactta gtgacaaaaa    600
gacagaaatt tattttcact tcctactgtg ggcagactag acgttaatta ttttcatgta    660
tgctcattcc tatgacatct ttctgatata ataattatag ttattcttaa gcttcaccct    720
tttttctatt agctttgtta ccttgggtgt cactttttct tttttgacat tgtgacctat    780
gccagatcat gtctgttagt acttagccct ccattcacct ctccataatc ccttttgtat    840
tcctggagct tgatgcctga atgacacat cctacattcc tttgccagat gggtaccagt    900
tagcttgtgc acatgggaga caaccgtgaa aagactgaag tggggaagaa gggaggagct    960
gttgtgtttc agtgagcgcc cttggcagtg gcggtgacag tggctcctgt tcagtggcaa   1020
tggtggagca gctagcaaga catgcagtaa gcgcaggctc ataggctatg gtccaggagc   1080
```

-continued

```
agtcaccgat tcctggtctt taggcaatat catctccctt tgcttctcca gcctttctaa    1140
aattattgta ccttgactag tacaattttt tagtattggg ggtagtccaa ggacacaggc    1200
tttaaaaagt atgaattcag ggttgcctac ctgcattgac tgcgcttgaa tcatgatggc    1260
cttctggtcg gtggcaggag gtgacagtcc aaatcatgca gtagcaaacc agatacttaa    1320
attatcatct gagatacttc agaagtacag ccgtagccat ccttcagaa gagataaaga    1380 aatgttctcc tggccaggcg cggtggctca cgcctgtcat tccagcactt tgggaggccg    1440 aggggtgga tcacctgagg tcgggagttc gagaccagcc tgaccaacat ggggaaaccc    1500
tgtctctact aaaaatacaa aattagcggg gcgtggtggc acatgcccat aatcccagct    1560
actcgggagg ctaaggcagg ataatcgctt gaacctgaga ggcagaggtt gcggtgaact    1620
gagatcatgc catagtactc cagcctgggc aacaagagtg aaactccatc tcaaaaaaaa    1680
aaaaaagaaa aaaagataaa gaaatgttct cctttcttgc catttctagg ggtttgggga    1740
tggcgtacat tgctgcaggg cgtgctcact ctaccatctt gctccaatct ttattttca    1800 aaatacagtg cttatgcttg gttacttcag ttaagattat ttttaaaaat cataattaag    1860
caaaaatata tggccatgct taaacatatt taagataaat taagtgattt ggcctgtttc    1920
agtatcccaa ctcacatgct aacagggggct tgacctgtag ctacggtacc ctggaggaaa    1980
tgatcgcatt tatttggtta tttcggtcta agtagtaata gttctgtcct gggaaaaga    2040 ctagcctcaa ggcatttctg attgaatgtt tttcaattac agtctttaaa ccagtatgcc    2100
acagaactgg ctcttccac atgacggcct ttgtggtggg tggcagattg ccctgaggcc    2160
tcgcaaaatg ctaggctttc acaatgtcac tgactgacag ccaggcccag cacagtcttg    2220
gtgtgattgt ggggctaaag ttattccacc ttgtgcaata gctacagcct tctctaacca    2280
gctgcattct tataaagtta gaagaaaata ctttttttt tttgagatgg attctcgctc    2340
tgttgcccag gctggagtgc aatggtgcga tctcggctcg ctgcaacctc cgcctcctgg    2400
gttcaaacga ttctcctccc tcagacccc gagtagctgg gattgcaggt gcctgccacc    2460
acgcccggct aacttttttg tattttagt ggagacgggg tttcaccatc ttcgtcaggc    2520
tggtctcaga ctcctgacct caagtgatct gcccgcctca gcctcccaaa atgctgggat    2580
tacaggcatg agctactgtg cccggccaaa gaaaatactt tttatgccag ccctgaaact    2640
accctgaagc acatacatca accttgaggc ctcacactcc atcaagaggg gtgaagggca    2700
tgaggaatta gaaagcatag ggattttag ttagacagat ctggttcaaa tcctagactt    2760
gtgccttgaa caaattattt accctcattg aactctagat tcattatttg taaaatgaaa    2820
gacaataata gttatctcca aaggaaagtt gaatatgatc attcattat tcattaattc    2880 aacatttatt attgcctact ttgtgccagg ttctattcta ggaactaagg gatacaactt    2940
tgaataggca aaatctctgc tctcctgaag tttactttt ttttttttt ttgagacaga    3000 gtttcactct tgtcacccag gctggagcgc aatggtgctc ttggctcact gcaacctcca    3060
cctcctgggt tcaagtgatt ctcttgtctc agcctcccaa gtagctggga ctacaggtat    3120
gtgccaccac gcccggctat ttctgcattt ttagtagaga tggggtttca ccatgttggc    3180
cagactggtc tcaaactcct gatctcaggt gatatgcctg tcttggcctt ccaaagtact    3240
gggattacag gcctgagcca ctgcacctga cctgaagttt atgttctatt aaatagcaac    3300
agacagtaac ataaaccaaa aataaatagg aaaacaccat aacaaaaatc aaacagtgat    3360
ataattgaga gttgcttcta tttctttttg ttgtcttctt ggttcaatca gcctgctaaa    3420
```

-continued

```
ctatatggaa cctcattttc atgggccact tatttaagcc gggggacctt ggaaagtctc    3480
tcatgtctct catctcaacg gcctaatgtg acttctcttg aaatatttgg acattagcag    3540
gaagctgagg ctttacatca gatctttact ttaatggtgg acttgacttt actggtagat    3600
ttttaggctc tgtgtggact gtggagatga tatctggggg gcaggcagac acttgccctg    3660
cctctgtctg agaaaattct gttttggatg tcttgttgaa gttggtgctg gcatcctaag    3720
cccttgctgg ggtcgtaatt taattcatca gaatgtgtgg cttgcaagaa ccggctcaga    3780
tcctgcgctt caaaaacaaa acatgagcgt gccaagaaag tccaaggtgt tgaatgttgc    3840
cacttcaagc ctaaactttc taggaacacc taagtgggtg gcagcttcca gttctccagg    3900
ctgcttctag gccagagctg ggttccacaa gagacagaat aggcatatat atgcttaagg    3960
aactggaaaa acaggctctc tctctctcac aaacacacac acacacatac caaggtagct    4020
gtcaaaatgt tatccgaaat tttgaaacca aaaaatcttg aaagatggta ttccaatatc    4080 acatttatg taagttttct attatattag attcaaatta cgattcgagg ccacaagctt    4140
taagaattca gggccttttt aacttgccaa gccccacacc actccaggaa cttccccaca    4200
ccccagttct cagaattcat gtgcaaggtc tttcctaaat ccagggtcca ggtcagagag    4260
tggaggatgt gctctatttc ttacctgatt gcagacccct ctgacagtgc tcccttctga    4320
agcactcact gtctgaacgt acacagtctc agacttaatc atgcacagtg agcaagactg    4380
tggtgtgata attggcgtcc ctgacttatt agggcaaatc tatgggaggg ggagacctcc    4440
tggaccactg agcaattaat tcatttacat taggaagttt ctccgtcaga tgcaggaaaa    4500
aaatcttgtt ttcctgctgt ggttttgact tttgccccat cttctgttgc tgttgtagga    4560
ggcaaaataa gggtcaaggc ctggaaacac aagtgctttg actgaagctc cacttggctt    4620
ccgaagccca agctgggttg taccaggttc cctagggtgc aggctgtggg caactgccag    4680
ggacatgtgc ctgcccaccg gcctctggcc ctcactgagt tggccaatgg gaaatgacaa    4740
ttgtgaggtg gggactgcct gcccccgtga gtaccaggct gttgaggctg gccatctcc    4800 tcctcacttc c                                                        4811

<210> SEQ ID NO 3
<211> LENGTH: 407
<212> TYPE: DNA
<213> ORGANISM: Homo sapiens

<400> SEQUENCE: 3
atggatgact gttttatttg tttgctgttc accacttctg ttttattctc tttccagaat      60
tcttttggat tgtttaaata tttcataata ttttatctta atttatttat tgggtatttg     120
cctatatctc tttgtggtat tttttagtgg ttgcttgagg gattacaatg tacttaactt     180
ttcacagtgt gcataaagtt aatattttgc ccacttgcagt aaaccgtaga aggcttataa    240
tcatattagt acctctatcc actttctttt atgttgtagt tgtcatatat attacatcta     300
tatacactga acattatag gcaatgttat gattttttgca ttcgtcagtc atatatatat    360
tttaaagaat ttaagaggag aaaaatacat attcagatat tcatcat                   407

<210> SEQ ID NO 4
<211> LENGTH: 366
<212> TYPE: DNA
<213> ORGANISM: Homo sapiens
<220> FEATURE:
<221> NAME/KEY: misc_feature
<222> LOCATION: (267)..(267)
<223> OTHER INFORMATION: n=a, g, c or t
```

<400> SEQUENCE: 4

```
attctgactg cagtctgtgg ttctgattcc ataccagagg ggctcaggat gctgttgctg      60
ggagctgttc tactgctatt agctctgccc gggcatgacc aggaaaccac gactcaaggg     120
cccggagtcc tgcttccct gcccaagggg gcctgcacag gttggatggc gggcatccca     180
gggcatccgg gccataatgg gccccaggc cgtgatggca gagatggcac ccctggtgag     240
aagggtgaga aaggagatcc aggtctnatt ggtcctaagg gagacatcgg tgaaacggag    300 tacccgggc tgaaggtccc cgaggctttc cgggaatcca aggcaggaaa ggagaaccgg     360
agaagg                                                                366
```

```
<210> SEQ ID NO 5
<211> LENGTH: 4545
<212> TYPE: DNA
<213> ORGANISM: Homo sapiens
<220> FEATURE:
<221> NAME/KEY: CDS
<222> LOCATION: (49)..(783)
<223> OTHER INFORMATION:
<221> NAME/KEY: misc_feature
<222> LOCATION: (1)..(367)
<223> OTHER INFORMATION: homology with 5' EST A254990 in private bank :
      GENSET
<221> NAME/KEY: misc_feature
<222> LOCATION: (91)..(93)
<223> OTHER INFORMATION: Amino acid at position 15 (Xaa) means Gly
<221> NAME/KEY: misc_feature
<222> LOCATION: (15)..(15)
<223> OTHER INFORMATION: The 'Xaa' at location 15 stands for Gly.
<221> NAME/KEY: polyA_signal
<222> LOCATION: (2937)..(2942)
<223> OTHER INFORMATION: AATAAA potential
<221> NAME/KEY: polyA_signal
<222> LOCATION: (4525)..(4530)
<223> OTHER INFORMATION: AATAAA
<221> NAME/KEY: allele
<222> LOCATION: (93)..(93)
<223> OTHER INFORMATION: 9-12-124 : polymorphic base G or T
<221> NAME/KEY: allele
<222> LOCATION: (1156)..(1156)
<223> OTHER INFORMATION: 9-16-189 : polymorphic base deletion of A
<221> NAME/KEY: allele
<222> LOCATION: (1815)..(1815)
<223> OTHER INFORMATION: 17-37-629 : polymorphic base A or G
<221> NAME/KEY: allele
<222> LOCATION: (1997)..(1997)
<223> OTHER INFORMATION: 17-37-811 : polymorphic base A or G
<221> NAME/KEY: allele
<222> LOCATION: (2475)..(2475)
<223> OTHER INFORMATION: 17-38-349 : polymorphic base C or T
```

<400> SEQUENCE: 5

```
attctgactg cagtctgtgg ttctgattcc ataccagagg ggctcagg atg ctg ttg      57
                                               Met Leu Leu
                                                 1 ctg gga gct gtt cta ctg cta tta gct ctg ccc ggk cat gac cag gaa     105
Leu Gly Ala Val Leu Leu Leu Leu Ala Leu Pro Xaa His Asp Gln Glu
  5                  10                  15 acc acg act caa ggg ccc gga gtc ctg ctt ccc ctg ccc aag ggg gcc     153
Thr Thr Thr Gln Gly Pro Gly Val Leu Leu Pro Leu Pro Lys Gly Ala
 20                  25                  30                  35 tgc aca ggt tgg atg gcg ggc atc cca ggg cat ccg gcc ata atg ggg     201
Cys Thr Gly Trp Met Ala Gly Ile Pro Gly His Pro Gly His Asn Gly
                 40                  45                  50 gcc cca ggc cgt gat ggc aga gat ggc acc cct ggt gag aag ggt gag     249
Ala Pro Gly Arg Asp Gly Arg Asp Gly Thr Pro Gly Glu Lys Gly Glu
             55                  60                  65
```

```
aaa gga gat cca ggt ctt att ggt cct aag gga gac atc ggt gaa acc      297
Lys Gly Asp Pro Gly Leu Ile Gly Pro Lys Gly Asp Ile Gly Glu Thr
         70                  75                  80 gga gta ccc ggg gct gaa ggt ccc cga ggc ttt ccg gga atc caa ggc      345
Gly Val Pro Gly Ala Glu Gly Pro Arg Gly Phe Pro Gly Ile Gln Gly
     85                  90                  95 agg aaa gga gaa cct gga gaa ggt gcc tat gta tac cgc tca gca ttc      393
Arg Lys Gly Glu Pro Gly Glu Gly Ala Tyr Val Tyr Arg Ser Ala Phe
100                 105                 110                 115 agt gtg gga ttg gag act tac gtt act atc ccc aac atg ccc att cgc      441
Ser Val Gly Leu Glu Thr Tyr Val Thr Ile Pro Asn Met Pro Ile Arg
                120                 125                 130 ttt acc aag atc ttc tac aat cag caa aac cac tat gat ggc tcc act      489
Phe Thr Lys Ile Phe Tyr Asn Gln Gln Asn His Tyr Asp Gly Ser Thr
            135                 140                 145 ggt aaa ttc cac tgc aac att cct ggg ctg tac tac ttt gcc tac cac      537
Gly Lys Phe His Cys Asn Ile Pro Gly Leu Tyr Tyr Phe Ala Tyr His
        150                 155                 160 atc aca gtc tat atg aag gat gtg aag gtc agc ctc ttc aag aag gac      585
Ile Thr Val Tyr Met Lys Asp Val Lys Val Ser Leu Phe Lys Lys Asp
    165                 170                 175 aag gct atg ctc ttc acc tat gat cag tac cag gaa aat aat gtg gac      633
Lys Ala Met Leu Phe Thr Tyr Asp Gln Tyr Gln Glu Asn Asn Val Asp
180                 185                 190                 195 cag gcc tcc ggc tct gtg ctc ctg cat ctg gag gtg ggc gac caa gtc      681
Gln Ala Ser Gly Ser Val Leu Leu His Leu Glu Val Gly Asp Gln Val
                200                 205                 210 tgg ctc cag gtg tat ggg gaa gga gag cgt aat gga ctc tat gct gat      729
Trp Leu Gln Val Tyr Gly Glu Gly Glu Arg Asn Gly Leu Tyr Ala Asp
            215                 220                 225 aat gac aat gac tcc acc ttc aca ggc ttt ctt ctc tac cat gac acc      777
Asn Asp Asn Asp Ser Thr Phe Thr Gly Phe Leu Leu Tyr His Asp Thr
        230                 235                 240 aac tga tcaccactaa ctcagagcct cctccaggcc aaacagcccc aaagtcaatt       833
Asn aaaggctttc agtacggtta ggaagttgat tattatttag ttggaggcct ttagatatta    893
ttcattcatt tactcattca tttattcatt cattcatcaa gtaactttaa aaaaatcata    953
tgctatgttc ccagtcctgg ggagcttcac aaacatgacc agataactga ctagaaagaa   1013
gtagttgaca gtgctatttt gtgcccactg tctctcctga tgctcatatc aatcctataa   1073
ggcacaggga acaagcattc tcctgttttt acagattgta tcctgaggct gagagagtta   1133
agtgaatgtc taaggtcaca caagtattaa gtgacagtgc tagaaatcaa cccagagct    1193 gtggactttg ttcactagac tgtgcccttt tatagaggta catgttctct ttggagtgtt   1253
ggtaggtgtc tgtttcccac ctcacctgag agccattgaa tttgccttcc tcatgaatta   1313
aaacctcccc caagcagagc ttcctcagag aaagtggttc tatgatgaag tcctgtcttg   1373
gaaggactac tactcaatgg cccctgcact actctacttc ctcttaccta tgtcccttct   1433
catgcctttc cctccaacgg ggaaagccaa ctccatctct aagtgctgaa ctcatccctg   1493
ttcctcaagg ccacctggcc aggagcttct ctgatgtgat atccactttt ttttttttt    1553 gagatggagt ctcactctgt cacccaggct ggagtacagt gacacgacct cggctcactg   1613
cagcctcctt ctcctgggtc caagcaatta ttgtgcctca gcctcccgag tagctgagac   1673
ttcaggtgca ttccaccaca catggctaat ttttgtattt ttagtagaaa tggggtttcg   1733
tcatgttggc caggctggtc tcgaactcct ggcctaggtg atccacccgc ctcgacctcc   1793
```

```
caaagtgctg ggattacagg crtgagccac catgcccagt cgatatctca cttttattt    1853
tgccatggat gagagtcctg ggtgtgagga acacctccca ccaggctaga ggcaactgcc    1913
caggaaggac tgtgcttccg tcacctctaa atcccttgca gatccttgat aaatgcctca    1973
tgaagaccaa tctcttgaat cccrtatcta cccagaatta actccattcc agtctctgca    2033
tgtaatcagt tttatccaca gaaacatttt catttagga atccctggt tttaagtatc      2093
aatccttgtt cagctggaca atatgaatct tttccactga agttagggat gactgtgatt    2153
ttcagaacac gtccagaatt tttcatcaag aaggtagctt gagcctgaaa tgcaaaaccc    2213
atggaggaat tctgaagcca ttgtctcctt gagtaccaac agggtcaggg aagactgggc    2273
ctcctgaatt tattattgtt ctttaagaat tacaggttga ggtagttgat ggtggtaaac    2333
attctctcag gagacaataa ctccagtgat gttcttcaaa gattttagca aaaacagagt    2393
aaatagcatt ctctatcaat atataaattt aaaaaactat cttttttgctt acagttttaa   2453
atcctgaaca attctctctt ayatgtgtat tgctaatcat taaggtatta ttttttccac    2513
atataaagct ttgtcttttt gttgttgttg ttgttttaa gatggagttt ccctctgttg     2573
ccaggctaga gtgcagtggc atgatctcgg cttactgcaa cctttgcctc ccaggttcaa    2633
gcgattcttc tgcctcagcc tcccgagtag ctgggaccac aggtgcctac caccatgcca    2693
ggctaatttt tgtatttta gtaaagacag ggtttcacca tattggccag gctggtctcg     2753
aactcctgac cttgtgatct gcccacctcc atttttgttg ttattttttg agaaagatag    2813
atatgaggtt tagagaggga tgaagaggtg agagtaagcc ttgtgttagt cagaactctg    2873
tgttgtgaat gtcattcaca acagaaaacc caaaatatta tgcaaactac tgtaagcaag    2933
aaaaataaag gaaaaatgga aacatttatt cctttgcata atagaaatta ccagagttgt    2993
tctgtctta gataaggttt gaaccaaagc tcaaaacaat caagacccctt ttctgtatgt    3053
ccttctgttc tgccttccgc agtgtaggct ttaccctcag gtgctacaca gtatagttct    3113
aggggtttccc tcccgatatc aaaaagactg tggcctgccc agctctcgta tccccaagcc   3173
acaccatctg gctaaatgga catcatgttt tctggtgatg cccaaagagg agagaggaag    3233
ctctcttttcc cagatgcccc agcaagtgta accttgcatc tcattgctct ggctgagttg   3293
tgtgcctgtt tctgaccaat cactgagtca ggaggatgaa atattcatat tgacttaatt    3353
gcagcttaag ttaggggtat gtagaggtat tttccctaaa gcaaaattgg gacactgtta    3413
tcagaaatag gagagtggat gatagatgca aaataatacc tgtccacaac aaactcttaa    3473
tgctgtgttt gagctttcat gagtttccca gagagacata gctggaaaat tcctattgat    3533
tttctctaaa atttcaacaa gtagctaaag tctggctatg ctcacagtct cacatctggt    3593
tggggtgggc tccttacaga acacgctttc acagttaccc taaactctct ggggcagggt    3653
tattcctttg tggaaccaga ggcacagaga gagtcaactg aggccaaaag aggcctgaga    3713
gaaactgagg tcaagatttc aggattaatg gtcctgtgat gctttgaagt acaattgtgg    3773
atttgtccaa ttctctttag ttctgtcagc ttttgcttca tatattttag cgctctatta    3833
ttagatatat acatgtttag tattatgtct tattggtgca tttactctct tatcattatg    3893
taatgtcctt ctttatctgt gataattttc tgtgttctga agtctacttt gtctaaaaat    3953
aacatacgca ctcaacttcc ttttctttct tccttccttt ctttcttcct tcctttcttt   4013
ctctctctct ctcttccctt ccttccttcc tccttttctt tctctctctc tctctctctc    4073
ttttttgac agactctcgt tctgtggccc tggctggagt tcagtggtgt gatcttggct     4133
```

-continued

```
cactgctacc tctaccatga gcaattctcc tgcctcagcc tcccaagtag ctggaactac    4193
aggctcatgc cactgcgccc agctaatttt tgtattttc gtagagacgg ggtttcacca    4253
cattcgtcag gttggtttca aactcctgac tttgtgatcc acccgcctcg gcctcccaaa    4313
gtgctgggat tacaggcatg agccatcaca cctggtcaac tttcttttga ttagtgtttt    4373
tgtggtatat cttttcccat catgttactt taaatatatc tatattattg tatttaaaat    4433
gtgtttctta cagactgcat gtagttgggt ataattttta tccagtctaa aaatatctgt    4493
cttttaattg gtgtttagac aatttatatt taataaaatt gttgaattta ag            4545
```

```
<210> SEQ ID NO 6
<211> LENGTH: 244
<212> TYPE: PRT
<213> ORGANISM: Homo sapiens
<220> FEATURE:
<221> NAME/KEY: misc_feature
<222> LOCATION: (15)..(15)
<223> OTHER INFORMATION: The 'Xaa' at location 15 stands for Gly.
<221> NAME/KEY: misc_feature
<222> LOCATION: (1)..(367)
<223> OTHER INFORMATION: homology with 5' EST A254990 in private bank :
      GENSET
<221> NAME/KEY: misc_feature
<222> LOCATION: (91)..(93)
<223> OTHER INFORMATION: Amino acid at position 15 (Xaa) means Gly
<221> NAME/KEY: misc_feature
<222> LOCATION: (15)..(15)
<223> OTHER INFORMATION: The 'Xaa' at location 15 stands for Gly.

<400> SEQUENCE: 6

Met Leu Leu Leu Gly Ala Val Leu Leu Leu Ala Leu Pro Xaa His
1               5                   10                  15

Asp Gln Glu Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
        50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
```

```
225                 230                 235                 240

His Asp Thr Asn

<210> SEQ ID NO 7
<211> LENGTH: 18
<212> TYPE: DNA
<213> ORGANISM: Artificial Sequence
<220> FEATURE:
<223> OTHER INFORMATION: sequencing oligonucleotide PrimerPU

<400> SEQUENCE: 7
tgtaaaacga cggccagt                                                    18

<210> SEQ ID NO 8
<211> LENGTH: 18
<212> TYPE: DNA
<213> ORGANISM: Artificial Sequence
<220> FEATURE:
<223> OTHER INFORMATION: sequencing oligonucleotide PrimerRP

<400> SEQUENCE: 8
caggaaacag ctatgacc                                                    18
```

APM1 BIALLELIC MARKERS AND USES THEREOF

This application claims priority to International Patent Application No. PCT/IB99/01858, filed Nov. 4, 1999 by Dufaure-Gare et al. entitled "Genomic And Complete cDNA Sequences Of APM1 And Biallelic Markers Thereof", and to U.S. Non-provisional patent application Ser. No. 09/434,848, filed Nov. 4, 1999 by Blumenfeld et al. entitled "Genomic And Complete cDNA Sequences Of APM1 And Biallelic Markers Thereof", both of which claim priority to U.S. Provisional Patent Application Ser. No. 60/119,593, filed Feb. 10, 1999, by Blumenfeld et al entitled "Genomic And Complete cDNA Sequences Of APM 1 And Biallelic Markers Thereof", and to U.S. Provisional Patent Application Ser. No. 60/107,113, filed Nov. 4, 1998, by Bougeleret entitled "Genomic And Complete cDNA Sequences Of APM1" all of which are hereby incorporated by reference herein in their entirety including any figures, tables, or drawings.

FIELD OF THE INVENTION

The invention concerns the genomic and cDNA sequences of the APM1 gene, as well as methods and kits for detecting these polynucleotides. The invention also concerns the regulatory regions, particularly the promoter region of the APM1 gene. The invention comprises biallelic markers of the APM1 gene which can be useful for diagnosis of obesity or disorders related to obesity.

BACKGROUND

Obesity is a public health problem that is both serious and widespread. One-third of the population in industrialized countries has an excess weight of at least 20% relative to the ideal weight. The phenomenon continues to worsen, particularly in regions of the globe where economies are modernizing. In the United States, the number of obese people has escalated from 25% at the end of the 70s to 33% at the beginning of the 90s.

Obesity considerably increases the risk of developing cardiovascular and metabolic diseases. It is estimated that if the entire population had an ideal weight, the risk of coronary insufficiency would decrease by 25% and that of cardiac insufficiency and of cerebral vascular accidents by 35%. Coronary insufficiency, atheromatous disease and cardiac insufficiency are at the forefront of the cardiovascular complications induced by obesity. For an excess w eight greater than 30%, the incidence of coronary diseases is doubled in subjects less than 50 years old. Studies carried out for other diseases are equally significant. For an excess weight of 20%, the risk of high blood pressure is doubled. For an excess weight of 30%, the risk of developing non-insulin-dependent diabetes is tripled and the risk of hyperlipidemias is multiplied six fold.

The list of diseases having onsets promoted by obesity is long: hyperuricemia (11.4% in obese subjects, compared with 3.4% in the general population), digestive pathologies, abnormalities in hepatic functions, and even certain cancers.

Whether the physiological changes in obesity are characterized by an increase in the number of adipose cells, or by an increase in the quantity of triglycerides stored in each adipose cell, or by both, this excess weight results mainly from an imbalance between the quantities of calories consumed and the quantity of calories used by the body. Some studies on the causes of this imbalance have focused on studying the mechanism of absorption of foods, and therefore the molecules which control food intake and the feeling of satiety. Other studies have characterized the pathways through which the body uses its calories.

The treatments for obesity which have been proposed are of four types. 1) Food restriction is the most frequently used. Obese individuals are advised to change their dietary habits so as to consume fewer calories. This type of treatment is effective in the short-term. However, the recidivation rate is very high. 2) Increased calorie use through physical exercise is also proposed. This treatment is ineffective when applied alone, but it improves, however, weight-loss in subjects on a low-calorie diet. 3) Gastrointestinal surgery, which reduces the absorption of the calories ingested, is effective but has been virtually abandoned because of the side effects which it causes. 4) The medicinal approach uses either the anorexigenic action of molecules involved at the level of the central nervous system, or the effect of molecules which increase energy use by increasing the production of heat. The prototypes of this kind of molecule are the thyroid hormones that uncouple oxidative phosphorylations of the mitochondrial respiratory chain. The side effects and the toxicity of this type of treatment make their use dangerous. An approach that aims to reduce the absorption of dietary lipids by sequestering them in the lumen of the digestive tube is also in place. However, it induces physiological imbalances that are difficult to tolerate: deficiency in the absorption of fat-soluble vitamins, flatulence and steatorrhoea. Whatever the envisaged therapeutic approach, the treatments of obesity are all characterized by an extremely high recidivation rate.

The molecular mechanisms responsible for obesity in man are complex and involve genetic and environmental factors. Because of the low efficiency of the treatments known up until now, it is urgent to define the genetic mechanisms that determine obesity, so as to be able to develop better targeted medicaments.

More than 20 genes have been studied as possible candidates, either because they have been implicated in diseases of which obesity is one of the clinical manifestations, or because they are homologues of genes involved in obesity in animal models. Situated in the 7q31 chromosomal region, the OB gene is one of the most widely studied. Its product, leptin, is involved in the mechanisms of satiety. Leptin is a plasma protein of 16 kDa produced by the adipocytes under the action of various stimuli. Obese mice of the ob/ob type exhibit a deficiency in the leptin gene; this protein is undetectable in the plasma of these animals. The administration of leptin obtained by genetic engineering to ob/ob mice corrects their relative hyperphagia and allows normalization of their weight. This anorexigenic effect of leptin calls into play a receptor of the central nervous system: the ob receptor which belongs to the family of class 1 cytokine receptors. The ob receptor is deficient in obese mice of the db/db strain. The administration of leptin to these mice has no effect on their food intake and does not allow substantial reduction in their weight. The mechanisms by which the ob receptors transmit the signal for satiety are not precisely known. It is possible that neuropeptide Y is involved in this signaling pathway. It is important to specify at this stage that the ob receptors are not the only regulators of appetite. The Melanocortin 4 receptor is also involved since mice made deficient in this receptor are obese (Gura, (1997)).

The discovery of leptin and the characterization of the leptin receptor at the level of the central nervous system opened a new route for the search for medicaments against obesity. This model, however, rapidly proved disappointing.

Indeed, with only one exception (Montague et al., (1997)), the genes encoding leptin or its ob receptor have proved to be normal in obese human subjects. Furthermore and paradoxically, the plasma concentrations of leptin, the satiety hormone, are abnormally high in most obese human subjects.

Clearly there remains a need for novel medicaments that are useful for reducing body weight in humans. Such pharmaceutical compositions advantageously would help to control obesity and thereby alleviate many of the cardiovascular consequences associated with this condition.

The human adipocyte-specific APM1 gene encodes a secretory protein of the adipose tissue and is likely to play a role in the pathogenesis of obesity. Knowledge of the APM1 genomic sequence, and particularly of both promoter and splice junction sequences, allows the design of novel diagnostics and therapeutic tools that act on lipid metabolism, and are useful for diagnosing and treating obesity disorders.

SUMMARY OF THE INVENTION

The present invention stems from the isolation and characterization of the genomic sequence of APM1 gene including its regulatory regions and of the complete CDNA sequence encoding the APM1 protein. Oligonucleotide probes and primers hybridizing specifically with a genomic sequence of APM1 are also part of the invention. A further object of the invention consists of recombinant vectors comprising any of the nucleic acid sequences described in the present invention, and in particular of recombinant vectors comprising the promoter region of APM1 or a sequence encoding the APM1 protein, as well as cell hosts comprising said nucleic acid sequences or recombinant vectors. The invention also encompasses methods of screening of molecules which modulate or inhibit the expression of the APM1 gene. The invention is also directed to biallelic markers that are located within the APM1 genomic sequence, these biallelic markers representing useful tools in order to identify a statistically significant association between specific alleles of APM1 gene and one or several disorders related to obesity. Further, the invention relates to the use of these biallelic marker associations to indicate people at risk for diseases, including obesity-related diseases, as well as to identify people who would be candidates or non-candidates for a drug treatment, or a clinical trial.

BRIEF DESCRIPTION OF THE FIGURES

FIGS. 3A and 3B are a graphical representation of the effect of APM1 polymorphism on leptin/BMI relationship in obese adolescent girls.

FIGS. 4A and 4B are a graphical representation of the effect of APM1 polymorphism on FFA in obese adolescents girls.

BRIEF DESCRIPTION OF THE SEQUENCES PROVIDED IN THE SEQUENCE LISTING

Figure 1:
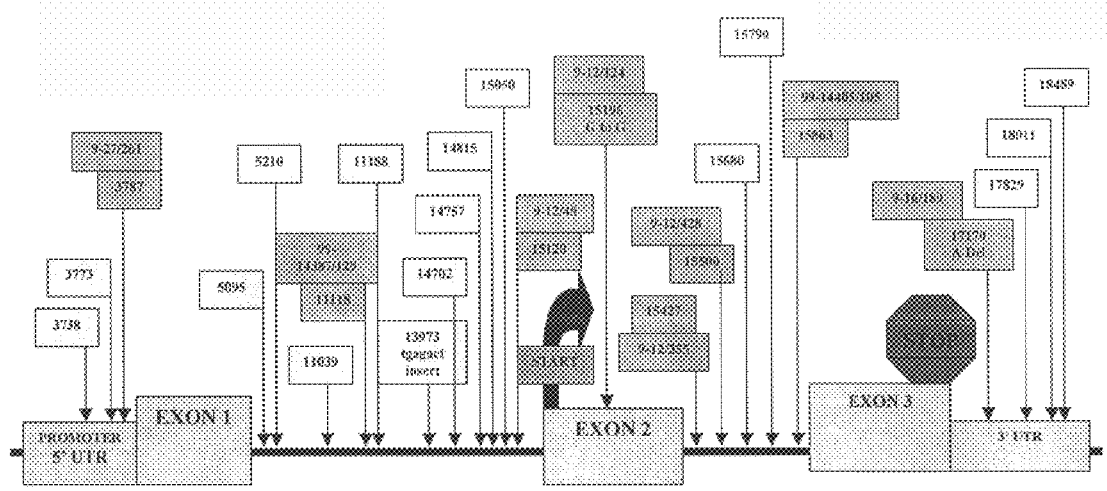
FIG. 1 shows a map of the genomic organization of human Apm1 (Adipose Most Abundant Gene Transcript 1) and the location of the biallelic markers identified in the application.

SEQ ID NO: 1 contains a genomic sequence of APM1 comprising the 5' regulatory region (upstream untranscribed region), the exons and introns, and the 3' regulatory region (downstream untranscribed region).

SEQ ID NO: 2 contains a 5' regulatory region (upstream untranscribed region) of the APM1 gene.

SEQ ID NO: 3 contains a 3' regulatory region (downstream untranscribed region) of the APM1 gene.

SEQ ID NO: 4 contains a partial 5' cDNA of APM1.

SEQ ID NO: 5 contains a complete human APM1 cDNA.

SEQ ID NO: 6 contains the APM1 protein encoded by the cDNA of SEQ ID NO 5.

SEQ ID NO: 7 contains a primer containing the additional PU 5' sequence described further in Example 2.

SEQ ID NO: 8 contains a primer containing the additional RP 5' sequence described further in Example 2.

In accordance with the regulations relating to Sequence Listings, the following codes have been used in the Sequence Listing to indicate the locations of biallelic markers within the sequences and to identify each of the alleles present at the polymorphic base. The code "r" in the sequences indicates that one allele of the polymorphic base is a guanine, while the other allele is an adenine. The code "y" in the sequences indicates that one allele of the polymorphic base is a thymine, while the other allele is a cytosine. The code "m" in the sequences indicates that one allele of the polymorphic base is an adenine, while the other allele is an cytosine. The code "k" in the sequences indicates that one allele of the polymorphic base is a guanine, while the other allele is a thymine. The code "s" in the sequences indicates that one allele of the polymorphic base is a guanine, while the other allele is a cytosine. The code "w" in the sequences indicates that one allele of the polymorphic base is an adenine, while the other allele is an thymine. The nucleotide code of the original allele for each biallelic marker is the following:

| Biallelic marker | Original allele |
| --- | --- |
| 9-27-261 | G |
| 99-14387-129 | A |
| 9-12-48 | T |
| 9-12-124 | T |
| 9-12-355 | G |
| 9-12-428 | A |
| 99-14405-105 | G |
| 17-30-216 | G |
| 9-27-211 | A |
| 9-27-246 | G |
| 17-31-298 | A |
| 17-31-413 | T |
| 17-32-24 | T |
| 99-14387-50 | C |
| 99-14387-199 | A |
| 17-33-TGAGACT | none |

-continued

| Biallelic marker | Original allele |
| --- | --- |
| 17-34-860 | G |
| 17-34-915 | G |
| 17-35-71 | C |
| 17-35-306 | G |
| 17-36-47 | G |
| 17-36-120 | C |
| 17-37-629 | A |
| 17-37-811 | G |
| 17-38-349 | C |

DETAILED DESCRIPTION

The aim of the present invention is to provide polynucleotides derived from the APM1 gene, which are particularly useful to design suitable means for detecting the presence of this gene in a test sample or alternatively the APM1 mRNA molecules that are present in a test sample. The present invention also deals with polynucleotides involved in the expression of the APM1 gene and which can be used for designing means capable of modulating the expression of APM1. Other polynucleotides of the invention are useful to design suitable means to express a desired polynucleotide of interest. The present invention also encompasses biallelic markers of the APM1 gene, and their use, based on biallelic marker association studies, to indicate people at risk for diseases, including obesity-related diseases, as well as to identify people who would be candidates or non-candidates for a drug treatment, or a clinical trial.

Definitions

Before describing the invention in greater detail, the following definitions are set forth to illustrate and define the meaning and scope of the terms used to describe the invention herein.

The term "APM1 gene", when used herein, encompasses genomic, mRNA and cDNA sequences encoding the APM1 protein, including the untranslated regulatory regions of the genomic DNA.

The term "heterologous protein", when used herein, is intended to designate any protein or polypeptide other than the APM1 protein. More particularly, the heterologous protein is a compound which can be used as a marker in further experiments with a APM1 regulatory region.

The term "isolated" requires that the material be removed from its original environment (e. g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

Specifically excluded from the definition of "isolated" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified 5' EST makes up less than 5% of the number of nucleic acid inserts in the vector molecules. Further specifically excluded are whole cell genomic DNA or whole cell RNA preparations (including said whole cell preparations which are mechanically sheared or enzymaticly digested). Further specifically excluded are the above whole cell preparations as either an in vitro preparation or as a heterogeneous mixture separated by electrophoresis (including blot transfers of the same) wherein the polynucleotide of the invention has not further been separated from the heterologous polynucleotides in the electrophoresis medium (e.g., further separating by excising a single band from a heterogeneous band population in an agarose gel or nylon blot).

The term "purified" does not require absolute purity; rather, it is intended as a relative definition. Purification of starting material or natural material to at least one order of magnitude, preferably two or three orders, and more preferably four or five orders of magnitude is expressly contemplated. As an example, purification from 0.1% concentration to 10% concentration is two orders of magnitude.

The term "purified polynucleotide" or "purified polynucleotide vector" is used herein to describe a polynucleotide or polynucleotide vector of the invention which has been separated from other compounds including, but not limited to other nucleic acids, carbohydrates, lipids and proteins (such as the enzymes used in the synthesis of the polynucleotide), or the separation of covalently closed polynucleotides from linear polynucleotides. A polynucleotide is substantially pure when at least about 50%, preferably 60 to 75% of a sample exhibits a single polynucleotide sequence and conformation (linear versus covalently closed). A substantially pure polynucleotide typically comprises about 50%, preferably 60 to 90% weight/weight of a nucleic acid sample, more usually about 95%, and preferably is over about 99% pure. Polynucleotide purity or homogeneity is indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

The term "polypeptide" refers to a polymer of amino without regard to the length of the polymer; thus, peptides, oligopeptides, and proteins are included within the definition of polypeptide. This term also does not specify or exclude post-translation modifications of polypeptides. For example, polypeptides that include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

The term "purified polypeptide" is used herein to describe a polypeptide of the invention that has been separated from other compounds including, but not limited to nucleic acids, lipids, carbohydrates and other proteins. A polypeptide is substantially pure when a sample contains at least about 50%, preferably 60 to 75%, of a single polypeptide sequence. A substantially pure polypeptide typically comprises about 50%, preferably 60 to 90%, more preferably 95 to 99% weight/weight of a protein sample. Polypeptide purity or homogeneity is indicated by a number of means well known in the art, such as agarose or polyacrylamide gel electrophoresis of a sample, followed by visualizing polypeptide bands upon staining the gel. For certain purposes higher resolution can be provided by using HPLC or other means well known in the art.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen., which allows an immunological reaction with the antigen. Antibodies include recombinant proteins comprising the binding domains, as wells as fragments, including Fab, Fab', F(ab)$_2$, and F(ab')$_2$ fragments.

As used herein, an "antigenic determinant" is the portion of an antigen molecule, in this case an APM1 polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8–10 such amino acids. Methods for determining the amino acids which make up an epitope include x-ray crystallography, 2-dimensional nuclear magnetic resonance, and epitope mapping e.g. he Pepscan method described by H. Mario Geysen et al. 1984. Proc. Natl. Acad. Sci. U.S.A. 81:3998–4002; PCT Publication No. WO 84/03564; and PCT Publication No. WO 84/03506.

Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

As used interchangeably herein, the terms "nucleic acids", "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one of the following modifications: (a) an alternative linking group, (b) an analogous form of purine, (c) an analogous form of pyrimidine, or (d) an analogous sugar. For examples of analogous linking groups, purine, pyrimidines, and sugars, see for example PCT publication No. WO 95/04064. The polynucleotide sequences of the invention may be prepared by any known method, including synthetic, recombinant, ex vivo generation, or a combination thereof, as well as utilizing any purification methods known in the art.

A "promoter" refers to a DNA sequence recognized by the synthetic machinery of the cell required to initiate the specific transcription of a gene.

A sequence which is "operably linked" to a regulatory sequence such as a promoter means that said regulatory element is in the correct location and orientation in relation to the nucleic acid to control RNA polymerase initiation and expression of the nucleic acid of interest. As used herein, the term "operably linked" refers to a linkage of polynucleotide elements in a functional relationship. For instance, a promoter or enhancer is operably linked to a coding sequence if it affects the transcription of the coding sequence. More precisely, two DNA molecules (such as a polynucleotide containing a promoter region and a polynucleotide encoding a desired polypeptide or polynucleotide) are said to be "operably linked" if the nature of the linkage between the two polynucleotides does not (1) result in the introduction of a frame-shift mutation or (2) interfere with the ability of the polynucleotide containing the promoter to direct the transcription of the coding polynucleotide.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., polynucleotide as defined hereinbelow) which can be used to identify a specific polynucleotide sequence present in samples, said nucleic acid segment comprising a nucleotide sequence complementary to the specific polynucleotide sequence to be identified.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to, either obesity or disorders related to obesity, more particularly atherosclerosis, insulin resistance, hypertension, hyperlipidemia, hypertriglyceridemia, cardiovascular disease, microangiopathic in obese individuals with Type II diabetes, ocular lesions associated with microangiopathy in obese individuals with Type II diabetes, renal lesions associated with microangiopathy in obese individuals with Type II diabetes, and Syndrome X.

The term "allele" is used herein to refer to variants of a nucleotide sequence. A biallelic polymorphism has two forms. Typically the first identified allele is designated as the original allele whereas other alleles are designated as alternative alleles. Diploid organisms maybe homozygous or heterozygous for an allelic form.

The term "heterozygosity rate" is used herein to refer to the incidence of individuals in a population which are heterozygous at a particular allele. In a biallelic system, the heterozygosity rate is on average equal to $2P_a(1-P_a)$, where $P_a$ is the frequency of the least common allele. In order to be useful in genetic studies, a genetic marker should have an adequate level of heterozygosity to allow a reasonable probability that a randomly selected person will be heterozygous.

The term "genotype" as used herein refers to the identity of the alleles present in an individual or a sample. In the context of the present invention, a genotype preferably refers to the description of the biallelic marker alleles present in an individual or a sample. The term "genotyping" a sample or an individual for a biallelic marker consists of determining the specific allele or the specific nucleotide carried by an individual at a biallelic marker.

The term "mutation" as used herein refers to a difference in DNA sequence between or among different genomes or individuals which has a frequency below 1%.

The term "haplotype" refers to a combination of alleles present in an individual or a sample. In the context of the present invention, a haplotype preferably refers to a combination of biallelic marker alleles found in a given individual and which may be associated with a phenotype.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is the replacement of one nucleotide by another nucleotide at the polymorphic site. Deletion of a single nucleotide or insertion of a single nucleotide also gives rise to single nucleotide polymorphisms. In the context of the present invention, "single nucleotide polymorphism" preferably refers to a single nucleotide substitution. Typically, between different individuals, the polymorphic site may be occupied by two different nucleotides.

The term "biallelic polymorphism" and "biallelic marker" are used interchangeably herein to refer to a single nucleotide polymorphism having two alleles at a fairly high frequency in the population. A "biallelic marker allele" refers to the nucleotide variants present at a biallelic marker site. Typically, the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker".

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on. For polymorphisms which involve the substitution, insertion or deletion of 1 or more nucleotides, the polymorphism, allele or biallelic marker is "at the center" of a polynucleotide if the difference between the distance from the substituted, inserted, or deleted polynucleotides of the polymorphism and the 3' end of the polynucleotide, and the distance from the substituted, inserted, or deleted polynucleotides of the polymorphism and the 5' end of the polynucleotide is zero or one nucleotide. If this difference is 0 to 3, then the polymorphism is considered to be "within 1 nucleotide of the center." If the difference is 0 to 5, the polymorphism is considered to be "within 2 nucleotides of the center." If the difference is 0 to 7, the polymorphism is considered to be "within 3 nucleotides of the center," and so on.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See Stryer, L., *Biochemistry*, $4^{th}$ edition, 1995).

The terms "complementary" or "complement thereof" are used herein to refer to the sequences of polynucleotides that are capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind.

The term "non-genic" is used herein to describe APM1-related biallelic markers, as well as polynucleotides and primers which occur outside the nucleotide positions shown in the human APM1 genomic sequence of SEQ ID NO: 1. The term "genic" is used herein to describe APM1-related biallelic markers as well as polynucleotides and primers which do occur in the nucleotide positions shown in the human APM1 genomic sequence of SEQ ID NO: 1.

Variants and Fragments

The invention also relates to variants and fragments of the polynucleotides described herein, particularly of a APM1 gene containing one or more biallelic markers according to the invention.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Variants of polynucleotides according to the invention include, without being limited to, nucleotide sequences which are at least 95% identical to a polynucleotide selected from the group consisting of SEQ ID Nos 1–4, or to any polynucleotide fragment of at least 8 consecutive nucleotides of a polynucleotide selected from the group consisting of SEQ ID Nos 1–3, and preferably at least 99% identical, more preferably at least 99.5% identical, and most preferably at least 99.8% identical to a polynucleotide selected from the group consisting of SEQ ID Nos 1–5 or to any polynucleotide fragment of at least 8 consecutive nucleotides of a polynucleotide selected from the group consisting of SEQ ID Nos 1–3.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides that increase or retain substantially the same biological function or activity as the mature APM1 protein, or those in which the polynucleotides encode polypeptides that maintain or increase a particular biological activity, while reducing or maintaining a second biological activity.

A polynucleotide fragment is a polynucleotide having a sequence that is entirely the same as part but not all of a given nucleotide sequence, preferably the nucleotide sequence of a APM1 gene, and variants thereof. The fragment can be a portion of an intron of a APM1 gene. It can also be a portion of the regulatory regions of APM1, preferably of the promoter sequence of the APM1 gene. Preferably, such fragments comprise at least one of the biallelic markers A1 to A26 or the complements thereto or a biallelic marker in linkage disequilibrium with one or more of the biallelic markers A1 to A26.

Such fragments may be "free-standing", i.e. not part of or fused to other polynucleotides, or they may be comprised within a single larger polynucleotide of which they form a part or region. Indeed, several of these fragments may be present within a single larger polynucleotide.

Optionally, such fragments may consist of, or consist essentially of a contiguous span of at least 8, 10, 12, 15, 18, 20, 25, 35, 40, 50, 70, 80, 100, 250, 500 or 1000 nucleotides in length. A set of preferred fragments contain at least one of the biallelic markers A1 to A26 of the APM1 gene which are described herein or the complements thereto.

Identity between Nucleic Acids Or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions, although gaps may result where the other sequence contains additions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444–2448; Altschul et al., 1990, J. Mol. Biol. 215(3):403–410; Thompson et al., 1994, Nucleic Acids Res. 22(2):4673–4680; Higgins et al., 1996, Methods Enzymol. 266:383–402; Altschul et al., 1990, J. Mol. Biol. 215(3):403–410; Altschul et al., 1993, Nature Genetics 3:266–272). In a particularly preferred embodiment, protein and nucleic acid sequence homologies are evaluated using the Basic Local Alignment Search Tool ("BLAST") which is well known in the art (see, e.g., Karlin and Altschul, 1990, Proc. Natl. Acad. Sci. USA 87:2267–2268; Altschul et al., 1990, J. Mol. Biol. 215:403–410; Altschul et al., 1993, Nature Genetics 3:266–272; Altschul et al., 1997, Nuc. Acids Res. 25:3389–3402). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992, Science 256:1443–1445; Henikoff and Henikoff, 1993, Proteins 17:49–61). Less preferably, the PAM or PAM250 matrices may also be used (see, e.g., Schwartz and Dayhoff, eds., 1978, Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990, Proc. Natl. Acad. Sci. USA 87:2267–2268).

Stringent Hybridization Conditions

By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA.

Filters are hybridized for 48 h at 65° C., the preferred hybridization temperature, in prehybridization mixture containing 100 μg/ml denatured salmon sperm DNA and 5–20× $10^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989; and Ausubel et al., 1989, are incorporated herein in their entirety. These hybridization conditions are suitable for a nucleic acid molecule of about 20 nucleotides in length. The hybridization conditions described above are adapted according to the length of the desired nucleic acid, following techniques well known to the one skilled in the art. Hybridization conditions may, for example, be adapted according to the teachings disclosed in the book of Hames and Higgins (1985) or in Sambrook et al.( 1989).

Genomic Sequences of APM1

The present invention concerns the genomic sequence of APM1. The present invention encompasses polynucleotides, APM1 genes, or APM1 genomic sequences consisting of, consisting essentially of, or comprising the sequence of SEQ ID No 1, a sequence complementary thereto, as well as fragments and variants thereof. These polynucleotides may be purified, isolated, or recombinant. This genomic sequence of APM1 has been localized on locus 3p27 by FISH.

The invention also encompasses purified, isolated, or recombinant polynucleotides comprising a nucleotide sequence having at least 70, 75, 80, 85, 90, or 95% nucleotide identity with a nucleotide sequence of SEQ ID No 1 or a complementary sequence thereto or a fragment thereof. The nucleotide differences as regards to the nucleotide sequence of SEQ ID No 1 may be generally randomly distributed throughout the entire nucleic acid. Nevertheless, preferred nucleic acids are those wherein the nucleotide differences as regards to the nucleotide sequence of SEQ ID No 1 are predominantly located outside the coding sequences contained in the exons. These nucleic acids, as well as their fragments and variants, may be used as oligonucleotide primers or probes in order to detect the presence of a copy of the APM1 gene in a test sample, or alternatively in order to amplify a target nucleotide sequence within the APM1 sequences.

Another object of the invention consists of a purified, isolated, or recombinant nucleic acids that hybridizes with the nucleotide sequence of SEQ ID No 1 or a complementary sequence thereto or a variant thereof, under the stringent hybridization conditions as defined above.

Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises at least 1, 2, 3, 5, or 10 of the following nucleotide positions of SEQ ID No 1: 1 to 3528, 4852 to 15143, 15366 to 16276, and 20560 to 20966. Other preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises positions 4150 to 4154, or 17169 to 17170 of SEQ ID No: 1. Additional preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises a G at position 3787, a G at position 3809, a T at position 4311, an A at position 4328, an A at position 4683, or an A at position 15319 of SEQ ID No: 1. Additional preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises a G at position 15196, a deletion of an A at position 17170, a G at position 17829, an A at position 18011, and a T at position 18489. It should be noted that nucleic acid fragments of any size and sequence may also be comprised by the polynucleotides described in this section. Other particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises at least 1, 2, 3, 5, or 10 of nucleotide positions 1 to 4833 of SEQ ID No 1.

The APM1 genomic nucleic acid comprises 3 exons. Exon 1 starts at the nucleotide in position 4812 and ends at the nucleotide in position 4851 of the nucleotide sequence of SEQ ID No 1; Exon 2 starts at the nucleotide in position 15144 and ends at the nucleotide in position 15365 of the nucleotide sequence of SEQ ID No 1; Exon 3 starts at the nucleotide in position 16277 and ends at the nucleotide in position 20559 of the nucleotide sequence of SEQ ID No 1. Thus, the invention embodies purified, isolated, or recombinant polynucleotides comprising a nucleotide sequence selected from the group consisting of the three exons of the APM1 gene, or a sequence complementary thereto. The invention also deals with purified, isolated, or recombinant nucleic acids comprising a combination of at least two exons of the APM1 gene, wherein the polynucleotides are arranged within the nucleic acid, from the 5'-end to the 3'-end of said nucleic acid, in the same order as in SEQ ID No 1.

Intron 1 (nucleotide sequence located between Exon 1 and Exon 2) starts at the nucleotide in position 4852 of the nucleotide sequence of SEQ ID No 1 and ends at the nucleotide in position 15143 of the nucleotide sequence of SEQ ID No 1; Intron 2 (nucleotide sequence located between Exon 2 and Exon 3) starts at the nucleotide in position 15366 and ends at the nucleotide in position 16276 of the nucleotide sequence of SEQ ID No 1. Thus, the invention embodies purified, isolated, or recombinant polynucleotides comprising a nucleotide sequence selected from the group consisting of Intron 1 and Intron 2 of the APM1 gene, and sequences complementary thereto.

While this section is entitled "Genomic Sequences of APM1," it should be noted that nucleic acid fragments of any size and sequence may also be comprised by the polynucleotides described in this section, including those flanking the genomic sequences of APM1 on either side and/or between two or more such genomic sequences.

APM1 cDNA Sequences

The expression of the APM1 gene has been shown to lead to the production of at least one mRNA species with the nucleic acid sequence set forth in SEQ ID No 5.

Another object of the invention is a purified, isolated, or recombinant nucleic acid comprising the nucleotide sequence of SEQ ID No 5, complementary sequences thereto, as well as allelic variants, and fragments thereof. Moreover, preferred polynucleotides of the invention include purified, isolated, or recombinant APM1 cDNAs consisting of, consisting essentially of, or comprising the sequence of SEQ ID No: 5. Particularly preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 5 or the complements thereof, wherein said contiguous span comprises positions selected from the group consisting of a nucleotide T at the position 93, positions 1154–1157, a nucleotide G at the position 1997, positions 2083–2086, a nucleotide C at the position 2367, 2456, 2467, 2475, or 2631, an nucleotide A at the position 2778, positions 2785–2788, positions 2797–2801, a nucleotide T at the position 3594, a nucleotide G at the position 3684, positions 3697–3701, positions 4026–4027, a nucleotide T at the position 4053, 4078, 4533 or 4536 of SEQ ID No 5. Alternative preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 5 or the complements thereof, wherein said contiguous span comprises positions selected from the group consisting of a nucleotide G at the position 93, a nucleotide G at the position 1815, a nucleotide A at the position 1997, and a nucleotide T at position 2475 of SEQ ID NO:5. Additional particularly preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 5 or the complements thereof, wherein said contiguous span comprises at least 1, 2, 3, 5, or 10 of nucleotide positions 1 to 22 of SEQ ID No 5.

The cDNA of SEQ ID No 5 includes a 5'-UTR region starting from the nucleotide at position 1 and ending at the nucleotide in position 48 of SEQ ID No 5. The cDNA of SEQ ID No 5 includes a 3'-UTR region starting from the nucleotide at position 785 and ending at the nucleotide at position 4545 of SEQ ID No 5. At least two polyadenylation sites are present at position 2937 to 2942 and position 4525 to 4530 of SEQ ID No 5.

Consequently, the invention concerns a purified, isolated, and recombinant nucleic acids comprising a nucleotide sequence of the 5'UTR of the APM1 cDNA, a sequence complementary thereto, or an allelic variant thereof.

The sequence at the 5'-end of this cDNA, more particularly the nucleotide sequence comprising 1 to 367 of SEQ ID No 5, corresponds to the nucleotide sequence of a 5'-EST that was obtained from a human dystrophic muscle cDNA library, and characterized following the teachings of the PCT Application No WO 96/34981 and of the U.S. patent application Ser. No. 08/905,134 filed on Aug. 1, 1997. Polynucleotides comprising this 5'-EST are also part of the invention. This 5' EST is set forth in SEQ ID No 4.

While this section is entitled "APM1 cDNA Sequences," it should be noted that nucleic acid fragments of any size and sequence may also be comprised by the polynucleotides described in this section, including those flanking the genomic sequences of APM1 and/or between two or more such genomic sequences.

Regulatory Sequences of APM1

The genomic sequence of the APM1 gene contains regulatory sequences both in the non-coding 5'-flanking region and in the non-coding 3'-flanking region that border the APM1 coding region containing the three exons of this gene, as well as in the introns.

The 5'-regulatory sequence of the APM1 gene comprises the nucleotide sequence of SEQ ID No 2, and from 1 to 4811 of SEQ ID No 1. This polynucleotide contains the promoter site.

The 3'-regulatory sequence of the APM1 gene comprises the nucleotide sequence of SEQ ID No 3, and from 20560 to 20966 of SEQ ID No 1.

Polynucleotides derived from the SEQ ID Nos 2 or 3 are useful in order to detect the presence of at least a copy of a nucleotide sequence of SEQ ID No 1 or a fragment thereof in a test sample. They are also useful to express APM1 or a heterologous protein in cells.

The promoter activity of the regulatory regions of APM1 can be assessed as described below.

Methods to identify relevant biologically active polynucleotide fragments or variants of SEQ ID Nos 2 and 3, are known to one with skill in the art, and exemplary methods are described in Sambrook et al.(Sambrook, 1989). For example, the presence of a promoter (or other regulatory sequences) in test sequences can be determined by splicing the test sequences (fragments or variants of SEQ ID Nos 2 and 3, for example) into a recombinant vector carrying a marker gene (i.e. beta galactosidase, chloramphenicol acetyl transferase, etc.) that is expressed only if a promoter (or other regulatory sequences) is present in the test sequences. Genomic sequences located upstream of the first exon of the APM1 gene can be cloned into a suitable promoter reporter vector, such as the pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, β galactosidase, or green fluorescent protein. The sequences upstream from the APM1 coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

A promoter sequence within the upstream genomic DNA may be further defined by constructing nested 5' and/or 3' deletions in the upstream DNA using conventional techniques such as Exonuclease III or appropriate restriction endonuclease digestion. The resulting deletion fragments can be inserted into the promoter reporter vector to determine whether the deletion has reduced or obliterated promoter activity, such as described, for example, by Coles et al.(1998). In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. This type of assay is well-known to those skilled in the art and is described in WO 97/17359, U.S. Pat. No. 5,374,544, EP 582 796, U.S. Pat. Nos. 5,698,389, 5,643,746, 5,502,176, and 5,266,488, incorporated herein by reference in their entirety including any drawings, figures, or tables.

The strength and the specificity of the promoter of the APM1 gene can be assessed through the expression levels of a detectable polynucleotide operably linked to the APM1 promoter in different types of cells and tissues. The detectable polynucleotide may be either a polynucleotide that specifically hybridizes with a predefined oligonucleotide probe, or a polynucleotide encoding a detectable protein, including a APM1 polypeptide or a fragment or a variant thereof. This type of assay is well-known to those skilled in the art and is described in U.S. Pat. Nos. 5,502,176, and 5,266,488, incorporated herein by reference in their entirety including any drawings, figures, or tables. In addition, some of the methods are discussed in more detail below.

Polynucleotides carrying the regulatory elements located at the 5' end and at the 3' end of the APM1 coding region may be advantageously used to control the transcriptional and translational activity of an heterologous polynucleotide of interest.

Thus, the present invention also concerns a purified or isolated nucleic acid comprising a polynucleotide which is selected from the group consisting of the nucleotide sequences of SEQ ID Nos 2 and 3, or a sequence complementary thereto or a biologically active fragment or variant thereof.

The invention also pertains to a purified or isolated nucleic acid comprising a polynucleotide having at least 95% nucleotide identity with a polynucleotide selected from the group consisting of the nucleotide sequences of SEQ ID Nos 2 and 3, advantageously 99% nucleotide identity, preferably 99.5% nucleotide identity and most preferably 99.8% nucleotide identity with a polynucleotide selected from the group consisting of the nucleotide sequences of SEQ ID Nos 2 and 3, or a sequence complementary thereto or a variant thereof or a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of SEQ ID Nos 2 and 3, or a sequence complementary thereto or a variant thereof or a biologically active fragment thereof.

Preferred fragments of the nucleic acid of SEQ ID No 2 have a length of about 1500 or 1000 nucleotides, preferably of about 500 nucleotides, more preferably about 400 nucleotides, even more preferably 300 nucleotides and most preferably about 200 nucleotides. Preferably the fragments of SEQ ID No 2 are within positions 1 to 3528.

Preferred fragments of the nucleic acid of SEQ ID No 3 are at least 50, 100, 150, 200, 300 or 400 bases in length.

By "biologically active" polynucleotide derivatives of SEQ ID Nos 1, 2 and 3 are polynucleotides comprising or alternatively consisting of a fragment of said polynucleotide which is functional as a regulatory region for expressing a recombinant polypeptide or a recombinant polynucleotide in a recombinant cell host. It could act either as an enhancer or as a repressor.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

The regulatory polynucleotides of the invention may be prepared from any of the nucleotide sequence of SEQ ID Nos 1, 2, and 3 by cleavage using suitable restriction enzymes, as described for example in Sambrook et al. (1989).

The regulatory polynucleotides may also be prepared by digestion of any of SEQ ID Nos 1, 2, and 3 by an exonuclease enzyme, such as Bal31 (Wabiko et al., 1986).

These regulatory polynucleotides can also be prepared by nucleic acid chemical synthesis, as described elsewhere in the specification.

The regulatory polynucleotides according to the invention may be part of a recombinant expression vector that may be used to express a coding sequence in a desired host cell or host organism. The recombinant expression vectors according to the invention are described elsewhere in the specification.

A preferred 5'-regulatory polynucleotide of the invention includes the 5'-untranslated region (5'-UTR) of the APM1 cDNA, or a biologically active fragment or variant thereof.

A preferred 3'-regulatory polynucleotide of the invention includes the 3'-untranslated region (3'-UTR) of the APM1 cDNA, or a biologically active fragment or variant thereof.

A further object of the invention consists of a purified or isolated nucleic acid comprising:

a) a nucleic acid comprising a regulatory nucleotide sequence selected from the group consisting of:
  (i) a nucleotide sequence comprising a polynucleotide of SEQ ID No 2 or a complementary sequence thereto;
  (ii) a nucleotide sequence comprising a polynucleotide having at least 95% of nucleotide identity with the nucleotide sequence of SEQ ID No 2 or a complementary sequence thereto;
  (iii) a nucleotide sequence comprising a polynucleotide that hybridizes under stringent hybridization conditions with the nucleotide sequence of SEQ ID No 2 or a complementary sequence thereto; and
  (iv) a biologically active fragment or variant of the polynucleotides in (i), (ii) and (iii);

b) a polynucleotide encoding a desired polypeptide or a nucleic acid of interest, operably linked to the nucleic acid defined in (a) above;

c) Optionally, a nucleic acid comprising a 3'-regulatory polynucleotide, preferably a 3'-regulatory polynucleotide of the APM1 gene.

In a specific embodiment of the nucleic acid defined above, said nucleic acid includes the 5'-untranslated region (5'-UTR) of the APM1 cDNA, or a biologically active fragment or variant thereof.

In a second specific embodiment of the nucleic acid defined above, said nucleic acid includes the 3'-untranslated region (3'-UTR) of the APM1 cDNA, or a biologically active fragment or variant thereof.

The regulatory polynucleotide of SEQ ID No 2, and its biologically active fragments or variants, is operably linked at the 5'-end of the polynucleotide encoding the desired polypeptide or polynucleotide.

The regulatory polynucleotide of SEQ ID No 3, or its biologically active fragments or variants, is advantageously operably linked at the 3'-end of the polynucleotide encoding the desired polypeptide or polynucleotide.

The desired polypeptide encoded by the above-described nucleic acid may be of various nature or origin, encompassing proteins of prokaryotic or eukaryotic origin. Among the polypeptides expressed under the control of a APM1 regulatory region are included bacterial, fungal or viral antigens. Also encompassed are eukaryotic proteins including, but not limited to, intracellular proteins such as "house keeping" proteins, membrane-bound proteins such as receptors, and secreted proteins such as endogenous mediators, for example cytokines. The desired polypeptide may be the APM1 protein, especially the protein of the amino acid sequence of SEQ ID No 6, or a fragment or a variant thereof.

The nucleic acids encoded by the above-described polynucleotide, usually an RNA molecule, may be complementary to a coding polynucleotide, for example to the APM1 coding sequence, and thus useful as antisense polynucleotides.

Such a polynucleotide may be included in a recombinant expression vector in order to express the desired polypeptide or the desired nucleic acid in host cell or in a host organism. Suitable recombinant vectors that contain a polynucleotide such as described hereinbefore are disclosed elsewhere in the specification.

Coding Regions

The APM1 open reading frame is contained in the corresponding mRNA of SEQ ID No 5. More precisely, the effective APM1 coding sequence (CDS) includes the region between nucleotide position 49 (first nucleotide of the ATG codon) and nucleotide position 783 (end nucleotide of the TGA codon) of SEQ ID No 5. The present invention also embodies isolated, purified, and recombinant polynucleotides which encode polypeptides comprising a contiguous span of at least 6 amino acids, preferably at least 8 or 10 amino acids, more preferably at least 12, 15, 20, 25, 30, 40, 50, or 100 amino acids of SEQ ID NO: 6, wherein said contiguous span includes a glutamic acid residue at amino acid position 56 in SEQ ID NO: 6.

The coding sequence of APM1 may be expressed in a desired host cell or a desired host organism, when this polynucleotide is placed under the control of suitable expression signals. The expression signals may be either the expression signals contained in the regulatory regions in the APM1 gene of the invention or may be exogenous regulatory nucleic sequences. Such a polynucleotide, when placed under suitable expression signals, may also be inserted in a vector for its expression and/or amplification.

Polynucleotide Constructs

The terms "polynucleotide construct" and "recombinant polynucleotide" are used interchangeably herein to refer to linear or circular, purified or isolated polynucleotides that have been artificially designed and which comprise at least two nucleotide sequences that are not found as contiguous nucleotide sequences in their initial natural environment.

DNA Construct that Enables Directing Temporal and Spatial APM1 Gene Expression in Recombinant Cell Hosts and in Transgenic Animals In order to study the physiological and phenotypic consequences of a lack of synthesis of the APM1 protein, both at the cell level and at the multi cellular organism level, the invention also encompasses DNA constructs and recombinant vectors enabling a conditional expression of a specific allele of the APM1 genomic sequence or cDNA and also of a copy of this genomic sequence or cDNA harboring substitutions, deletions, or additions of one or more bases as regards to the APM1 nucleotide sequence of SEQ ID Nos 1 and 5, or a fragment thereof, these base substitutions, deletions or additions being located either in an exon, an intron or a regulatory sequence, but preferably in the 5'-regulatory sequence or in an exon of the APM1 genomic sequence or within the APM1 cDNA of SEQ ID No 5. In a preferred embodiment, the APM1 sequence comprises a biallelic marker of the present invention.

The present invention also embodies recombinant vectors comprised of isolated, purified, or recombinant polynucleotides which encode a polypeptides comprising a contiguous span of at least 6 amino acids, preferably at least 8 or 10 amino acids, more preferably at least 12, 15, 20, 25, 30, 40, 50, or 100 amino acids of SEQ ID NO: 6, wherein said contiguous span includes a glutamic acid residue at amino acid position 56 in SEQ ID NO: 6. Particularly preferred embodiments of the invention include recombinant vectors comprised of isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 5 or the complements thereof, wherein said contiguous span comprises positions selected from the group consisting of a nucleotide T at the position 93, positions 1154–1157, a nucleotide G at the position 1997, positions 2083–2086, a nucleotide C at the position 2367, 2456, 2467, 2475, or 2631, an nucleotide A at the position 2778, positions 2785–2788, positions 2797–2801, a nucleotide T at the position 3594, a nucleotide G at the position 3684, positions 3697–3701, positions 4026–4027, a nucleotide T at the position 4053, 4078, 4533 or 4536 of SEQ ID No 5. Alternative preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 5 or the complements thereof, wherein said contiguous span comprises positions selected from the group consisting of a nucleotide G at the position 93, a nucleotide G at the position 1815, a nucleotide A at the position 1997, and a nucleotide T at position 2475 of SEQ ID NO:5. Other particularly preferred embodiments of the invention include recombinant vectors comprised of isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 5 or the complements thereof, wherein said contiguous span comprises at least 1, 2, 3, 5, or 10 of nucleotide positions 1 to 22 of SEQ ID No 5. Such embodiments are particularly useful in expression vectors, and when stably transfected into host cells and animals. Particularly preferred recombinant vectors of the invention are comprised of isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises at least 1, 2, 3, 5, or 10 of the following nucleotide positions of SEQ ID No 1:1 to 3528, 4852 to 15143, 15366 to 16276, and 20560 to 20966. Other preferred, recombinant vectors of the invention are comprised of isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises positions 4150 to 4154, or 17169 to 17170 of SEQ ID No: 1. Additional preferred recombinant vectors of the invention are comprised of isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises a G at position 3787, a G at position 3809, a T at position 4311, an A at position 4328, an A at position 4683, or an A at position 15319 of SEQ ID No: 1. Other particularly preferred recombinant vectors of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises at least 1, 2, 3, 5, or 10 of nucleotide positions 1 to 4833 of SEQ ID No 1.

A first preferred DNA construct is based on the tetracycline resistance operon tet from *E. coli* transposon Tn110 for controlling the APM1 gene expression, such as described by Gossen et al.(1992, 1995) and Furth et al.(1994). Such a DNA construct contains seven tet operator sequences from Tn10 (tetop) that are fused to either a minimal promoter or a 5'-regulatory sequence of the APM1 gene, said minimal promoter or said APM1 regulatory sequence being operably linked to a polynucleotide of interest that codes either for a sense or an antisense oligonucleotide or for a polypeptide, including a APM1 polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP16 of herpes simplex virus, placed under the control of a promoter, such as the HCMVIE1 enhancer/promoter or the MMTV-LTR. Indeed, a preferred DNA construct of the invention comprises both the polynucleotide containing the tet operator sequences and the polynucleotide containing a sequence coding for the tTA or the rTA repressor.

In a specific embodiment, the conditional expression DNA construct contains the sequence encoding the mutant tetracycline repressor rTA, where the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is comprised in the APM1 genomic sequence; (b) a nucleotide sequence comprising a positive selection marker, such as the marker for neomycine resistance (neo); and (c) a second nucleotide sequence that is comprised in the APM1 genomic sequence, and is located downstream from the first APM1 nucleotide sequence (a).

In a preferred embodiment, this DNA construct also comprises a negative selection marker located upstream from the nucleotide sequence (a) or downstream from the nucleotide sequence (c). Preferably, the negative selection marker consists of the thymidine kinase (tk) gene (Thomas et al., 1986), the hygromycin beta gene (Te Riele et al., 1990), the hprt gene (Van der Lugt et al., 1991; Reid et al., 1990) or the Diphteria toxin A fragment (Dt-A) gene (Nada et al., 1993; Yagi et al. 1990). Preferably, the positive selection marker is located within a APM1 exon sequence so as to interrupt the sequence encoding a APM1 protein. These replacement vectors are described, for example, by Thomas et al.(1986; 1987), Mansour et al.(1988) and Koller et al.(1992).

The first and second nucleotide sequences (a) and (c) may be located within a APM1 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb and most preferably from 2 to 4 kb.

DNA Constructs Allowing Homologous Recombination

The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, the a polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell in vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a a polynucleotide construct which alters the expression of a targeted gene in a cell type in which the gene is not normally expressed. This occurs when a polynucleotide construct is inserted into the chromosomal DNA of the target cell, wherein the a polynucleotide construct comprises: a) a targeting sequence; b)

a regulatory sequence and/or coding sequence; and c) an unpaired splice-donor site, if necessary. Further included are a polynucleotide constructs, as described above, wherein the construct further comprises a polynucleotide which encodes a polypeptide and is in-frame with the targeted endogenous gene after homologous recombination with chromosomal DNA.

The compositions may be produced, and methods performed, by techniques known in the art, such as those described in U.S. Pat. Nos: 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos:WO96/29411, WO 94/12650; and scientific articles including 1994; Koller et al., Proc. Natl. Acad. Sci. USA 86:8932–8935 (1989) (the disclosures of each of which are incorporated by reference in their entireties).

DNA Constructs Allowing Homologous Recombination: Cre-LoxP System

These new DNA constructs make use of the site specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence (Hoess et al., 1986). The recombination by the Cre enzyme between two loxP sites having an identical orientation leads to the deletion of the DNA fragment.

The Cre-loxP system used in combination with a homologous recombination technique has been described by Gu et al.(1993, 1994). Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be provided by (a) incubating the recombinant cell hosts in a culture medium containing this enzyme, by injecting the Cre enzyme directly into the desired cell, such as described by Araki et al.(1995), or by lipofection of the enzyme into the cells, such as described by Baubonis et al.(1993); (b) transfecting the cell host with a vector comprising the Cre coding sequence operably linked to a promoter functional in the recombinant cell host, which promoter being optionally inducible, said vector being introduced in the recombinant cell host, such as described by Gu et al.(1993) and Sauer et al.(1988); (c) introducing in the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al.(1994).

In a specific embodiment, the vector containing the sequence to be inserted in the APM1 gene by homologous recombinatlon is constructed in such a way that selectable markers are flanked by loxP sites in the same orientation. The selectable markers can be removed while leaving the APM1 sequences of interest that have been inserted by an homologous recombination event using the Cre enzyme. Again, two selectable markers are needed: a positive selection marker to select for the recombination event and a negative selection marker to select for the homologous recombination event. Vectors and methods using the Cre-loxP system are described by Zou et al.(1994).

Thus, a third preferred DNA construct of the invention comprises, from 5'-end to 3'-end: (a) a first nucleotide sequence that is comprised in the APM1 genomic sequence; (b) a nucleotide sequence comprising a polynucleotide encoding a positive selection marker, said nucleotide sequence comprising additionally two sequences defining a site recognized by a recombinase, such as a loxP site, the two sites being placed in the same orientation; and (c) a second nucleotide sequence that is comprised in the APM1 genomic sequence, and is located on the genome downstream of the first APM1 nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence, and most preferably a promoter sequence which is both inducible and tissue-specific, such as described by Gu et al.(1994).

The presence of the Cre enzyme within the genome of the recombinant cell host may be the result of the breeding of two transgenic animals, the first transgenic animal bearing the APM1-derived sequence of interest containing the loxP sites as described above and the second transgenic animal bearing the Cre coding sequence operably linked to a suitable promoter sequence, such as described by Gu et al.(1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graham (1995) and Kanegae et al.(1995).

The DNA constructs described above may be used to introduce a desired nucleotide sequence of the invention, preferably a APM1 genomic sequence or a APM1 cDNA sequence, and most preferably an altered copy of a APM1 genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination). In a specific embodiment, the DNA constructs described above may be used to introduce a APM1 genomic sequence or a APM1 cDNA sequence comprising at least one biallelic marker of the present invention, preferably at least one biallelic marker selected from the group consisting of A1 to A26.

Nuclear Antisense DNA Constructs

Other compositions contain a vector of the invention comprising an oligonucleotide fragment of the nucleic sequence SEQ ID No 5, preferably a fragment including the start codon of the APM1 gene, as an antisense tool that inhibits the expression of the corresponding APM1 gene. Preferred methods using antisense polynucleotide according to the present invention are described by Sczakiel et al. (1995) or PCT Application No WO 95/24223, hereby encorporated by reference herein in their entirety including any drawings, figures, or tables.

Preferably, the antisense tools are chosen among the polynucleotides (15–200 bp long) that are complementary to the 5' end of the APM1 mRNA. In one embodiment, a combination of different antisense polynucleotides complementary to different parts of the desired targeted gene are used.

Preferred antisense polynucleotides of the invention are complementary to mRNA sequences of APM1 containing either the translation initiation codon ATG or a splice site. Further preferred antisense polynucleotides are complementary to a splice site of APM1 mRNA.

Preferably, the antisense polynucleotides of the invention have a 3' polyadenylation signal that has been replaced with a self-cleaving ribozyme sequence, such that RNA polymerase II transcripts are produced without poly(A) at their 3' ends. These antisense polynucleotides are incapable of being exported from the nucleus (Liu et al. (1994)). In a preferred embodiment, these APM1 antisense polynucleotides also comprise, within the ribozyme cassette, a histone stem-loop structure to stabilize cleaved transcripts against 3'–5' exonucleolytic degradation, such as the structure described by Eckner et al.(1991).

Oligonucleotide Probes and Primers

Polynucleotides derived from the APM1 gene are useful in order to detect the presence of at least a copy of a nucleotide sequence of SEQ ID No 1, or a fragment, complement, or variant thereof in a test sample.

Primers and probes according to the invention consist of nucleic acids comprising at least 12, 15, 18, 20, 25, 30, 40, 50, or 100 consecutive nucleotides of a nucleic acid selected from the group consisting of:

a) the nucleotide sequence beginning at the nucleotide in position 1 and ending at the nucleotide in position 4811 of the nucleotide sequence of SEQ ID No 1 or a variant thereof or a sequence complementary thereto; more particularly, the nucleotide sequence beginning at the nucleotide in position 1 and ending at the nucleotide in position 3528 of the nucleotide sequence of SEQ ID No 1 or a variant thereof or a sequence complementary thereto;

b) the nucleotide sequence beginning at the nucleotide in position 4853 and ending at the nucleotide in position 15143 of the nucleotide sequence of SEQ ID No 1 or a variant thereof or a sequence complementary thereto;

c) the nucleotide sequence beginning at the nucleotide in position 15366 and ending at the nucleotide in position 16276 of the nucleotide sequence of SEQ ID No 1 or a variant thereof or a sequence complementary thereto;

d) the nucleotide sequence beginning at the nucleotide in position 20560 and ending at the nucleotide in position 20966 of the nucleotide sequence of SEQ ID No 1 or a variant thereof or a sequence complementary thereto;

e) the nucleotide sequence beginning at the nucleotide in position 1 and ending at the nucleotide in position 22 of the nucleotide sequence of SEQ ID No 5 or a variant thereof or a sequence complementary thereto.

Thus, the invention also relates to nucleic acid probes characterized in that they hybridize specifically, under the stringent hybridization conditions defined above, with a nucleic acid selected from the group consisting of:

a) the nucleotide sequence beginning at the nucleotide in position 1 and ending at the nucleotide in position 4811 of the nucleotide sequence of SEQ ID No 1 or a variant thereof or a sequence complementary thereto; more particularly, the nucleotide sequence beginning at the nucleotide in position 1 and ending at the nucleotide in position 3528 of the nucleotide sequence of SEQ ID No 1 or a variant thereof or a sequence complementary thereto;

b) the nucleotide sequence beginning at the nucleotide in position 4853 and ending at the nucleotide in position 15143 of the nucleotide sequence of SEQ ID No 1 or a variant thereof or a sequence complementary thereto;

c) the nucleotide sequence beginning at the nucleotide in position 15366 and ending at the nucleotide in position 16276 of the nucleotide sequence of SEQ ID No 1 or a variant thereof or a sequence complementary thereto;

d) the nucleotide sequence beginning at the nucleotide in position 20560 and ending at the nucleotide in position 20966 of the nucleotide sequence of SEQ ID No 1 or a variant thereof or a sequence complementary thereto;

e) the nucleotide sequence beginning at the nucleotide in position 1 and ending at the nucleotide in position 22 of the nucleotide sequence of SEQ ID No 5 or a variant thereof or a sequence complementary thereto.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes of the invention usually ranges between 10 and 75%, preferably between 35 and 60%, and more preferably between 40 and 55%.

A probe or a primer according to the invention has between 8 and 1000 nucleotides in length, and ranges preferably at least 8, 10, 12, 15, 18 or 20 to 25, 35, 40, 50, 60, 70, 80, 100, 250, 500 or 1000 contiguous nucleotides of the nucleotide sequence of SEQ ID Nos 1–3, or a variant thereof or a complementary sequence thereto, or is specified to be at least 12, 15, 18, 20, 25, 35, 40, 50, 60, 70, 80, 100, 250, 500 or 1000 contiguous nucleotides of the nucleotide sequence of SEQ ID Nos 1–3 or a variant thereof or a complementary sequence thereto. More particularly, the length of these probes can range from 8, 10, 15, 20, or 30 to 100 nucleotides, preferably from 10 to 50, more preferably from 15 to 30 nucleotides. Shorter probes tend to lack specificity for a target nucleic acid sequence and generally require cooler temperatures to form sufficiently stable hybrid complexes with the template. Longer probes are expensive to produce and can sometimes self-hybridize to form hairpin structures. The appropriate length for primers and probes under a particular set of assay conditions may be empirically determined by one of skill in the art. A preferred probe or primer consists of a nucleic acid comprising a polynucleotide selected from the group of nucleotide sequences consisting of B1 to B23, C1 to C24, D1 to D26 and E1 to E26.

Additionally, another preferred embodiment of a probe according to the invention consists of a nucleic acid comprising a biallelic marker selected from the group consisting of A1 to A26 or the complements thereto. Exemplary probes are given in Table 4 in the Examples.

Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises at least 1, 2, 3, 5, or 10 of the following nucleotide positions of SEQ ID No 1: 1 to 3528, 4852 to 15143, 15366 to 16276, and 20560 to 20966. Other preferred primers and probes of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises positions 4150 to 4154, or 17169 to 17170 of SEQ ID No: 1. Additional preferred primers and probes of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises a G at position 3787, a G at position 3809, a T at position 4311, an A at position 4328, an A at position 4683, or an A at position 15319 of SEQ ID No: 1. Additional preferred primers and probes of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises a G at position 15196, a deletion of an A at position 17170, a G at position 17829, an A at position 18011, and a T at position 18489. Other particularly preferred primers and probes of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 1 or the complements thereof, wherein said contiguous span comprises at least 1, 2, 3, 5, or 10 of nucleotide positions 1 to 4833 of SEQ ID No 1.

Another object of the invention is a purified, isolated, or recombinant primers and probes comprising the nucleotide sequence of SEQ ID No 5, complementary sequences thereto, as well as allelic variants, and fragments thereof. Moreover, preferred primers and probes of the invention include purified, isolated, or recombinant APM1 cDNAs consisting of, consisting essentially of, or comprising the sequence of SEQ ID No: 5. Particularly preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 5 or the complements thereof, wherein said contiguous span comprises positions selected from the group consisting of a nucleotide T at the position 93, positions 1154–1157, a nucleotide G at the position 1997, positions 2083–2086, a nucleotide C at the position 2367, 2456, 2467, 2475, or 2631, an nucleotide A at the position 2778, positions 2785–2788, positions 2797–2801, a nucleotide T at the position 3594, a nucleotide G at the position 3684, positions 3697–3701, positions 4026–4027, a nucleotide T at the position 4053, 4078, 4533 or 4536 of SEQ ID No 5. Alternative preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 5 or the complements thereof, wherein said contiguous span comprises positions selected from the group consisting of a nucleotide G at the position 93, a nucleotide G at the position 1815, a nucleotide A at the position 1997, and a nucleotide T at position 2475 of SEQ ID NO:5. Other particularly preferred embodiments of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No: 5 or the complements thereof, wherein said contiguous span comprises at least 1, 2, 3, 5, or 10 of nucleotide positions 1 to 22 of SEQ ID No 5.

In one embodiment the invention encompasses isolated, purified, and recombinant polynucleotides consisting of, or consisting essentially of a contiguous span of 8 to 50 nucleotides of SEQ ID 1 and the complement thereof, wherein said span includes an APM1-related biallelic marker in said sequence; optionally, wherein said APM1-related biallelic marker is selected from the group consisting of A1, A2, A3, A5, A6, A7, A9, A10, A11, A12, A13, A14, A15, A16, A17, A18, A19, A20, A21, A22, A23, and A23; optionally, wherein said APM1-related biallelic marker is selected from the group consisting of A4 A8, A24, A25 and A26; optionally, wherein said APM1-related biallelic marker is selected from the group consisting of A1, A2, and A7 or the group consisting of A4 and A8; optionally, wherein said contiguous span is 18 to 35 nucleotides in length and said biallelic marker is within 4 nucleotides of the center of said polynucleotide; optionally, wherein said polynucleotide consists of said contiguous span and said contiguous span is 25 nucleotides in length and said biallelic marker is at the center of said polynucleotide; optionally, wherein the 3' end of said contiguous span is present at the 3' end of said polynucleotide; and optionally, wherein the 3' end of said contiguous span is located at the 3' end of said polynucleotide and said biallelic marker is present at the 3' end of said polynucleotide.

In another embodiment the invention encompasses isolated, purified and recombinant polynucleotides consisting of, or consisting essentially of a contiguous span of 8 to 50 nucleotides of SEQ ID No: 1 or the complement thereof, wherein the 3' end of said contiguous span is located at the 3' end of said polynucleotide, and wherein the 3' end of said polynucleotide is located within 20 nucleotides upstream of an APM1-related biallelic marker in said sequence; optionally, wherein said APM1-related biallelic marker is selected from the group consisting of A1, A2, A3, A5, A6, A7, A9, A10, A11, A12, A13, A14, A15, A16, A17, A18, A19, A20, A21, A22, and A23, or wherein said APM1-related biallelic marker is selected from the group consisting of A4,A8,A24,A25 and A26; optionally, wherein said APM1-related biallelic marker is selected from the group consisting of A1, A2, and A7 or the group consisting of A4 and A8; optionally, wherein the 3' end of said polynucleotide is located 1 nucleotide upstream of said APM1-related biallelic marker in said sequence; and optionally, wherein said polynucleotide consists essentially of a sequence selected from the following sequences: D1, D2, D3, D4, D5, D6, D7, D8, D9, D10, D11, D12, D13, D14, D15, D16, D17, D18, D18, D19, D20, D21, D22, D23, D24, D25, D26, E1, E2, E3, E4, E5, E6, E7, E8, E9, E10, E11, E12, E13, E14, E15, E16, E17, E18, E19, E20, 21, E22, E23, E24, E25, and E26.

In a further embodiment, the invention encompasses isolated, purified, or recombinant polynucleotides consisting of, or consisting essentially of a sequence selected from the following sequences: B1, B2, B3, B4, B5, B6, B7, B8, B9, B10, B11, B12, B13, B14, B15, B16, B17, B18, B19, B 20, B21, B22, B23, C1, C2, C3, C4, C5, C6, C7, C8, C9, C10, C11, C12, C13, C14, C15, C16, C17, C18, C19, C20, C21, C22, C23, and C24.

In an additional embodiment, the invention encompasses polynucleotides for use in hybridization assays, sequencing assays, and allele-specific amplification assays for determining the identity of the nucleotide at an APM1-related biallelic marker in SEQ ID No:1 or the complement thereof, as well as polynucleotides for use in amplifying segments of nucleotides comprising an APM1-related biallelic marker in SEQ ID No:1 or the complement thereof, optionally, wherein said APM1-related biallelic marker is selected from the group consisting of A1, A2, A3, A5, A6, A7, A9, A10, A11, A12, A13, A14, A15, A16, A17, A18, A19, A20, A21, A22, and A23, or wherein said APM1-related biallelic marker is selected from the group consisting of A4, A8, A24, A25 and A26; optionally, wherein said APM1-related biallelic marker is selected from the group consisting of A1, A2, and A7 or the group consisting of A4 and A8.

The primers and probes can be prepared by any suitable method, including, for example, cloning and restriction of appropriate sequences and direct chemical synthesis by a method such as the phosphodiester method of Narang et al.(1979), the phosphodiester method of Brown et al.(1979), the diethylphosphoramidite method of Beaucage et al.(1981) and the solid support method described in EP 0 707 592. The disclosures of all these documents are incorporated herein by reference.

Detection probes are generally nucleic acid sequences or uncharged nucleic acid analogs such as, for example peptide nucleic acids which are disclosed in International Patent Application WO 92/20702, and morpholino analogs which are described in U.S. Pat. Nos. 5,185,444, 5,034,506 and 5,142,047. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group can be cleaved, replaced or modified. U.S. patent application Ser. No. 07/049,061, filed Apr. 19, 1993, describes modifications, which can be used to render a probe non-extendable.

Any of the polynucleotides of the present invention can be labeled, if desired, by incorporating a label detectable by spectroscopic, photochemical, biochemical, immunochemical, or chemical means. For example, useful labels include radioactive substances ($^{32}$p, $^{35}$S, $^{3}$H, $^{125}$I), fluorescent dyes (5-bromodesoxyuridin, fluorescein, acetylaminofluorene, digoxigenin) and biotin. Preferably, polynucleotides are labeled at their 3 ' and/or 5' ends. Examples of non-radioactive labeling of nucleic acid fragments are described in French patent No. FR-7810975 or by Urdea et al (1988) or Sanchez-Pescador et al (1988). In addition, the probes according to the present invention may have structural characteristics such that they allow the signal amplification, such structural characteristics being, for example, branched DNA probes as those described by Urdea et al. in 1991 or in European patent No. EP 0 225 807 (Chiron).

A label can also be used to capture the primer, so as to facilitate the immobilization of either the primer or a primer extension product, such as amplified DNA, on a solid support. A capture label is attached to the primers or probes and can be a specific binding member which forms a binding pair with the solid phase reagent's specific binding member (e.g. biotin and streptavidin). Therefore, depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the APM1 gene or mRNA using other techniques well-known in the art.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the solid support that one or more polynucleotides of the invention are attached to.

Consequently, the invention also deals with a method for detecting the presence of a nucleic acid comprising a nucleotide sequence selected from a group consisting of SEQ ID Nos 1–5, a fragment or a variant thereof or a complementary sequence thereto in a sample, said method comprising the following steps of:

a) bringing into contact a nucleic acid probe or a plurality of nucleic acid probes that can hybridize with a nucleotide sequence included in a nucleic acid selected from the group consisting of the nucleotide sequences of SEQ ID Nos 1–5, a fragment or a variant thereof or a complementary sequence thereto and the sample to be assayed.

b) detecting the hybrid complex formed between the probe and a nucleic acid in the sample.

In a first preferred embodiment of this detection method, said nucleic acid probe or the plurality of nucleic acid probes are labeled with a detectable molecule. In a second preferred embodiment of said method, said nucleic acid probe or the plurality of nucleic acid probes has been immobilized on a substrate. In a third preferred embodiment, the nucleic acid probe or the plurality of nucleic acid probes comprise either a sequence which is selected from the group consisting of the nucleotide sequences of SEQ ID Nos B1 to B23, C1 to C24, D1 to 26 and E1 to E26 or a biallelic marker selected from the group consisting of A1 to A26 or the complements thereto.

The invention further concerns a kit for detecting the presence of a nucleic acid comprising a nucleotide sequence selected from a group consisting of SEQ ID Nos 1–5, a fragment or a variant thereof or a complementary sequence thereto in a sample, said kit comprising:

a) a nucleic acid probe or a plurality of nucleic acid probes that can hybridize with a nucleotide sequence included in a nucleic acid selected form the group consisting of the nucleotide sequences of SEQ ID Nos 1–5, a fragment or a variant thereof or a complementary sequence thereto;

b) optionally, the reagents necessary for performing the hybridization reaction.

In a first preferred embodiment of the detection kit, the nucleic acid probe or the plurality of nucleic acid probes are labeled with a detectable molecule. In a second preferred embodiment of the detection kit, the nucleic acid probe or the plurality of nucleic acid probes has been immobilized on a substrate. In a third preferred embodiment of the detection kit, the nucleic acid probe or the plurality of nucleic acid probes comprise either a sequence which is selected from the group consisting of the nucleotide sequences of SEQ ID Nos B1 to B23, C1 to C24, D1 to D26 and E1 to E26 or a biallelic marker selected from the group consisting of A1 to A26 or the complements thereto.

Oligonucleotide Arrays

A substrate comprising a plurality of oligonucleotide primers or probes of the invention may be used either for detecting or amplifying targeted sequences in the APM1 gene and may also be used for detecting mutations in the coding or in the non-coding sequences of the APM1 gene.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotide makes these "addressable" arrays particularly useful in hybridization assays. Any addressable array technology known in the art can be employed with the polynucleotides of the invention. One particular embodiment of these polynucleotide arrays, known as Genechips™, has been generally described in U.S. Pat. No. 5,143,854 and PCT publications WO 90/15070 and 92/10092. These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854 and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256.

In another embodiment of the oligonucleotide arrays of the invention, an oligonucleotide probe matrix may advantageously be used to detect mutations occurring in the APM1 gene and preferably in its regulatory region. For this particular purpose, probes are specifically designed to have a nucleotide sequence allowing their hybridization to the genes that carry known mutations (either by deletion, insertion or substitution of one or several nucleotides). By known mutations is meant mutations on the APM1 gene that have been identified according, for example, to the technique used by Huang et al.(1996) or Samson et al.(1996).

Another technique that is used to detect mutations in the APM1 gene is a high-density DNA array. Each oligonucleotide probe constituting a unit element of the high density DNA array is designed to match a specific subsequence of the APM1 genomic DNA or cDNA. Thus, an array of wild-type Apm1 oligonucleotides complementary to subsequences of the target gene sequence is used to determine the identity of the target sequence, measure its amount, and detect differences between the target sequence and the reference sequence. In one such design (4L tiled array) uses a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild-type reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. in 1996, which is herein incorporated by reference.

Consequently, the invention concerns an array of nucleic acid molecules comprising at least one polynucleotide described above as probes and primers. Preferably, the invention concerns an array of nucleic acid sequences comprising at least two polynucleotides described above as probes and primers.

A further object of the invention consists of an array of nucleic acid sequences comprising either at least one of the sequences selected from the group consisting of SEQ ID Nos B1 to B23, C1 to C24, D1 to D26 and E1 to E26 or the sequences complementary thereto or a fragment thereof of, or at least 8, 10, 12, 15, 18, 20, 25, 30, or 40 consecutive nucleotides thereof, or at least one sequence comprising a biallelic marker selected from the group consisting of A1 to A26 or the complements thereto.

The invention also pertains to an array of nucleic acid sequences comprising either at least two of the sequences selected from the group consisting of SEQ ID Nos B1 to B23, C1 to C24, D1 to D26 and E1 to E26 or the sequences complementary thereto or a fragment thereof, or at least 8 consecutive nucleotides thereof, or at least two sequences comprising a biallelic marker selected from the group consisting of A1 to A26 or the complements thereto.

APM1 Proteins and Polypeptide Fragments

The term "APM1 polypeptides" is used herein to embrace all of the proteins and polypeptides of the present invention. Also forming part of the invention are polypeptides encoded by the polynucleotides of the invention, as well as fusion polypeptides comprising such polypeptides. The invention embodies APM1 proteins from humans, including isolated or purified APM1 proteins consisting of, consisting essentially of, or comprising the sequence of SEQ ID NO: 6. It should be noted the APM1 proteins of the invention are based on the naturally-occurring variant of the amino acid sequence of human APM1, wherein the aspartic acid residue of amino acid position 56 has been replaced with a glutamic acid residue. This variant protein and the fragments thereof which contain amino acid position 56 of SEQ ID NO: 6 are collectively referred to herein as "56-Glu variants."

The present invention embodies isolated, purified, and recombinant polypeptides comprising a contiguous span of at least 6 amino acids, preferably at least 8 to 10 amino acids, more preferably at least 12, 15, 20, 25, 30, 40, 50, or 100 amino acids of SEQ ID NO: 6, wherein said contiguous span includes a glutamic acid residue at amino acid position 56 in SEQ ID NO: 6. In other preferred embodiments the contiguous stretch of amino acids comprises the site of a mutation or functional mutation, including a deletion, addition, swap or truncation of the amino acids in the APM1 protein sequence.

APM1 proteins are preferably isolated from human or mammalian tissue samples or expressed from human or mammalian genes. The APM1 polypeptides of the invention can be made using routine expression methods known in the art. The polynucleotide encoding the desired polypeptide, is ligated into an expression vector suitable for any convenient host. Both eukaryotic and prokaryotic host systems are used in forming recombinant polypeptides, and a summary of some of the more common systems is provided herein. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In addition, shorter protein fragments can be produced by chemical synthesis. Alternatively the proteins of the invention are extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis, for example.

Any APM1 cDNA, including SEQ ID NO: 5, can be used to express APM1 proteins and polypeptides. The nucleic acid encoding the APM1 protein or polypeptide to be expressed is operably linked to a promoter in an expression vector using conventional cloning technology. The APM1 insert in the expression vector may comprise the full coding sequence for the APM1 protein or a portion thereof. For example, the APM1 derived insert may encode a polypeptide comprising at least 10 consecutive amino acids of the APM1 protein of SEQ ID NO: 6, where in said consecutive amino acids comprise a glutamic acid residue in amino acid position 56.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for expression in the organism in which the expression vector is introduced, as explained by Hatfield, et al., U.S. Pat. No. 5,082,767.

In one embodiment, the entire coding sequence of the APM1 cDNA through the poly A signal of the cDNA are operably linked to a promoter in the expression vector. Alternatively, if the nucleic acid encoding a portion of the APM1 protein lacks a methionine to serve as the initiation site, an initiating methionine can be introduced next to the first codon of the nucleic acid using conventional techniques. Similarly, if the insert from the APM1 cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The nucleic acid encoding the APM1 protein or a portion thereof is obtained by PCR from a bacterial vector containing the APM1 cDNA of SEQ ID NO: 5. The oligonucleotide primers used are complementary to the APM1 cDNA, or a portion thereof, and contain restriction endonuclease sequences for Pst I incorporated into the 5' primer and BglII at the 5' end of the corresponding cDNA 3' primer, taking care to ensure that the sequence encoding the APM1 protein, or portion thereof, is positioned properly with respect to the poly A signal. The purified fragment obtained from the resulting PCR reaction is digested with PstI, blunt ended with an exonuclease, digested with BglII, purified, and ligated to pXT1.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 µg/mL G418 (Sigma, St. Louis, Mo.).

Alternatively, the nucleic acids encoding the APM1 protein or a portion thereof are cloned into pED6dpc2 (Genetics Institute, Cambridge, Mass.). The resulting pED6dpc2 constructs is\\are transfected into a suitable host cell, such as COS 1 cells. Methotrexate resistant cells are selected and expanded.

The above procedures may also be used to express a mutant APM1 protein responsible for a detectable phenotype or a portion thereof.

The expressed proteins are purified using conventional purification techniques such as ammonium sulfate precipitation or chromatographic separation based on size or charge. The protein encoded by the nucleic acid insert may also be purified using standard immunochromatography techniques. In such procedures, a solution containing the expressed APM1 protein or portion thereof, such as a cell extract, is applied to a column having antibodies against the APM1 protein or portion thereof attached to the chromatography matrix. The expressed protein is allowed to bind to the immunochromatography column. Thereafter, the column is washed to remove non-specifically bound proteins. The specifically bound expressed protein is then released from the column and recovered using standard techniques.

To confirm expression of the APM1 protein or a portion thereof, the proteins expressed in host cells containing an expression vector containing an insert encoding the APM1 protein or a portion thereof can be compared to the proteins expressed in host cells containing the expression vector without an insert. The presence of a band in samples from cells containing the expression vector with an insert which is absent in samples from cells containing the expression vector without an insert indicates that the APM1 protein or a portion thereof is being expressed. Generally, the band will have the mobility expected for the APM1 protein or portion thereof. However, the band may have a mobility different than that expected as a result of modifications such as glycosylation, ubiquitination, or enzymatic cleavage.

Antibodies capable of specifically recognizing the expressed APM1 protein or a portion thereof are described below.

If antibody production is not possible, the nucleic acids encoding the APM1 protein or a portion thereof can be incorporated into expression vectors designed for use in purification schemes employing chimeric polypeptides. In such strategies, the nucleic acid encoding the APM1 protein or a portion thereof is inserted in frame with a gene encoding the other half of the chimera. The other half of the chimera can be β-globin or a nickel binding polypeptide encoding sequence, for example. A chromatography matrix having antibody to β-globin or nickel attached thereto can then be used to purify the chimeric protein. Protease cleavage sites are engineered between the β-globin gene or the nickel binding polypeptide and the APM1 protein or portion thereof. Thus, the two polypeptides of the chimera are separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques are well known to those skilled in the art of molecular biology. Standard methods are published in methods texts such as Davis et al., (Basic Methods in Molecular Biology, L. G. Davis, M. D. Dibner, and J. F. Battey, ed., Elsevier Press, NY, 1986) and many of the methods are available from Stratagene, Life Technologies, Inc., or Promega. Polypeptides may additionally be produced from the construct using in vitro translation systems such as the In vitro Express™ Translation Kit (Stratagene).

Antibodies that Bind APM1 Polypeptides of the Invention

Any APM1 polypeptide or whole protein may be used to generate antibodies capable of specifically binding to expressed APM1 protein or fragments thereof as described. The antibody compositions of the invention are capable of specifically binding or specifically bind to the 56-Glu variant of the APM1 protein. For an antibody composition to specifically bind to the 56-Glu variant of APM1 it must demonstrate at least a 5%, 10%, 15%, 20%, 25%, 50%, or 100% greater binding affinity for the 56-Glu variant of APM1 than for the 56-Asp variant of APM1 in an ELISA, RIA, or other antibody-based binding assay.

In a preferred embodiment of the invention antibody compositions are capable of selectively binding, or selectively bind to an epitope-containing fragment of a polypeptide comprising a contiguous span of at least 6 amino acids, preferably at least 8 to 10 amino acids, more preferably at least 12, 15, 20, 25, 30, 40, 50, or 100 amino acids of SEQ ID NO: 6, wherein said epitope comprises a glutamic acid residue at amino acid position 56 in SEQ ID NO: 6, wherein said antibody composition is optionally either polyclonal or monoclonal.

The present invention also contemplates the use of polypeptides comprising a contiguous span of at least 6 amino acids, preferably at least 8 to 10 amino acids, more preferably at least 12, 15, 20, 25, 50, or 100 amino acids of a APM1 polypeptide in the manufacture of antibodies, wherein said contiguous span comprises a glutamic acid residue at amino acid position 56 of SEQ ID NO:6. In a preferred embodiment such polypeptides are useful in the manufacture of antibodies to detect the presence and absence of the 56-Glu variant.

Non-human animals or mammals, whether wild-type or transgenic, which express a different species of APM1 than the one to which antibody binding is desired, and animals which do not express APM1 (i.e. an APM1 knock out animal as described in herein) are particularly useful for preparing antibodies. APM1 knock out animals will recognize all or most of the exposed regions of APM1 as foreign antigens, and therefore produce antibodies with a wider array of APM1 epitopes. Moreover, smaller polypeptides with only 10 to 30 amino acids may be useful in obtaining specific binding to the 56-Glu variant. In addition, the humoral immune system of animals which produce a species of APM1 that resembles the antigenic sequence will preferentially recognize the differences between the animal's native APM1 species and the antigen sequence, and produce antibodies to these unique sites in the antigen sequence. Such a technique will be particularly useful in obtaining antibodies that specifically bind to the 56-Glu variant.

Amplification of the APM1 Gene

1. DNA Extraction

As for the source of the genomic DNA to be subjected to analysis, almost any test sample can be used without any particular limitation. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the context of the present invention is from peripheral venous blood of each donor.

The techniques of DNA extraction are well-known to the technician of ordinary skill in the art. Such techniques are described notably by Lin et al.(1998) and by Mackey et al.(1998).

2. DNA Amplification

DNA amplification techniques are well-known to those skilled in the art. Amplification techniques that can be used in the context of the present invention include, but are not limited to, the ligase chain reaction (LCR) described in EP-A-320 308, WO 9320227 and EP-A-439 182, the disclosures of which are incorporated herein by reference, the polymerase chain reaction (PCR, RT-PCR) and techniques such as the nucleic acid sequence based amplification (NASBA) described in Guatelli J. C., et al.(1990) and in Compton J.(1991), Q-beta amplification as described in European Patent Application No 4544610, strand displacement amplification as described in Walker et al.(1996) and EP A 684 315 and, target mediated amplification as described in PCT Publication WO 9322461, the disclosures of which are incorporated herein by reference. For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770 or, to use Asymmetric Gap LCR (RT-AGLCR) as described by Marshall et al.(1994). AGLCR is a modification of GLCR that allows the amplification of RNA.

The PCR technology is the preferred amplification technique used in the present invention. A variety of PCR techniques are familiar to those skilled in the art. For a review of PCR technology, see White (1997) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188. Each of these publications is incorporated herein by reference.

One of the aspects of the present invention is a method for the amplification of the human APM1 gene, particularly of the genomic sequence of SEQ ID No 1 or of the cDNA sequence of SEQ ID No 5, or a fragment or a variant thereof in a test sample, preferably using the PCR technology. This method comprises the steps of contacting a test sample suspected of containing the target APM1 encoding sequence or portion thereof with amplification reaction reagents comprising a pair of amplification primers, and eventually in some instances a detection probe that can hybridize with an internal region of amplicon sequences to confirm that the desired amplification reaction has taken place.

Thus, the present invention also relates to a method for the amplification of a human APM1 gene sequence, particularly of a portion of the genomic sequences of SEQ ID No 1 or of the cDNA sequence of SEQ ID No 5, or a variant thereof in a test sample, said method comprising the steps of:

a) contacting a test sample suspected of containing the targeted APM1 gene sequence comprised in a nucleotide sequence selected from a group consisting of SEQ ID Nos 1 and 5, or fragments or variants thereof with amplification reaction reagents comprising a pair of amplification primers as described above and located on either side of the polynucleotide region to be amplified, and b) optionally, detecting the amplification products.

In a first preferred embodiment of the above amplification method, the amplification product is detected by hybridization with a labeled probe having a sequence which is complementary to the amplified region. In a second preferred embodiment, the nucleic acid primers comprise a sequence which is selected from the group consisting of B1 to B23, C1 to C24, D1 to D26 and E1 to E26. The primers are more particularly characterized in that they have sufficient complementarity with any sequence of a strand of the genomic sequence close to the region to be amplified, for example with a non-coding sequence adjacent to the exons to be amplified.

The invention also concerns a kit for the amplification of a human APM1 gene sequence, particularly of a portion of the genomic sequence of SEQ ID No 1 or of the cDNA sequence of SEQ ID No 5, or a variant thereof in a test sample, wherein said kit comprises:

a) a pair of oligonucleotide primers located on either side of the APM1 region to be amplified;

b) optionally, the reagents necessary for performing the amplification reaction.

In one embodiment of the above amplification kit, the amplification product is detected by hybridization with a labeled probe having a sequence which is complementary to the amplified region.

In another embodiment of the above amplification kit, primers comprise a sequence which is selected from the group consisting of B1 to B23, C1 to C24, D1 to D26 and E1 to E26.

APM1-related Biallelic Markers

Biallelic markers generally consist of a polymorphism at one single base position. Each biallelic marker therefore corresponds to two forms of a polynucleotide sequence which, when compared with one another, present a nucleotide modification at one position. Usually, the nucleotide modification involves the substitution of one nucleotide for another (for example C instead of T).

Advantages of the Biallelic Markers of the Present Invention

The APM1-related biallelic markers of the present invention offer a number of important advantages over other genetic markers such as RFLP (Restriction fragment length polymorphism) and VNTR (Variable Number of Tandem Repeats) markers.

The first generation of markers, were RFLPs, which are variations that modify the length of a restriction fragment. But methods used to identify and to type RFLPs are relatively wasteful of materials, effort, and time. The second generation of genetic markers were VNTRs, which can be categorized as either minisatellites or microsatellites. Minisatellites are tandemly repeated DNA sequences present in units of 5–50 repeats which are distributed along regions of the human chromosomes ranging from 0.1 to 20 kilobases in length. Since they present many possible alleles, their informative content is very high. Minisatellites are scored by performing Southern blots to identify the number of tandem repeats present in a nucleic acid sample from the individual being tested. However, there are only $10^4$ potential VNTRs that can be typed by Southern blotting. Moreover, both RFLP and VNTR markers are costly and time-consuming to develop and assay in large numbers.

Single nucleotide polymorphism or biallelic markers can be used in the same manner as RFLPs and VNTRs but offer several advantages. SNP are densely spaced in the human genome and represent the most frequent type of variation.

An estimated number of more than 10⁷ sites are scattered along the 3×10⁹ base pairs of the human genome. Therefore, SNP occur at a greater frequency and with greater uniformity than RFLP or VNTR markers which means that there is a greater probability that such a marker will be found in close proximity to a genetic locus of interest. SNP are less variable than VNTR markers but are mutationally more stable.

Also, the different forms of a characterized single nucleotide polymorphism, such as the biallelic markers of the present invention, are often easier to distinguish and can therefore be typed easily on a routine basis. Biallelic markers have single nucleotide based alleles and they have only two common alleles, which allows highly parallel detection and automated scoring. The biallelic markers of the present invention offer the possibility of rapid, high throughput genotyping of a large number of individuals.

Biallelic markers are densely spaced in the genome, sufficiently informative and can be assayed in large numbers. The combined effects of these advantages make biallelic markers extremely valuable in genetic studies. Biallelic markers can be used in linkage studies in families, in allele sharing methods, in linkage disequilibrium studies in populations, in association studies of case-control populations or of trait positive and trait negative populations. An important aspect of the present invention is that biallelic markers allow association studies to be performed to identify genes involved in complex traits. Association studies examine the frequency of marker alleles in unrelated case- and control-populations and are generally employed in the detection of polygenic or sporadic traits. Association studies may be conducted within the general population and are not limited to studies performed on related individuals in affected families (linkage studies). Biallelic markers in different genes can be screened in parallel for direct association with disease or response to a treatment. This multiple gene approach is a powerful tool for a variety of human genetic studies as it provides the necessary statistical power to examine the synergistic effect of multiple genetic factors on a particular phenotype, drug response, sporadic trait, or disease state with a complex genetic etiology.

Candidate Gene of the Present Invention

Different approaches can be employed to perform association studies: genome-wide association studies, candidate region association studies and candidate gene association studies. Genome-wide association studies rely on the screening of genetic markers evenly spaced and covering the entire genome. The candidate gene approach is based on the study of genetic markers specifically located in genes potentially involved in a biological pathway related to the trait of interest. In the present invention, APM1 is the candidate gene. Indeed, the APM1 gene seems to be involved in obesity and in others disorders linked to obesity. The candidate gene analysis clearly provides a short-cut approach to the identification of genes and gene polymorphisms related to a particular trait when some information concerning the biology of the trait is available. However, it should be noted that all of the biallelic markers disclosed in the instant application can be employed as part of genome-wide association studies or as part of candidate region association studies and such uses are specifically contemplated in the present invention and claims.

APM1-Related Biallelic Markers and Polynucleotides Related Thereto

The invention also concerns APM1-related biallelic markers. As used herein the term "APM1-related biallelic marker" relates to a set of biallelic markers in linkage disequilibrium with the APM1 gene. The term APM1-related biallelic marker includes the biallelic markers designated A1 to A26.

A portion of the biallelic markers of the present invention are disclosed in Tables A and B. Their location on the APM1 gene is indicated in Tables A and B and also as a single base polymorphism in the features of SEQ ID No 1. The pairs of primers allowing the amplification of a nucleic acid containing the polymorphic base of one APM1 biallelic marker are listed in Table 1 of Example 2.

TABLE A

List of biallelic markers surrounded by sequence that has never been previously suggested in the art.

| Biallelic marker | Marker Name | Localization in APM1 gene | Polymorphism | Frequency Of Allele 2 | Marker position in SEQ ID No 1 |
|---|---|---|---|---|---|
| A1 | 9-27/261 | 5' regulatory region | Allele 1: G Allele 2: C | | 3787 |
| A2 | 99-14387/129 | Intron 1 | Allele 1: A Allele 2: C | | 11118 |
| A3 | 9-12/48 | Intron 1 | Allele 1: T Allele 2: C | 1.5% | 15120 |
| A5 | 9-12/355 or 9-13/297 | Intron 2 | Allele 1: G Allele 2: T | 26% | 15427 |
| A6 | 9-12/428 or 9-13/370 | Intron 2 | Allele 1: A Allele 2: G | 11% | 15500 |
| A7 | 99-14405/105 | Intron 2 | Allele 1: G Allele 2: A | 37% | 15863 |
| A9 | 17-30-216 | 5' regulatory region | Allele 1: G Allele 2: A | | 945 |
| A10 | 9-27-211 | 5' regulatory region | Allele 1: A Allele 2: G | | 3738 |
| A11 | 9-27-246 | 5' regulatory region | Allele 1: G Allele 2: A | | 3773 |
| A12 | 17-31-298 | Intron 1 | Allele 1: A Allele 2: G | | 5095 |
| A13 | 17-31-413 | Intron 1 | Allele 1: T Allele 2: C | | 5210 |

TABLE A-continued

List of biallelic markers surrounded by
sequence that has never been previously suggested in the art.

| Biallelic marker | Marker Name | Localization in APM1 gene | Polymorphism | Frequency Of Allele 2 | Marker position in SEQ ID No 1 |
|---|---|---|---|---|---|
| A14 | 17-32-24 | Intron 1 | Allele 1: T<br>Allele 2: C | | 10637 |
| A15 | 99-14387-50 | Intron 1 | Allele 1: C<br>Allele 2: A | | 11039 |
| A16 | 99-14387-199 | Intron 1 | Allele 1: A<br>Allele 2: G | | 11188 |
| A17 | 17-33-TGAGACT | Intron 1 | Allele 1: no insert<br>Allele 2: TGAGACT insert | | 13973 |
| A18 | 17-34-860 | Intron 1 | Allele 1: G<br>Allele 2: A | | 14702 |
| A19 | 17-34-915 | Intron 1 | Allele 1: G<br>Allele 2: A | | 14757 |
| A20 | 17-35-71 | Intron 1 | Allele 1: C<br>Allele 2: T | | 14815 |
| A21 | 17-35-306 | Intron 1 | Allele 1: G<br>Allele 2: T | | 15050 |
| A22 | 17-36-47 | Intron 2 | Allele 1: G<br>Allele 2: C | | 15680 |
| A23 | 17-36-120 | Intron 2 | Allele 1: C<br>Allele 2: T | | 15790 |

TABLE B

List of biallelic markers surrounded by previously suggested sequence,
where one allele, allele 2, has never been previously suggested in the art.
The identity of the nucleotide of the original allele has been previously suggested in art.

| Biallelic marker | Marker Name | Localization in APM1 gene | Polymorphism | Frequency Of Allele 2 | Marker position in SEQ ID No 1 |
|---|---|---|---|---|---|
| A4 | 9-12/124 or 9-13/66 | Exon 2 | Allele 1: T<br>Allele 2: G | 11.5% | 15196 |
| A8 | 9-16/189 | Exon 3 | Allele 1: A<br>Allele 2: Del | 40% | 17170 |
| A24 | 17-37-629 | Exon 3 | Allele 1: A<br>Allele 2: G | | 17829 |
| A25 | 17-37-811 | Exon 3 | Allele 1: G<br>Allele 2: A | | 18011 |
| A26 | 17-38-349 | Exon 3 | Allele 1: C<br>Allele 2: T | | 18489 |

The invention also relates to a purified and/or isolated nucleotide sequence comprising a polymorphic base of a biallelic marker located in the sequence of the APM1 gene, preferably of a biallelic marker selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof; optionally, wherein said APM1-related biallelic marker is selected from the group consisting of A1, A2, and A7 or the group consisting of A4 and A8. The sequence has between 8 and 1000 nucleotides in length, and preferably comprises at least 8, 10, 12, 15, 18, 20, 25, 35, 40, 50, 60, 70, 80, 100, 250, 500 or 1000 contiguous nucleotides of a nucleotide sequence selected from the group consisting of SEQ ID Nos 1 and 5 or a variant thereof or a complementary sequence thereto. These nucleotide sequences comprise the polymorphic base of either allele 1 or allele 2 of the considered biallelic marker. Optionally, said biallelic marker may be within 6, 5, 4, 3, 2, or 1 nucleotides of the center of said polynucleotide or at the center of said polynucleotide. Optionally, the 3' end of said contiguous span may be present at the 3' end of said polynucleotide. Optionally, biallelic marker may be present at the 3' end of said polynucleotide. Optionally, the 3' end of said polynucleotide may be located within or at least 2, 4, 6, 8, 10, 12, 15, 18, 20, 25, 50, 100, 250, 500, or 1000 nucleotides upstream of a biallelic marker of the APM1 gene in said sequence. Optionally, the 3' end of said polynucleotide may be located 1 nucleotide upstream of a biallelic marker of the APM1 gene in said sequence. Optionally, said polynucleotide may further comprise a label. Optionally, said polynucleotide can be attached to solid support. In a further embodiment, the polynucleotides defined above can be used alone or in any combination.

In a preferred embodiment, the sequences comprising a polymorphic base of one of the biallelic markers listed in Tables A and B are selected from the group consisting of the nucleotide sequences that have a contiguous span of, that consist of, that are comprised in, or that comprise a polynucleotide selected from the group consisting of the nucleic acid sequences set forth as Nos 9-27, 99-14387, 9-12, 9-13, 99-14405, and 9-16 (listed in Table 1) or a variant thereof or a complementary sequence thereto.

The invention further concerns a nucleic acid encoding the APM1 protein, wherein said nucleic acid comprises a polymorphic base of a biallelic marker selected from the group consisting of A1, A2, A3, A4, A5, A6, A7, A8, A9, A10, A11, A12, A13, A14, A15, A16, A17, A18, A19, A20, A21, A22, A23, A24, A25 and A26 and the complements thereof; optionally, wherein said APM1-related biallelic marker is selected from the group consisting of A1, A2, and A7 or the group consisting of A4 and A8.

The invention also encompasses the use of any polynucleotide for, or any polynucleotide for use in, determining the identity of one or more nucleotides at a APM1-related biallelic marker. In addition, the polynucleotides of the invention for use in determining the identity of one or more nucleotides at a APM1-related biallelic marker encompass polynucleotides with any further limitation described in this disclosure, or those following, specified alone or in any combination. Optionally, said APM1-related biallelic marker may be selected from the group consisting of A1, A2, A3, A4, A5, A6, A7, A8, A9, A10, A11, A12, A13, A14, A15, A16, A17, A18, A19, A20 , A21, A22, A23, A24, A25 and A26, and the complements thereof; optionally, wherein said APM1-related biallelic marker is selected from the group consisting of A1, A2, and A7 or the group consisting of A4 and A8. Optionally, said polynucleotide may comprise a sequence disclosed in the present specification. Optionally, said polynucleotide may consist of, or consist essentially of any polynucleotide described in the present specification. Optionally, said determining may be performed in a hybridization assay, sequencing assay, microsequencing assay, or allele-specific amplification assay. Optionally, said polynucleotide may be attached to a solid support, array, or addressable array. Optionally, said polynucleotide may be labeled. A preferred polynucleotide may be used in a hybridization assay for determining the identity of the nucleotide at a biallelic marker of the APM1 gene. Another preferred polynucleotide may be used in a sequencing or microsequencing assay for determining the identity of the nucleotide at a biallelic marker of the APM1 gene. A third preferred polynucleotide may be used in an allele-specific amplification assay for determining the identity of the nucleotide at a biallelic marker of the APM1 gene. A fourth preferred polynucleotide may be used in amplifying a segment of polynucleotides comprising a biallelic marker of the APM1 gene. Optionally, any of the polynucleotides described above may be attached to a solid support, array, or addressable array. Optionally, said polynucleotide may be labeled.

Additionally, the invention encompasses the use of any polynucleotide for, or any polynucleotide for use in, amplifying a segment of nucleotides comprising a APM1-related biallelic marker. In addition, the polynucleotides of the invention for use in amplifying a segment of nucleotides comprising a APM1-related biallelic marker encompass polynucleotides with any further limitation described in this disclosure, or those following, specified alone or in any combination. Optionally, said APM1-related biallelic marker may be selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof; optionally, wherein said APM1-related biallelic marker is selected from the group consisting of A1, A2, and A7 or the group consisting of A4 and A8. Optionally, said polynucleotide may comprise a sequence disclosed in the present specification. Optionally, said polynucleotide may consist of, or consist essentially of any polynucleotide described in the present specification. Optionally, said amplifying may be performed by a PCR or LCR. Optionally, said polynucleotide may be attached to a solid support, array, or addressable array. Optionally, said polynucleotide may be labeled.

The primers for amplification or sequencing reaction of a polynucleotide comprising a biallelic marker of the invention may be designed from the disclosed sequences for any method known in the art. A preferred set of primers are fashioned such that the 3' end of the contiguous span of identity with a sequence selected from the group consisting of SEQ ID Nos 1 or 5 or a sequence complementary thereto or a variant thereof is present at the 3' end of the primer. Such a configuration allows the 3' end of the primer to hybridize to a selected nucleic acid sequence and dramatically increases the efficiency of the primer for amplification or sequencing reactions. Allele specific primers may be designed such that a polymorphic base of a biallelic marker is at the 3' end of the contiguous span and the contiguous span is present at the 3' end of the primer. Such allele specific primers tend to selectively prime an amplification or sequencing reaction so long as they are used with a nucleic acid sample that contains one of the two alleles present at a biallelic marker. The 3' end of the primer of the invention may be located within or at least 2, 4, 6, 8, 10, 12, 15, 18, 20, 25, 50, 100, 250, 500, or 1000 nucleotides upstream of a biallelic marker of APM1 in said sequence or at any other location which is appropriate for their intended use in sequencing, amplification or the location of novel sequences or markers. Thus, another set of preferred amplification primers comprise an isolated polynucleotide consisting essentially of a contiguous span of 8 to 50 nucleotides in a sequence selected from the group consisting of SEQ ID Nos 1 and 5 or a sequence complementary thereto or a variant thereof, wherein the 3' end of said contiguous span is located at the 3' end of said polynucleotide, and wherein the 3' end of said polynucleotide is located upstream of a biallelic marker of the APM1 gene in said sequence. Preferably, those amplification primers comprise a sequence selected from the group consisting of the sequences B1 to B23 and C1 to C24. Primers with their 3' ends located 1 nucleotide upstream of a biallelic marker of APM1 have a special utility as microsequencing assays. Preferred microsequencing primers are described in Table 3. Optionally, the biallelic marker of the APM1 gene is selected from the group consisting of A1, A2, A3, A5, A6, A7, A9, A10, A11, A12, A13, A14, A15, A16, A17, A18, A19, A20, A21, A22, and A23 and the complements thereof. Optionally, the biallelic marker of the APM1 gene is selected from the group consisting of A4, A8, A24, A25 and A26 and the complements thereof; optionally, wherein said APM1-related biallelic marker is selected from the group consisting of A1, A2, and A7 or the group consisting of A4 and A8. Optionally, microsequencing primers are selected from the group consisting of the nucleotide sequences D1 to D26 and E1 to E26. Alternatively preferred microsequencing primers are selected from the group consisting of the nucleotide sequences D3, E4, E5, E6, D7 and D8.

The probes of the present invention may be designed from the disclosed sequences for any method known in the art, particularly methods which allow for testing if a marker disclosed herein is present. A preferred set of probes may be designed for use in the hybridization assays of the invention in any manner known in the art such that they selectively bind to one allele of a biallelic marker, but not the other under any particular set of assay conditions. Preferred hybridization probes comprise the polymorphic base of either allele 1 or allele 2 of the considered biallelic marker. Optionally, said biallelic marker may be within 6, 5, 4, 3, 2, or 1 nucleotides of the center of the hybridization probe or at the center of said probe. Exemplary probes are provided in Table 4 in the Examples.

The polynucleotides of the present invention are not limited to having the exact flanking sequences surrounding the polymorphic bases which are enumerated in the Sequence Listing. The flanking sequences surrounding the biallelic markers may be lengthened or shortened to any extent compatible with their intended use and the present invention specifically contemplates such sequences. The flanking regions outside of the contiguous span need not be homologous to native flanking sequences that are known to occur in human subjects. The addition of any nucleotide sequence that is compatible with the nucleotides intended use is specifically contemplated.

Primers and probes may be labeled or immobilized on a solid support as described in" Oligonucleotide probes and primers".

The polynucleotides of the invention which are attached to a solid support encompass polynucleotides with any further limitation described in this disclosure, or those following, specified alone or in any combination. Optionally, said polynucleotides may be specified as attached individually or in groups of at least 2, 5, 8, 10, 12, 15, 20, or 25 distinct polynucleotides of the invention to a single solid support. Optionally, polynucleotides other than those of the invention may attached to the same solid support as polynucleotides of the invention. Optionally, when multiple polynucleotides are attached to a solid support they may be attached at random locations, or in an ordered array. Optionally, said ordered array may be addressable.

The invention also pertains to a method of genotyping comprising determining the identity of a nucleotide at a biallelic marker of the APM1 gene selected from the group consisting of A1, A2, A3, A5, A6, A7, A9, A10, A11, A12, A13, A14, A15, A16, A17, A18, A19, A20, A21, A22, and A23 and the complements thereof in a biological sample; optionally, wherein said APM1-related biallelic marker is selected from the group consisting of A1, A2, and A7 or the group consisting of A4 and A8.

The invention further deals with a method of genotyping comprising determining the identity of a nucleotide at an APM1-related biallelic marker, preferably a biallelic marker of the APM1 gene selected from the group consisting of A4, A8, A24, A25 and A26 and the complements thereof in a biological sample.

Optionally, the biological sample is derived from a single subject. Optionally, the identity of the nucleotides at said biallelic marker is determined for both copies of said biallelic marker present in said individual's genome. Optionally, the biological sample is derived from multiple subjects. Optionally, the method of genotyping described above further comprises amplifying a portion of said sequence comprising the biallelic marker prior to said determining step, for example by a PCR amplification.

The determining step of the above genotyping method may be performed using a hybridization assay, a sequencing assay, an allele-specific amplification assay or a microsequencing assay. Thus, the invention also encompasses methods of genotyping a biological sample comprising determining the identity of a nucleotide at a APM1-related biallelic marker. In addition, the genotyping methods of the invention encompass methods with any further limitation described in this disclosure, or those following, specified alone or in any combination. Optionally, said APM1-related biallelic marker may be selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof; optionally, wherein said APM1-related biallelic marker is selected from the group consisting of A1, A2, and A7 or the group consisting of A4 and A8. Optionally, said biological sample is derived from a single individual or subject. Optionally, said method is performed in vitro. Optionally, said biallelic marker is determined for both copies of said biallelic marker present in said individual's genome. Optionally, said biological sample is derived from multiple subjects or individuals. Optionally, said method further comprises amplifying a portion of said sequence comprising the biallelic marker prior to said determining step. Optionally, wherein said amplifying is performed by PCR, LCR, or replication of a recombinant vector comprising an origin of replication and said portion in a host cell. Optionally, wherein said determining is performed by a hybridization assay, sequencing assay, microsequencing assay, or allele-specific amplification assay.

The present invention also encompasses diagnostic kits comprising one or more polynucleotides of the invention with a portion or all of the necessary reagents and instructions for genotyping a test subject by determining the identity of a nucleotide at a biallelic marker of APM1. The polynucleotides of a kit may optionally be attached to a solid support, or be part of an array or addressable array of polynucleotides. The kit may provide for the determination of the identity of the nucleotide at a marker position by any method known in the art including, but not limited to, a sequencing assay method, a microsequencing assay method, a hybridization assay method, or an allele specific amplification method. Optionally such a kit may include instructions for scoring the results of the determination with respect to the test subjects' risk of suffering of obesity or disorders linked to obesity.

Methods for De Novo Identification of Biallelic Markers

Any of a variety of methods can be used to screen a genomic fragment for single nucleotide polymorphisms such as differential hybridization with oligonucleotide probes, detection of changes in the mobility measured by gel electrophoresis or direct sequencing of the amplified nucleic acid. A preferred method for identifying biallelic markers involves comparative sequencing of genomic DNA fragments from an appropriate number of unrelated individuals.

In a first embodiment, DNA samples from unrelated individuals are pooled together, following which the genomic DNA of interest is amplified and sequenced. The nucleotide sequences thus obtained are then analyzed to identify significant polymorphisms. One of the major advantages of this method resides in the fact that the pooling of the DNA samples substantially reduces the number of DNA amplification reactions and sequencing reactions, which must be carried out. Moreover, this method is sufficiently sensitive so that a biallelic marker obtained thereby usually demonstrates a sufficient frequency of its less common allele to be useful in conducting association studies.

In a second embodiment, the DNA samples are not pooled and are therefore amplified and sequenced individually. This method is usually preferred when biallelic markers need to be identified in order to perform association studies within candidate genes. Preferably, highly relevant gene regions such as promoter regions or exon regions may be screened for biallelic markers. A biallelic marker obtained using this method may show a lower degree of informativeness for conducting association studies, e.g. if the frequency of its less frequent allele may be less than about 10%. Such a biallelic marker will, however, be sufficiently informative to conduct association studies and it will further be appreciated that including less informative biallelic markers in the genetic analysis studies of the present invention, may allow in some cases the direct identification of causal mutations, which may, depending on their penetrance, be rare mutations.

The following is a description of the various parameters of a preferred method used by the inventors for the identification of the biallelic markers of the present invention.

Genomic DNA Samples

The genomic DNA samples from which the biallelic markers of the present invention are generated are preferably obtained from unrelated individuals corresponding to a heterogeneous population of known ethnic background. The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to identify as many markers as possible and to generate statistically significant results.

As for the source of the genomic DNA to be subjected to analysis, any test sample can be foreseen without any particular limitation. These test samples include biological samples, which can be tested by the methods of the present invention described herein, and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the present invention is from peripheral venous blood of each donor. Techniques to prepare genomic DNA from biological samples are well known to the skilled technician. Details of a preferred embodiment are provided in Example 1. The person skilled in the art can choose to amplify pooled or unpooled DNA samples.

DNA Amplification

The identification of biallelic markers in a sample of genomic DNA may be facilitated through the use of DNA amplification methods. DNA samples can be pooled or unpooled for the amplification step. DNA amplification techniques are well known to those skilled in the art. Various methods to amplify DNA fragments carrying biallelic markers are further described hereinbefore in "Amplification of the APM1 gene". The PCR technology is the preferred amplification technique used to identify new biallelic markers. A typical example of a PCR reaction suitable for the purposes of the present invention is provided in Example 2.

In a first embodiment of the present invention, biallelic markers are identified using genomic sequence information generated by the inventors. Sequenced genomic DNA fragments are used to design primers for the amplification of 500 bp fragments. These 500 bp fragments are amplified from genomic DNA and are scanned for biallelic markers. Primers may be designed using the OSP software (Hillier L. and Green P., 1991). All primers may contain, upstream of the specific target bases, a common oligonucleotide tail that serves as a sequencing primer. Those skilled in the art are familiar with primer extensions, which can be used for these purposes.

Preferred primers, useful for the amplification of genomic sequences encoding the candidate genes, focus on promoters, exons and splice sites of the genes. A biallelic marker presents a higher probability to be an eventual causal mutation if it is located in these functional regions of the gene. Preferred amplification primers of the invention include the nucleotide sequences Nos B1 to B23 and the nucleotide sequences Nos C1 to C24 disclosed in Example 2.

Sequencing of Amplified Genomic DNA and Identification of Single Nucleotide Polymorphisms The amplification products generated as described above, are then sequenced using any method known and available to the skilled technician. Methods for sequencing DNA using either the dideoxy-mediated method (Sanger method) or the Maxam-Gilbert method are widely known to those of ordinary skill in the art. Such methods are for example disclosed in Sambrook et al.(1989). Alternative approaches include hybridization to high-density DNA probe arrays as described in Chee et al.(1996).

Preferably, the amplified DNA is subjected to automated dideoxy terminator sequencing reactions using a dye-primer cycle sequencing protocol. The products of the sequencing reactions are run on sequencing gels and the sequences are determined using gel image analysis. The polymorphism search is based on the presence of superimposed peaks in the electrophoresis pattern resulting from different bases occurring at the same position. Because each dideoxy terminator is labeled with a different fluorescent molecule, the two peaks corresponding to a biallelic site present distinct colors corresponding to two different nucleotides at the same position on the sequence. However, the presence of two peaks can be an artifact due to background noise. To exclude such an artifact, the two DNA strands are sequenced and a comparison between the peaks is carried out. In order to be registered as a polymorphic sequence, the polymorphism has to be detected on both strands.

The above procedure permits those amplification products, which contain biallelic markers to be identified. The detection limit for the frequency of biallelic polymorphisms detected by sequencing pools of 100 individuals is approximately 0.1 for the minor allele, as verified by sequencing pools of known allelic frequencies. However, more than 90% of the biallelic polymorphisms detected by the pooling method have a frequency for the minor allele higher than 0.25. Therefore, the biallelic markers selected by this method have a frequency of at least 0.1 for the minor allele and less than 0.9 for the major allele. Preferably at least 0.2 for the minor allele and less than 0.8 for the major allele, more preferably at least 0.3 for the minor allele and less than 0.7 for the major allele, thus a heterozygosity rate higher than 0.18, preferably higher than 0.32, more preferably higher than 0.42.

In another embodiment, biallelic markers are detected by sequencing individual DNA samples, the frequency of the minor allele of such a biallelic marker may be less than 0.1.

Validation of the Biallelic Markers of the Present Invention

The polymorphisms are evaluated for their usefulness as genetic markers by validating that both alleles are present in a population. Validation of the biallelic markers is accomplished by genotyping a group of individuals by a method of the invention and demonstrating that both alleles are present. Microsequencing is a preferred method of genotyping alleles. The validation by genotyping step may be performed on individual samples derived from each individual in the group or by genotyping a pooled sample derived from more than one individual. The group can be as small as one individual if that individual is heterozygous for the allele in question. Preferably the group contains at least three individuals, more preferably the group contains five or six individuals, so that a single validation test will be more likely to result in the validation of more of the biallelic markers that are being tested. It should be noted, however, that when the validation test is performed on a small group it may result in a false negative result if as a result of sampling error none of the individuals tested carries one of the two alleles. Thus, the validation process is less useful in demonstrating that a particular initial result is an artifact, than it is at demonstrating that there is a bona fide biallelic marker at a particular position in a sequence. All of the genotyping, haplotyping, association, and interaction study methods of the invention may optionally be performed solely with validated biallelic markers.

Evaluation of the Frequency of the Biallelic Markers of the Present Invention

The validated biallelic markers are further evaluated for their usefulness as genetic markers by determining the frequency of the least common allele at the biallelic marker site. The higher the frequency of the less common allele the greater the usefulness of the biallelic marker is association and interaction studies. The determination of the least common allele is accomplished by genotyping a group of individuals by a method of the invention and demonstrating that both alleles are present. This determination of frequency by genotyping step may be performed on individual samples derived from each individual in the group or by genotyping a pooled sample derived from more than one individual. The group must be large enough to be representative of the population as a whole. Preferably the group contains at least 20 individuals, more preferably the group contains at least 50 individuals, most preferably the group contains at least 100 individuals. Of course the larger the group the greater the accuracy of the frequency determination because of reduced sampling error. For an indication of the frequency for the less common allele of a particular biallelic marker of the invention see Table A and B. A biallelic marker wherein the frequency of the less common allele is 30% or more is termed a "high quality biallelic marker." All of the genotyping, haplotyping, association, and interaction study methods of the invention may optionally be performed solely with high quality biallelic markers.

The invention also relates to methods of estimating the frequency of an allele in a population comprising determining the proportional representation of a nucleotide at a APM1-related biallelic marker in said population. In addition, the methods of estimating the frequency of an allele in a population of the invention encompass methods with any further limitation described in this disclosure, or those following, specified alone or in any combination. Optionally, said APM1-related biallelic marker may be selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof; optionally, wherein said APM1-related biallelic marker is selected from the group consisting of A1, A2, and A7 or the group consisting of A4 and A8. Optionally, determining the proportional representation of a nucleotide at a APM1-related biallelic marker may be accomplished by determining the identity of the nucleotides for both copies of said biallelic marker present in the genome of each individual in said population and calculating the proportional representation of said nucleotide at said APM1-related biallelic marker for the population. Optionally, determining the proportional representation may be accomplished by performing a genotyping method of the invention on a pooled biological sample derived from a representative number of individuals, or each individual, in said population, and calculating the proportional amount of said nucleotide compared with the total.

Methods for Genotyping an Individual for Biallelic Markers

Methods are provided to genotype a biological sample for one or more biallelic markers of the present invention, all of which may be performed in vitro. Such methods of genotyping comprise determining the identity of a nucleotide at an APM1 biallelic marker site by any method known in the art. These methods find use in genotyping case-control populations in association studies as well as individuals in the context of detection of alleles of biallelic markers which are known to be associated with a given trait, in which case both copies of the biallelic marker present in individual's genome are determined so that an individual may be classified as homozygous or heterozygous for a particular allele.

These genotyping methods can be performed on nucleic acid samples derived from a single individual or pooled DNA samples.

Genotyping can be performed using similar methods as those described above for the identification of the biallelic markers, or using other genotyping methods such as those further described below. In preferred embodiments, the comparison of sequences of amplified genomic fragments from different individuals is used to identify new biallelic markers whereas microsequencing is used for genotyping known biallelic markers in diagnostic and association study applications.

In one embodiment the invention encompasses methods of genotyping comprising determining the identity of a nucleotide at an APM1-related biallelic marker of SEQ ID No: 1 or the complement thereof in a biological sample. Optionally, the biological sample is derived from a single subject. Optionally, the identity of the nucleotides at said biallelic marker is determined for both copies of said biallelic marker present in said individual's genome. Optionally, the biological sample is derived from multiple subjects. Optionally, the method further comprises amplifying a portion of said sequence comprising the biallelic marker prior to said determining step. Optionally, the amplifying step is performed by PCR. Optionally, the determining step is performed by a hybridization assay, a sequencing assay, a microsequencing assay, or an allele-specific amplification assay.

Source of DNA for Genotyping

Any source of nucleic acids, in purified or non-purified form, can be utilized as the starting nucleic acid, provided it contains or is suspected of containing the specific nucleic acid sequence desired. DNA or RNA may be extracted from cells, tissues, body fluids and the like as described above. While nucleic acids for use in the genotyping methods of the invention can be derived from any mammalian source, the test subjects and individuals from which nucleic acid samples are taken are generally understood to be human.

Amplification of DNA Fragments Comprising Biallelic Markers

Methods and polynucleotides are provided to amplify a segment of nucleotides comprising one or more biallelic marker of the present invention. It will be appreciated that amplification of DNA fragments comprising biallelic markers may be used in various methods and for various purposes and is not restricted to genotyping. Nevertheless, many genotyping methods, although not all, require the previous amplification of the DNA region carrying the biallelic marker of interest. Such methods specifically increase the concentration or total number of sequences that span the biallelic marker or include that site and sequences located either distal or proximal to it. Diagnostic assays may also rely on amplification of DNA segments carrying a biallelic marker of the present invention. Amplification of DNA may be achieved by any method known in the art. Amplification techniques are described above in the section entitled, Amplification of the APM1 Gene.

Some of these amplification methods are particularly suited for the detection of single nucleotide polymorphisms and allow the simultaneous amplification of a target sequence and the identification of the polymorphic nucleotide as it is further described below.

The identification of biallelic markers as described above allows the design of appropriate oligonucleotides, which can be used as primers to amplify DNA fragments comprising the biallelic markers of the present invention. Amplification can be performed using the primers initially used to discover new biallelic markers which are described herein or any set of primers allowing the amplification of a DNA fragment comprising a biallelic marker of the present invention.

In some embodiments the present invention provides primers for amplifying a DNA fragment containing one or more biallelic markers of the present invention. Preferred amplification primers are listed in Example 2. It will be appreciated that the primers listed are merely exemplary and that any other set of primers which produce amplification products containing one or more biallelic markers of the present invention.

The spacing of the primers determines the length of the segment to be amplified. In the context of the present invention, amplified segments carrying biallelic markers can range in size from at least about 25 bp to 35 kbp. Amplification fragments from 25–3000 bp are typical, fragments from 50–1000 bp are preferred and fragments from 100–600 bp are highly preferred. It will be appreciated that amplification primers for the biallelic markers may be any sequence which allow the specific amplification of any DNA fragment carrying the markers. Amplification primers may be labeled or immobilized on a solid support as described in "Oligonucleotide probes and primers".

Methods of Genotyping DNA Samples for Biallelic Markers

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as, conventional dot blot analyzes, single strand conformational polymorphism analysis (SSCP) described by Orita et al.(1989), denaturing gradient gel electrophoresis (DGGE), heteroduplex analysis, mismatch cleavage detection, and other conventional techniques as described in Sheffield et al.(1991), White et al.(1992), Grompe et al.(1989 and 1993). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by sequencing assay, allele-specific amplification assay, or hybridization assay. The following is a description of some preferred methods. A highly preferred method is the microsequencing technique. The term "sequencing" is used herein to refer to polymerase extension of duplex primer/template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing as described above. DNA sequencing methods are described in "Sequencing Of Amplified Genomic DNA And Identification Of Single Nucleotide Polymorphisms".

Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, the nucleotide at a polymorphic site in a target DNA is detected by a single nucleotide primer extension reaction. This method involves appropriate microsequencing primers which, hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883. Alternatively capillary electrophoresis can be used in order to process a higher number of assays simultaneously. An example of a typical microsequencing procedure that can be used in the context of the present invention is provided in Example 4.

Different approaches can be used for the labeling and detection of ddNTPs. A homogeneous phase detection method based on fluorescence resonance energy transfer has been described by Chen and Kwok (1997) and Chen et al.(1997). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, 1997).

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner, oligonucleotides or templates may be attached to a solid support in a high-density format. In such solid phase microsequencing reactions, incorporated ddNTPs can be radiolabeled (Syvänen, 1994) or linked to fluorescein (Livak and Hainer, 1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosphatase conjugate (Harju et al., 1993) or biotinylated ddNTP and horseradish peroxidase-conjugated streptavidin with o-phenylenediamineas a substrate (WO 92/15712). As yet another alternative solid-phase microsequencing procedure, Nyren et al.(1993) described a method relying on the detection of DNA polymerase activity by an enzymatic luminometric inorganic pyrophosphate detection assay (ELIDA).

Pastinen et al.(1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferred microsequencing primers include the nucleotide sequences Nos D1 to D26 and E1 to E26. More preferred microsequencing primers are selected from the group consisting of the nucleotide sequences Nos D3, E4, E5, E6, D7, and D8. It will be appreciated that the microsequencing primers listed in Example 4 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in Example 4, or fragments comprising at least 8, 12, 15, 20, 25, 30, 40, or 50 consecutive nucleotides thereof and having a 3' terminus immediately upstream of the corresponding biallelic marker, for determining the identity of a nucleotide at a biallelic marker site.

3) Allele-Specific Amplification Assay Methods

In one aspect the present invention provides polynucleotides and methods to determine the allele of one or more biallelic markers of the present invention in a biological sample, by allele-specific amplification assays. Methods, primers and various parameters to amplify DNA fragments comprising biallelic markers of the present invention are further described above in "Amplification Of DNA Fragments Comprising Biallelic Markers".

Allele Specific Amplification Primers

Discrimination between the two alleles of a biallelic marker can also be achieved by allele specific amplification, a selective strategy, whereby one of the alleles is amplified without amplification of the other allele. This is accomplished by placing the polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well with the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al.(1990). In this method, PCR is used to achieve the exponential amplification of target DNA, which is then detected using OLA.

Other amplification methods which are particularly suited for the detection of single nucleotide polymorphism include LCR (ligase chain reaction), Gap LCR (GLCR) which are described above in "Amplification of the APM1 gene". LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., 1989).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., 1989). Stringent conditions are sequence dependent and will be different in different circumstances. Generally, stringent conditions are selected to be about 5° C. lower than the thermal melting point (Tm) for the specific sequence at a defined ionic strength and pH. Although such hybridizations can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995). In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., 1998).

The polynucleotides provided herein can be used to produce probes which can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Preferably the biallelic marker is within 4 nucleotides of the center of the polynucleotide probe. In particularly preferred probes, the biallelic marker is at the center of said polynucleotide. Preferred probes comprise a nucleotide sequence selected from the group consisting of Nos 9-27, 99-14387, 9-12, 9-13, 99-14405, and 9-16 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In preferred embodiments the polymorphic base is within 5, 4, 3, 2, 1, nucleotides of the center of the said polynucleotide, more preferably at the center of said polynucleotide.

Preferably the probes of the present invention are labeled or immobilized on a solid support. Labels and solid supports are further described in "Oligonucleotide Probes and Primers". The probes can be non-extendable as described in "Oligonucleotide Probes and Primers".

By assaying the hybridization to an allele specific probe, one can detect the presence or absence of a biallelic marker allele in a given sample. High-Throughput parallel hybridizations in array format are specifically encompassed within "hybridization assays" and are described below.

5) Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in *S. cerevisiae* mutant strains, and in the protease gene of HIV-1 virus (Hacia et al., 1996; Shoemaker et al., 1996; Kozal et al., 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which, target sequences include a polymorphic marker. EP 785280 describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of monomers, i.e. nucleotides. Tiling strategies are further described in PCT application No. WO 95/11995. In a particular aspect, arrays are tiled for a number of specific, identified biallelic marker sequences. In particular, the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424,186.

Thus, in some embodiments, the chips may comprise an array of nucleic acid sequences of fragments of about 15 nucleotides in length. In further embodiments, the chip may comprise an array including at least one of the sequences selected from the group consisting of 9-27, 99-14387, 9-12, 9-13, 99-14405, and 9-16 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In preferred embodiments the polymorphic base is within 5, 4, 3, 2, 1, nucleotides of the center of the said polynucleotide, more preferably at the center of said polynucleotide. In some embodiments, the chip may comprise an array of at least 2, 3, 4, 5, 6, 7, 8 or more of these polynucleotides of the invention. Solid supports and polynucleotides of the present invention attached to solid supports are further described in "oligonucleotide probes and primers".

6) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping biallelic markers, the microfluidic system may integrate nucleic acid amplification, microsequencing, capillary electrophoresis and a detection method such as laser-induced fluorescence detection. In a first step, the DNA samples are amplified, preferably by PCR. Then, the amplification products are subjected to automated microsequencing reactions using ddNTPs (specific fluorescence for each ddNTP) and the appropriate oligonucleotide microsequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can for example be polyacrylamide, polyethyleneglycol or dextran. The incorporated ddNTPs in the single-nucleotide primer extension products are identified by fluorescence detection. This microchip can be used to process at least 96 to 384 samples in parallel. It can use the usual four color laser induced fluorescence detection of the ddNTPs.

Methods of Genetic Analysis Using the Biallelic Markers of the Present Invention Different methods are available for the genetic analysis of complex traits (see Lander and Schork, 1994). The search for disease-susceptibility genes is conducted using two main methods: the linkage approach in which evidence is sought for cosegregation between a locus and a putative trait locus using family studies, and the association approach in which evidence is sought for a statistically significant association between an allele and a trait or a trait causing allele (Khoury et al., 1993). In general, the biallelic markers of the present invention find use in any method known in the art to demonstrate a statistically significant correlation between a genotype and a phenotype. The biallelic markers may be used in parametric and non-parametric linkage analysis methods. Preferably, the biallelic markers of the present invention are used to identify genes associated with detectable traits using association studies, an approach which does not require the use of affected families and which permits the identification of genes associated with complex and sporadic traits.

The genetic analysis using the biallelic markers of the present invention may be conducted on any scale. The whole set of biallelic markers of the present invention or any subset of biallelic markers of the present invention corresponding to the candidate gene may be used. Further, any set of genetic markers including a biallelic marker of the present invention may be used. A set of biallelic polymorphisms that could be used as genetic markers in combination with the biallelic markers of the present invention has been described in WO 98/20165. As mentioned above, it should be noted that the biallelic markers of the present invention may be included in any complete or partial genetic map of the human genome. These different uses are specifically contemplated in the present invention and claims.

The invention also comprises methods of detecting an association between a genotype and a phenotype, comprising the steps of a) genotyping at least one APM1-related biallelic marker in a trait positive population according to a genotyping method of the invention; b) genotyping said APM1-related biallelic marker in a control population according to a genotyping method of the invention; and c) determining whether a statistically significant association exists between said genotype and said phenotype. In addition, the methods of detecting an association between a genotype and a phenotype of the invention encompass methods with any further limitation described in this disclosure, or those following, specified alone or in any combination. Optionally, said APM1-related biallelic marker may be selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof; optionally, wherein said APM1-related biallelic marker is selected from the group consisting of A1, A2, and A7 or the group consisting of A4 and A8. Optionally, said control population may be a trait negative population, or a random population. Optionally, each of said genotyping steps a) and b) may be performed on a pooled biological sample derived from each of said populations. Optionally, each of said genotyping of steps a) and b) is performed separately on biological samples derived from each individual in said population or a subsample thereof. Optionally, said phenotype is obesity or disorders related to obesity. Optionally, wherein said disorder related to obesity is selected from the group consisting of atherosclerosis, insulin resistance, hypertension, hyperlipidemia, hypertriglyceridemia, cardiovascular disease, microangiopathic in obese individuals with Type II diabetes, ocular lesions associated with microangiopathy in obese individuals with Type II diabetes, renal lesions associated with microangiopathy in obese individuals with Type II diabetes, and Syndrome X.

The invention also encompasses methods of estimating the frequency of a haplotype for a set of biallelic markers in a population, comprising the steps of: a) genotyping at least two APM1-related biallelic marker for each individual in said population or a subsample thereof, according to a genotyping method of the invention; and b) applying a haplotype determination method to the identities of the nucleotides determined in steps a) to obtain an estimate of said frequency. In addition, the methods of estimating the frequency of a haplotype of the invention encompass methods with any further limitation described in this disclosure, or those following, specified alone or in any combination: Optionally, said biallelic marker may be selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof, optionally, wherein said APM1-related biallelic marker is selected from the group consisting of A1, A2, and A7 or the group consisting of A4 and A8. Optionally, said haplotype determination method is performed by asymmetric PCR amplification, double PCR amplification of specific alleles, the Clark algorithm, or an expectation-maximization algorithm.

An additional embodiment of the present invention encompasses methods of detecting an association between a haplotype and a phenotype, comprising the steps of: a) estimating the frequency of at least one haplotype in a trait positive population, according to a method of the invention for estimating the frequency of a haplotype; b) estimating the frequency of said haplotype in a control population, according to a method of the invention for estimating the frequency of a haplotype; and c) determining whether a statistically significant association exists between said haplotype and said phenotype. In addition, the methods of detecting an association between a haplotype and a phenotype of the invention encompass methods with any further limitation described in this disclosure, or those following. Optionally, said biallelic marker may be selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof, optionally, wherein said APM1-related biallelic marker is selected from the group consisting of A1, A2, and A7 or the group consisting of A4 and A8. Optionally, said control population is a trait negative population, or a random population. Optionally, said phenotype is obesity or a disorder related to obesity. Optionally, said method comprises the additional steps of determining the phenotype in said trait positive and said control populations prior to step c). Optionally, wherein said disorder related to obesity is selected from the group consisting of atherosclerosis, insulin resistance, hypertension, hyperlipidemia, hypertriglyceridemia, cardiovascular disease, microangiopathic in obese individuals with Type II diabetes, ocular lesions associated with microangiopathy in obese individuals with Type II diabetes, renal lesions associated with microangiopathy in obese individuals with Type II diabetes, and Syndrome X.

Linkage Analysis

Linkage analysis is based upon establishing a correlation between the transmission of genetic markers and that of a specific trait throughout generations within a family. Thus, the aim of linkage analysis is to detect marker loci that show cosegregation with a trait of interest in pedigrees.

Parametric Methods

When data are available from successive generations there is the opportunity to study the degree of linkage between pairs of loci. Estimates of the recombination fraction enable loci to be ordered and placed onto a genetic map. With loci that are genetic markers, a genetic map can be established, and then the strength of linkage between markers and traits can be calculated and used to indicate the relative positions of markers and genes affecting those traits (Weir, 1996). The classical method for linkage analysis is the logarithm of odds (lod) score method (see Morton, 1955; Ott, 1991). Calculation of lod scores requires specification of the mode of inheritance for the disease (parametric method). Generally, the length of the candidate region identified using linkage analysis is between 2 and 20 Mb. Once a candidate region is identified as described above, analysis of recombinant individuals using additional markers allows further delineation of the candidate region. Linkage analysis studies have generally relied on the use of a maximum of 5,000 microsatellite markers, thus limiting the maximum theoretical attainable resolution of linkage analysis to about 600 kb on average.

Linkage analysis has been successfully applied to map simple genetic traits that show clear Mendelian inheritance patterns and which have a high penetrance (i.e., the ratio between the number of trait positive carriers of allele a and the total number of a carriers in the population). However, parametric linkage analysis suffers from a variety of drawbacks. First, it is limited by its reliance on the choice of a genetic model suitable for each studied trait. Furthermore, as already mentioned, the resolution attainable using linkage analysis is limited, and complementary studies are required to refine the analysis of the typical 2 Mb to 20 Mb regions initially identified through linkage analysis. In addition, parametric linkage analysis approaches have proven difficult when applied to complex genetic traits, such as those due to the combined action of multiple genes and/or environmental factors. It is very difficult to model these factors adequately in a lod score analysis. In such cases, too large an effort and cost are needed to recruit the adequate number of affected families required for applying linkage analysis to these situations, as recently discussed by Risch, N. and Merikangas, K. (1996).

Non-Parametric Methods

The advantage of the so-called non-parametric methods for linkage analysis is that they do not require specification of the mode of inheritance for the disease, they tend to be more useful for the analysis of complex traits. In non-parametric methods, one tries to prove that the inheritance pattern of a chromosomal region is not consistent with random Mendelian segregation by showing that affected relatives inherit identical copies of the region more often than expected by chance. Affected relatives should show excess "allele sharing" even in the presence of incomplete penetrance and polygenic inheritance. In non-parametric linkage analysis the degree of agreement at a marker locus in two individuals can be measured either by the number of alleles identical by state (IBS) or by the number of alleles identical by descent (IBD). Affected sib pair analysis is a well-known special case and is the simplest form of these methods.

The biallelic markers of the present invention may be used in both parametric and non-parametric linkage analysis. Preferably biallelic markers may be used in non-parametric methods which allow the mapping of genes involved in complex traits. The biallelic markers of the present invention may be used in both IBD- and IBS-methods to map genes affecting a complex trait. In such studies, taking advantage of the high density of biallelic markers, several adjacent biallelic marker loci may be pooled to achieve the efficiency attained by multi-allelic markers (Zhao et al., 1998).

Population Association Studies

The present invention comprises methods for identifying if the APM1 gene is associated with a detectable trait using the biallelic markers of the present invention. In one embodiment the present invention comprises methods to detect an association between a biallelic marker allele or a biallelic marker haplotype and a trait. Further, the invention comprises methods to identify a trait causing allele in linkage disequilibrium with any biallelic marker allele of the present invention.

As described above, alternative approaches can be employed to perform association studies: genome-wide association studies, candidate region association studies and candidate gene association studies. In a preferred embodiment, the biallelic markers of the present invention are used to perform candidate gene association studies. The candidate gene analysis clearly provides a short-cut approach to the identification of genes and gene polymorphisms related to a particular trait when some information concerning the biology of the trait is available. Further, the biallelic markers of the present invention may be incorporated in any map of genetic markers of the human genome in order to perform genome-wide association studies. Methods to generate a high-density map of biallelic markers has been described in U.S. Provisional Patent application serial No. 60/082,614. The biallelic markers of the present invention may further be incorporated in any map of a specific candidate region of the genome (a specific chromosome or a specific chromosomal segment for example).

As mentioned above, association studies may be conducted within the general population and are not limited to studies performed on related individuals in affected families. Association studies are extremely valuable as they permit the analysis of sporadic or multifactor traits. Moreover, association studies represent a powerful method for fine-scale mapping enabling much finer mapping of trait causing alleles than linkage studies. Studies based on pedigrees often only narrow the location of the trait causing allele. Association studies using the biallelic markers of the present invention can therefore be used to refine the location of a trait causing allele in a candidate region identified by Linkage Analysis methods. Moreover, once a chromosome segment of interest has been identified, the presence of a candidate gene such as a candidate gene of the present invention, in the region of interest can provide a shortcut to the identification of the trait causing allele. Biallelic markers of the present invention can be used to demonstrate that a candidate gene is associated with a trait. Such uses are specifically contemplated in the present invention.

Determining the Frequency of a Biallelic Marker Allele or of a Biallelic Marker Haplotype in a Population Association studies explore the relationships among frequencies for sets of alleles between loci.

Determining the Frequency of an Allele in a Population

Allelic frequencies of the biallelic markers in a populations can be determined using one of the methods described above under the heading "Methods for genotyping an individual for biallelic markers", or any genotyping procedure suitable for this intended purpose. Genotyping pooled samples or individual samples can determine the frequency of a biallelic marker allele in a population. One way to reduce the number of genotypings required is to use pooled samples. A major obstacle in using pooled samples is in terms of accuracy and reproducibility for determining accurate DNA concentrations in setting up the pools. Genotyping individual samples provides higher sensitivity, reproducibility and accuracy and; is the preferred method used in the present invention. Preferably, each individual is genotyped separately and simple gene counting is applied to determine the frequency of an allele of a biallelic marker or of a genotype in a given population.

Determining the Frequency of a Haplotype in a Population

The gametic phase of haplotypes is unknown when diploid individuals are heterozygous at more than one locus. Using genealogical information in families gametic phase can sometimes be inferred (Perlin et al., 1994). When no genealogical information is available different strategies may be used. One possibility is that the multiple-site heterozygous diploids can be eliminated from the analysis, keeping only the homozygotes and the single-site heterozygote individuals, but this approach might lead to a possible bias in the sample composition and the underestimation of low-frequency haplotypes. Another possibility is that single chromosomes can be studied independently, for example, by asymmetric PCR amplification (see Newton et al, 1989; Wu et al., 1989) or by isolation of single chromosome by limit dilution followed by PCR amplification (see Ruano et al., 1990). Further, a sample may be haplotyped for sufficiently close biallelic markers by double PCR amplification of specific alleles (Sarkar, G. and Sommer S. S., 1991). These approaches are not entirely satisfying either because of their technical complexity, the additional cost they entail, their lack of generalization at a large scale, or the possible biases they introduce. To overcome these difficulties, an algorithm to infer the phase of PCR-amplified DNA genotypes introduced by Clark, A. G.(1990) may be used. Briefly, the principle is to start filling a preliminary list of haplotypes present in the sample by examining unambiguous individuals, that is, the complete homozygotes and the single-site heterozygotes. Then other individuals in the same sample are screened for the possible occurrence of previously recognized haplotypes. For each positive identification, the complementary haplotype is added to the list of recognized haplotypes, until the phase information for all individuals is either resolved or identified as unresolved. This method assigns a single haplotype to each multiheterozygous individual, whereas several haplotypes are possible when there are more than one heterozygous site. Alternatively, one can use methods estimating haplotype frequencies in a population without assigning haplotypes to each individual. Preferably, a method based on an expectation-maximization (EM) algorithm (Dempster et al., 1977) leading to maximum-likelihood estimates of haplotype frequencies under the assumption of Hardy-Weinberg proportions (random mating) is used (see Excoffier L. and Slatkin M., 1995). The EM algorithm is a generalized iterative maximum-likelihood approach to estimation that is useful when data are ambiguous and/or incomplete. The EM algorithm is used to resolve heterozygotes into haplotypes. Haplotype estimations are further described below under the heading "Statistical Methods." Any other method known in the art to determine or to estimate the frequency of a haplotype in a population may be used.

Linkage Disequilibrium Analysis

Linkage disequilibrium is the non-random association of alleles at two or more loci and represents a powerful tool for mapping genes involved in disease traits (see Ajioka R. S. et al., 1997). Biallelic markers, because they are densely spaced in the human genome and can be genotyped in greater numbers than other types of genetic markers (such as RFLP or VNTR markers), are particularly useful in genetic analysis based on linkage disequilibrium.

When a disease mutation is first introduced into a population (by a new mutation or the immigration of a mutation carrier), it necessarily resides on a single chromosome and thus on a single "background" or "ancestral" haplotype of linked markers. Consequently, there is complete disequilibrium between these markers and the disease mutation: one finds the disease mutation only in the presence of a specific set of marker alleles. Through subsequent generations recombination events occur between the disease mutation and these marker polymorphisms, and the disequilibrium gradually dissipates. The pace of this dissipation is a function of the recombination frequency, so the markers closest to the disease gene will manifest higher levels of disequilibrium than those that are further away. When not broken up by recombination, "ancestral" haplotypes and linkage disequilibrium between marker alleles at different loci can be tracked not only through pedigrees but also through populations. Linkage disequilibrium is usually seen as an association between one specific allele at one locus and another specific allele at a second locus.

The pattern or curve of disequilibrium between disease and marker loci is expected to exhibit a maximum that occurs at the disease locus. Consequently, the amount of linkage disequilibrium between a disease allele and closely linked genetic markers may yield valuable information regarding the location of the disease gene. For fine-scale mapping of a disease locus, it is useful to have some knowledge of the patterns of linkage disequilibrium that exist between markers in the studied region. As mentioned above the mapping resolution achieved through the analysis of linkage disequilibrium is much higher than that of linkage studies. The high density of biallelic markers combined with linkage disequilibrium analysis provides powerful tools for fine-scale mapping. Different methods to calculate linkage disequilibrium are described below under the heading "Statistical Methods".

Population-Based Case-Control Studies of Trait-Marker Associations

As mentioned above, the occurrence of pairs of specific alleles at different loci on the same chromosome is not random and the deviation from random is called linkage disequilibrium. Association studies focus on population frequencies and rely on the phenomenon of linkage disequilibrium. If a specific allele in a given gene is directly involved in causing a particular trait, its frequency will be statistically increased in an affected (trait positive) population, when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular region. Case-control populations can be genotyped for biallelic markers to identify associations that narrowly locate a trait causing allele. As any marker in linkage disequilibrium with one given marker associated with a trait will be associated with the trait. Linkage disequilibrium allows the relative frequencies in case-control populations of a limited number of genetic polymorphisms (specifically biallelic markers) to be analyzed as an alternative to screening all possible functional polymorphisms in order to find trait-causing alleles. Association studies compare the frequency of marker alleles in unrelated case-control populations, and represent powerful tools for the dissection of complex traits.

Case-Control Populations (Inclusion Criteria)

Population-based association studies do not concern familial inheritance but compare the prevalence of a particular genetic marker, or a set of markers, in case-control populations. They are case-control studies based on comparison of unrelated case (affected or trait positive) individuals and unrelated control (unaffected, trait negative or random) individuals. Preferably the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. The terms "trait positive population", "case population" and "affected population" are used interchangeably herein.

An important step in the dissection of complex traits using association studies is the choice of case-control populations (see Lander and Schork, 1994). A major step in the choice of case-control populations is the clinical definition of a given trait or phenotype. Any genetic trait may be analyzed by the association method proposed here by carefully selecting the individuals to be included in the trait positive and trait negative phenotypic groups. Four criteria are often useful: clinical phenotype, age at onset, family history and severity. The selection procedure for continuous or quantitative traits (such as blood pressure for example) involves selecting individuals at opposite ends of the phenotype distribution of the trait under study, so as to include in these trait positive and trait negative populations individuals with non-overlapping phenotypes. Preferably, case-control populations consist of phenotypically homogeneous populations. Trait positive and trait negative populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and preferably selected among individuals exhibiting non-overlapping phenotypes. The clearer the difference between the two trait phenotypes, the greater the probability of detecting an association with biallelic markers. The selection of those drastically different but relatively uniform phenotypes enables efficient comparisons in association studies and the possible detection of marked differences at the genetic level, provided that the sample sizes of the populations under study are significant enough.

In preferred embodiments, a first group of between 50 and 300 trait positive individuals, preferably about 100 individuals, are recruited according to their phenotypes. A similar number of trait negative individuals are included in such studies.

In the present invention, typical examples of inclusion criteria include obesity and disorders related to obesity.

Association Analysis

The general strategy to perform association studies using biallelic markers derived from a region carrying a candidate gene is to scan two groups of individuals (case-control populations) in order to measure and statistically compare the allele frequencies of the biallelic markers of the present invention in both groups.

If a statistically significant association with a trait is identified for at least one or more of the analyzed biallelic markers, one can assume that: either the associated allele is directly responsible for causing the trait (i.e. the associated allele is the trait causing allele), or more likely the associated allele is in linkage disequilibrium with the trait causing allele. The specific characteristics of the associated allele with respect to the candidate gene function usually give further insight into the relationship between the associated allele and the trait (causal or in linkage disequilibrium). If the evidence indicates that the associated allele within the candidate gene is most probably not the trait causing allele but is in linkage disequilibrium with the real trait causing allele, then the trait causing allele can be found by sequencing the vicinity of the associated marker, and performing further association studies with the polymorphisms that are revealed in an iterative manner.

Association studies are usually run in two successive steps. In a first phase, the frequencies of a reduced number of biallelic markers from the candidate gene are determined in the trait positive and trait negative populations. In a second phase of the analysis, the position of the genetic loci responsible for the given trait is further refined using a higher density of markers from the relevant region. However, if the candidate gene under study is relatively small in length, as is the case for APM1, a single phase may be sufficient to establish significant associations.

Haplotype Analysis

As described above, when a chromosome carrying a disease allele first appears in a population as a result of either mutation or migration, the mutant allele necessarily resides on a chromosome having a set of linked markers: the ancestral haplotype. This haplotype can be tracked through populations and its statistical association with a given trait can be analyzed. Complementing single point (allelic) association studies with multi-point association studies also called haplotype studies increases the statistical power of association studies. Thus, a haplotype association study allows one to define the frequency and the type of the ancestral carrier haplotype. A haplotype analysis is important in that it increases the statistical power of an analysis involving individual markers.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals, which should be, subjected to this analysis to obtain statistically significant results usually ranges between 30 and 300, with a preferred number of individuals ranging between 50 and 150. The same considerations apply to the number of unaffected individuals (or random control) used in the study. The results of this first analysis provide haplotype frequencies in case-control populations, for each evaluated haplotype frequency a p-value and an odd ratio are calculated. If a statistically significant association is found the relative risk for an individual carrying the given haplotype of being affected with the trait under study can be approximated.

Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis. Interaction analysis consists in stratifying the case-control populations with respect to a given haplotype for the first loci and performing a haplotype analysis with the second loci with each subpopulation.

Statistical Methods Used in Association Studies

Testing for Linkage in the Presence of Association

The biallelic markers of the present invention may further be used in TDT (transmission/disequilibrium test). TDT tests for both linkage and association and is not affected by population stratification. TDT requires data for affected individuals and their parents or data from unaffected sibs instead of from parents (see Spielmann S. et al., 1993; Schaid D. J. et al., 1996, Spielmann S. and Ewens W. J., 1998). Such combined tests generally reduce the false—positive errors produced by separate analyses.

Statistical Methods

In general, any method known in the art to test whether a trait and a genotype show a statistically significant correlation may be used.

1) Methods in Linkage Analysis

Statistical methods and computer programs useful for linkage analysis are well-known to those skilled in the art (see Terwilliger J. D. and Ott J., 1994; Ott J., 1991).

2) Methods to Estimate Haplotype Frequencies in a Population

As described above, when genotypes are scored, it is often not possible to distinguish heterozygotes so that haplotype frequencies cannot be easily inferred. When the gametic phase is not known, haplotype frequencies can be estimated from the multilocus genotypic data. Any method known to person skilled in the art can be used to estimate haplotype frequencies (see Lange K., 1997; Weir, B. S., 1996) Preferably, maximum-likelihood haplotype frequencies are computed using an Expectation-Maximization (EM) algorithm (see Dempster et al., 1977; Excoffier L. and Slatkin M., 1995). This procedure is an iterative process aiming at obtaining maximum-likelihood estimates of haplotype frequencies from multi-locus genotype data when the gametic phase is unknown. Haplotype estimations are usually performed by applying the EM algorithm using for example the EM-HAPLO program (Hawley M. E. et al., 1994) or the Arlequin program (Schneider et al., 1997). The EM algorithm is a generalized iterative maximum likelihood approach to estimation and is briefly described below.

Please note that in the present section, "Methods To Estimate Haplotype Frequencies In A Population," of this text, phenotypes will refer to multi-locus genotypes with unknown phase. Genotypes will refer to known-phase multi-locus genotypes.

A sample of N unrelated individuals is typed for K markers. The data observed are the unknown-phase K-locus phenotypes that can categorized in F different phenotypes. Suppose that we have H underlying possible haplotypes (in case of K biallelic markers, $H=2^K$).

For phenotype j, suppose that $c_j$ genotypes are possible. We thus have the following equation $$P_j = \sum_{i=1}^{c_j} pr(genotype_i) = \sum_{i=1}^{c_j} pr(h_k, h_l) \qquad \text{Equation 1}$$

where Pj is the probability of the phenotypes j, $h_k$ and $h_l$ are the two haplotypes constituent the genotype i. Under the Hardy-Weinberg equilibrium, $pr(h_k,h_l)$ becomes:

$$pr(h_k,h_l)=pr(h_k)^2 \text{ if } h_k=h_l,$$
$$pr(h_k,h_l)=2pr(h_k).pr(h_l) \text{ if } h_k \neq h_l. \qquad \text{Equation 2}$$

The successive steps of the E-M algorithm can be described as follows:

Starting with initial values of the of haplotypes frequencies, noted $p_1^{(0)}, p_2^{(0)}, \ldots p_H^{(0)}$, these initial values serve to estimate the genotype frequencies (Expectation step) and then estimate another set of haplotype frequencies (Maximization step), noted $p_1^{(1)}, p_2^{(1)}, \ldots p_H^{(1)}$, these two steps are iterated until changes in the sets of haplotypes frequency are very small.

A stop criterion can be that the maximum difference between haplotype frequencies between two iterations is less than $10^{-7}$. These values can be adjusted according to the desired precision of estimations.

At a given iteration s, the Expectation step consists in calculating the genotypes frequencies by the following equation:

$$pr(genotype_i)^{(s)} = pr(phenotype_j) \cdot \qquad \text{Equation 3}$$
$$pr(genotype_i \mid phenotype_j)^{(s)}$$
$$= \frac{n_j}{N} \cdot \frac{pr(h_k, h_l)^{(s)}}{P_j^{(s)}}$$

where genotype i occurs in phenotype j, and where $h_k$ and $h_l$ constitute genotype i. Each probability is derived according to eq. 1, and eq. 2 described above.

Then the Maximization step simply estimates another set of haplotype frequencies given the genotypes frequencies. This approach is also known as the gene-counting method (Smith, 1957).

$$p_t^{(s+1)} = \frac{1}{2} \sum_{j=1}^{F} \sum_{i=1}^{c_j} \delta_{it} \cdot pr(genotype_i)^{(s)} \qquad \text{Equation 4}$$

Where $\delta_{it}$ is an indicator variable which count the number of time haplotype t in genotype i. It takes the values of 0, 1 or 2.

To ensure that the estimation finally obtained is the maximum-likelihood estimation several values of departures are required. The estimations obtained are compared and if they are different the estimations leading to the best likelihood are kept.

3) Methods to Calculate Linkage Disequilibrium Between Markers

A number of methods can be used to calculate linkage disequilibrium between any two genetic positions, in practice linkage disequilibrium is measured by applying a statistical association test to haplotype data taken from a population.

Linkage disequilibrium between any pair of biallelic markers comprising at least one of the biallelic markers of the present invention $(M_i, M_j)$ having alleles $(a_i/b_i)$ at marker $M_i$ and alleles $(a_j/b_j)$ at marker $M_j$ can be calculated for every allele combination $(a_i,a_j; a_i,b_j; b_i,a_j$ and $b_i,b_j)$, according to the Piazza formula:

$$\Delta_{aiaj}=\sqrt{\theta 4}-\sqrt{(\theta 4+\theta 3)(\theta 4+\theta 2)},$$

where:

$\theta 4=---$=frequency of genotypes not having allele $a_i$ at $M_i$ and not having allele $a_j$ at $M_j$ $\theta 3=-+$=frequency of genotypes not having allele $a_{i \, at \, Mi}$ and having allele $a_j$ at $M_j$ $\theta 2=+-$=frequency of genotypes having allele $a_i$ at $M_i$ and not having allele $a_j$ at $M_j$ Linkage disequilibrium (LD) between pairs of biallelic markers $(M_i, M_j)$ can also be calculated for every allele combination (ai,aj; ai,bj; $b_i,a_j$ and $b_i,b_j$), according to the maximum-likelihood estimate (MLE) for delta (the composite genotypic disequilibrium coefficient), as described by Weir (Weir B. S., 1996). The MLE for the composite linkage disequilibrium is:

$$D_{aiaj}=(2n_1+n_2+n_3+n_4/2)/N-2(pr(a_i).pr(a_j))$$

Where $n_1=\Sigma$ phenotype $(a_i/a_i, a_j/a_j)$, $n_2=\Sigma$ phenotype $(a_i/a_i, a_j/b_j)$, $n_3=\Sigma$ phenotype $(a_i/b_i, a_j/a_j)$, $n_4=\Sigma$ phenotype $(a_i/b_i, a_j/b_j)$ and N is the number of individuals in the sample.

This formula allows linkage disequilibrium between alleles to be estimated when only genotype, and not haplotype, data are available.

Another means of calculating the linkage disequilibrium between markers is as follows. For a couple of biallelic markers, $M_i$ $(a_i/b_i)$ and $M_j$ $(a_j/b_j)$, fitting the Hardy-Weinberg equilibrium, one can estimate the four possible haplotype frequencies in a given population according to the approach described above.

The estimation of gametic disequilibrium between ai and aj is simply:

$$D_{aiaj}=pr(\text{haplotype}(a_i, a_j))-pr(a_i).pr(a_j).$$

Where $pr(a_i)$ is the probability of allele $a_i$ and $pr(a_j)$ is the probability of allele $a_j$ and where $pr(\text{haplotype }(a_i, a_j))$ is estimated as in Equation 3 above.

For a couple of biallelic marker only one measure of disequilibrium is necessary to describe the association between $M_i$ and $M_j$.

Then a normalized value of the above is calculated as follows:

$$D'_{aiaj}=D_{aiaj}/\max(-pr(a_i).pr(a_j), -pr(b_i).pr(b_j)) \text{ with } D_{aiaj}<0$$

$$D'_{aiaj}=D_{aiaj}/\max(pr(b_i).pr(a_j), pr(a_i).pr(b_j)) \text{ with } D_{aiaj}>0$$

The skilled person will readily appreciate that other LD calculation methods can be used.

Linkage disequilibrium among a set of biallelic markers having an adequate heterozygosity rate can be determined by genotyping between 50 and 1000 unrelated individuals, preferably between 75 and 200, more preferably around 100.

4) Testing for Association

Methods for determining the statistical significance of a correlation between a phenotype and a genotype, in this case an allele at a biallelic marker or a haplotype made up of such alleles, may be determined by any statistical test known in the art and with any accepted threshold of statistical significance being required. The application of particular methods and thresholds of significance are well with in the skill of the ordinary practitioner of the art.

Testing for association is performed by determining the frequency of a biallelic marker allele in case and control populations and comparing these frequencies with a statistical test to determine if their is a statistically significant difference in frequency which would indicate a correlation between the trait and the biallelic marker allele under study. Similarly, a haplotype analysis is performed by estimating the frequencies of all possible haplotypes for a given set of biallelic markers in case and control populations, and comparing these frequencies with a statistical test to determine if their is a statistically significant correlation between the haplotype and the phenotype (trait) under study. Any statistical tool useful to test for a statistically significant association between a genotype and a phenotype may be used. Preferably the statistical test employed is a chi-square test with one degree of freedom. A P-value is calculated (the P-value is the probability that a statistic as large or larger than the observed one would occur by chance).

Statistical Significance

In preferred embodiments, significance for diagnosis purposes, either as a positive basis for further diagnostic tests or as a preliminary starting point for early preventive therapy, the p value related to a biallelic marker association is preferably about $1\times10^{-2}$ or less, more preferably about $1\times10^{-4}$ or less, for a single biallelic marker analysis and about $1\times10^{-3}$ or less, still more preferably $1\times10^{-6}$ or less and most preferably of about $1\times10^{-8}$ or less, for a haplotype analysis involving two or more markers. These values are believed to be applicable to any association studies involving single or multiple marker combinations.

The skilled person can use the range of values set forth above as a starting point in order to carry out association studies with biallelic markers of the present invention. In doing so, significant associations between the biallelic markers of the present invention and obesity or disorders related to obesity can be revealed and used for diagnosis and drug screening purposes.

Phenotypic Permutation

In order to confirm the statistical significance of the first stage haplotype analysis described above, it might be suitable to perform further analyses in which genotyping data from case-control individuals are pooled and randomized with respect to the trait phenotype. Each individual genotyping data is randomly allocated to two groups, which contain the same number of individuals as the case-control populations used to compile the data obtained in the first stage. A second stage haplotype analysis is preferably run on these artificial groups, preferably for the markers included in the haplotype of the first stage analysis showing the highest relative risk coefficient. This experiment is reiterated preferably at least between 100 and 10000 times. The repeated iterations allow the determination of the percentage of obtained haplotypes with a significant p-value level below about $1\times10^{-3}$.

Assessment of Statistical Association

To address the problem of false positives similar analysis may be performed with the same case-control populations in random genomic regions. Results in random regions and the candidate region are compared as described in a co-pending U.S. Provisional Patent Application entitled "Methods, Software And Apparati For Identifying Genomic Regions Harboring A Gene Associated With A Detectable Trait," U.S. Ser. No. 60/107,986, filed Nov. 10, 1998, the contents of which are incorporated herein by reference.

5) Evaluation of Risk Factors

The association between a risk factor (in genetic epidemiology the risk factor is the presence or the absence of a certain allele or haplotype at marker loci) and a disease is measured by the odds ratio (OR) and by the relative risk (RR). If $P(R^+)$ is the probability of developing the disease for individuals with R and $P(R^-)$ is the probability for individuals without the risk factor, then the relative risk is simply the ratio of the two probabilities, that is:

$$RR=P(R^+)/P(R^-)$$

In case-control studies, direct measures of the relative risk cannot be obtained because of the sampling design. However, the odds ratio allows a good approximation of the relative risk for low-incidence diseases and can be calculated:

$$OR=(F^+/(1-F^+))/(F^-/(1-F^-))$$

$F^+$ is the frequency of the exposure to the risk factor in cases and $F^-$ is the frequency of the exposure to the risk factor in controls. $F^+$ and $F^-$ are calculated using the allelic or haplotype frequencies of the study and further depend on the underlying genetic model (dominant, recessive, additive, etc).

One can further estimate the attributable risk (AR) which describes the proportion of individuals in a population exhibiting a trait due to a given risk factor. This measure is important in quantifying the role of a specific factor in disease etiology and in terms of the public health impact of a risk factor. The public health relevance of this measure lies in estimating the proportion of cases of disease in the population that could be prevented if the exposure of interest were absent. AR is determined as follows:

$$AR=P_E(RR-1)/(P_E(RR-1)+1)$$

AR is the risk attributable to a biallelic marker allele or a biallelic marker haplotype. $P_E$ is the frequency of exposure to an allele or a haplotype within the population at large; and RR is the relative risk which, is approximated with the odds ratio when the trait under study has a relatively low incidence in the general population.

Identification of Biallelic Markers in Linkage Disequilibrium with the Biallelic Markers of the Invention Once a first biallelic marker has been identified in a genomic region of interest, the practitioner of ordinary skill in the art, using the teachings of the present invention, can easily identify additional biallelic markers in linkage disequilibrium with this first marker. As mentioned before any marker in linkage disequilibrium with a first marker associated with a trait will be associated with the trait. Therefore, once an association has been demonstrated between a given biallelic marker and a trait, the discovery of additional biallelic markers associated with this trait is of great interest in order to increase the density of biallelic markers in this particular region. The causal gene or mutation will be found in the vicinity of the marker or set of markers showing the highest correlation with the trait.

Identification of additional markers in linkage disequilibrium with a given marker involves:

(a) amplifying a genomic fragment comprising a first biallelic marker from a plurality of individuals;

(b) identifying of second biallelic markers in the genomic region harboring said first biallelic marker;

(c) conducting a linkage disequilibrium analysis between said first biallelic marker and second biallelic markers; and (d) selecting said second biallelic markers as being in linkage disequilibrium with said first marker. Sub-combinations comprising steps (b) and (c) are also contemplated.

Methods to identify biallelic markers and to conduct linkage disequilibrium analysis are described herein and can be carried out by the skilled person without undue experimentation. The present invention then also concerns biallelic markers which are in linkage disequilibrium with the specific biallelic markers A1, A2, A3, A4, A5, A6, A7, A8, A9, A10, A11, A12, A13, A14, A15, A16, A17, A18, A19, A20, A21, A22, A23, A24, A25 and A26 and which are expect similar characteristics in terms of their respective association with a given trait; optionally, wherein said APM1-related biallelic marker is selected from the group consisting of A1, A2, and A7 or the group consisting of A4 and A8.

Mapping Studies: Identification of Functional Mutations

Once a positive association is confirmed with a biallelic marker of the present invention, gene in the associated candidate region (within linkage disequillibrium of the APM1 gene) can be scanned for mutations by comparing the sequences of a selected number of trait positive and trait negative individuals. In a preferred embodiment, functional regions such as exons and splice sites, promoters and other regulatory regions of the APM1 gene are scanned for mutations. Preferably, trait positive individuals carry the haplotype shown to be associated with the trait, and trait negative individuals do not carry the haplotype or allele associated with the trait. The mutation detection procedure is essentially similar to that used for biallelic site identification.

The method used to detect such mutations generally comprises the following steps: (a) amplification of a region of the candidate gene comprising a biallelic marker or a group of biallelic markers associated with the trait from DNA samples of trait positive patients and trait negative controls; (b) sequencing of the amplified region; (c) comparison of DNA sequences from trait-positive patients and trait-negative controls; and (d) determination of mutations specific to trait-positive patients. Subcombinations which comprise steps (b) and (c) are specifically contemplated.

It is preferred that candidate polymorphisms be then verified by screening a larger population of cases and controls by means of any genotyping procedure such as those described herein, preferably using a microsequencing technique in an individual test format. Polymorphisms are considered as candidate mutations when present in cases and controls at frequencies compatible with the expected association results.

Biallelic Markers of the Invention in Methods of Genetic Diagnostics

The biallelic markers of the present invention can also be used to develop diagnostic tests capable of identifying individuals who express a detectable trait as the result of a specific genotype or individuals whose genotype places them at risk of developing a detectable trait at a subsequent time.

It will of course be understood by practitioners skilled in the treatment or diagnosis of obesity and disorders related to obesity that the present invention does not intend to provide an absolute identification of individuals who could be at risk of developing a particular disease involving obesity and disorders related to obesity but rather to indicate a certain degree or likelihood of developing a disease. However, this information is extremely valuable as it can, in certain circumstances, be used to initiate preventive treatments or to allow an individual carrying a significant haplotype to foresee warning signs such as minor symptoms. In diseases in which attacks may be extremely violent and sometimes fatal if not treated on time, the knowledge of a potential predisposition, even if this predisposition is not absolute, might contribute in a very significant manner to treatment efficacy.

The diagnostic techniques of the present invention may employ a variety of methodologies to determine whether a test subject has a biallelic marker pattern associated with an increased risk of developing a detectable trait or whether the individual suffers from a detectable trait as a result of a particular mutation, including methods which enable the analysis of individual chromosomes for haplotyping, such as family studies, single sperm DNA analysis or somatic hybrids. The trait analyzed using the present diagnostics may be any detectable trait, including obesity and disorders related to obesity.

Another aspect of the present invention relates to a method of determining whether an individual is at risk of developing a trait or whether an individual expresses a trait as a consequence of possessing a particular trait-causing allele. The present invention also relates to a method of determining whether an individual is at risk of developing a plurality of traits or whether an individual expresses a plurality of traits as a result of possessing a particular trait-causing allele. These methods involve obtaining a nucleic acid sample from the individual and determining whether the nucleic acid sample contains one or more alleles of one or more biallelic markers indicative of a risk of developing the trait or indicative that the individual expresses the trait as a result of possessing a particular trait-causing allele. These methods also involve obtaining a nucleic acid sample from the individual and, determining, whether the nucleic acid sample contains at least one allele or at least one biallelic marker haplotype, indicative of a risk of developing the trait or indicative that the individual expresses the trait as a result of possessing a particular APM1 polymorphism or mutation (trait-causing allele).

Preferably, in such diagnostic methods, a nucleic acid sample is obtained from the individual and this sample is genotyped using methods described above in "Methods Of Genotyping DNA Samples For Biallelic markers. The diagnostics may be based on a single biallelic marker or on a group of biallelic markers. In each of these methods, a nucleic acid sample is obtained from the test subject and the biallelic marker pattern of one or more of the biallelic markers A1 to A26 is determined. Alternatively, the one or more biallelic markers are selected from the group consisting of A1, A2, A4, A7, and A8. Alternatively, one or more biallelic markers are selected from the group consisting of A1, A2, and A7.

In one embodiment, a PCR amplification is conducted on the nucleic acid sample to amplify regions in which polymorphisms associated with a detectable phenotype have been identified. The amplification products are sequenced to determine whether the individual possesses one or more APM1 polymorphisms associated with a detectable phenotype. The primers used to generate amplification products may comprise the primers listed in Table 1. Alternatively, the nucleic acid sample is subjected to microsequencing reactions as described above to determine whether the individual possesses one or more APM1 polymorphisms associated with a detectable phenotype resulting from a mutation or a polymorphism in the APM1 gene. The primers used in the microsequencing reactions may include the primers listed in Table 4.

In another embodiment, the nucleic acid sample is contacted with one or more allele specific oligonucleotide probes which specifically hybridize to one or more APM1 alleles associated with a detectable phenotype. The probes used in the hybridization assay may include the probes listed in Table 3. In another embodiment, the nucleic acid sample is contacted with a second APM1 oligonucleotide capable of producing an amplification product when used with the allele specific oligonucleotide in an amplification reaction. The presence of an amplification product in the amplification reaction indicates that the individual possesses one or more APM1 alleles associated with a detectable phenotype.

As described herein, the diagnostics may be based on a single biallelic marker or a group of biallelic markers. Preferably, the biallelic marker or combination of biallelic makers is selected from the group consisting of A1 to A26 and the complements thereof or any combination or subset thereof. More preferably, the one or more biallelic markers are selected from the group consisting of A1, A2, A4, A7, and A8, and the complements thereof or any combination or subset thereof. Alternatively, the one or more biallelic markers are selected from the group consisting of A1, A2, and A7. Diagnostic kits comprise any of the polynucleotides of the present invention.

These diagnostic methods are extremely valuable as they can, in certain circumstances, be used to initiate preventive treatments or to allow an individual carrying a significant genotype or haplotype to foresee warning signs such as minor symptoms. For example, in the study described in Example 6, the subjects were all adolescent girls who did not yet have significant disease. However, by identifying the girls as adolescents who are at risk for obesity and obesity-related diseases and disorders later in their life, they could be targeted now for more intensive treatment to prevent the onset of later severe disease, such as diabetes, or cardiovascular complications, or any of the other obesity-related diseases discussed herein. An association has been shown between APM1 markers and indicators of obesity and diabetes, specifically, as well as indicating susceptibility to other related diseases (Example 6).

Diagnostics, which analyze and predict response to a drug or side effects to a drug, may be used to determine whether an individual should be treated with a particular drug. For example, if the diagnostic indicates a likelihood that an individual will respond positively to treatment with a particular drug, the drug may be administered to the individual. Conversely, if the diagnostic indicates that an individual is likely to respond negatively to treatment with a particular drug, an alternative course of treatment may be prescribed. A negative response may be defined as either the absence of an efficacious response or the presence of toxic side effects. For example, in the study described in Example 6, the identified APM1 markers would be useful for genotyping a population of obese people to determine which people are more likely to be susceptibile to drugs designed to lower leptin levels or free fatty acid levels. Other associations between APM1 markers and other traits associated with obesity can also be determined using the methods of the invention without undue experimentation and would indicate other markers useful to identify sub-populations of people likely to be susceptible (or not) to a drug targeting those traits. In addition, specific associations can be performed looking at drug outcome (treatment/side effect) to identify other useful markers for predicting risks/successful treatment.

Clinical drug trials represent another application for the markers of the present invention. One or more markers indicative of response to an agent acting against an obesity-related disease or to side effects to an agent acting against an obesity-related disease may be identified using the methods described above. Thereafter, potential participants in clinical trials of such an agent may be screened to identify those individuals most likely to respond favorably to the drug and/or exclude those likely to experience side effects. In that way, the effectiveness of drug treatment may be measured in individuals who have the potential to respond positively to the drug, without lowering the measurement as a result of the inclusion of individuals who are unlikely to respond positively in the study and/or without risking undesirable safety problems.

Based on Example 6, herein, subgroups for clinical trials could be identified that had the rare allele of biallelic markers A1 and/or A2, any or all of the biallelic markers A4, A7 and A8, or both sets of biallelic markers. The first set of markers was shown to be associated with increased leptin levels, and the second set was associated with higher free fatty acid levels in obese girls. Having the rare allele from either of the sets of markers indicated a higher risk of obesity in later life compared with a group of individuals who remained thin throughout life with the same ethnicity background (data not shown). Thus these markers can be used to predict patients who might be susceptible to drugs designed to target/ameliorate these symptoms.

Obviously, the methods of the invention can be used to identify other markers and find other associations with traits associated with obesity such as hypertriglyceridemia, or hypertension, for example.

Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism.

The present invention encompasses a family of recombinant vectors that comprise a regulatory polynucleotide derived from the APM1 genomic sequence, or a coding polynucleotide from the APM1 genomic sequence. Consequently, the present invention further deals with a recombinant vector comprising either a regulatory polynucleotide comprised in the nucleic acids of SEQ ID Nos 2 and 3 or a polynucleotide comprising the APM1 coding sequence or both.

In a first preferred embodiment, a recombinant vector of the invention is used to amplify the inserted polynucleotide derived from a APM1 genomic sequence selected from the group consisting of the nucleic acids of SEQ ID No 1, 2 and 3 or a APM1 cDNA, for example the cDNA of SEQ ID NO 5 in a suitable cell host, this polynucleotide being amplified at every time that the recombinant vector replicates.

Generally, a recombinant vector of the invention may comprise any of the polynucleotides described herein, including regulatory sequences and coding sequences, as well as any APM1 primer or probe as defined above.

A second preferred embodiment of the recombinant vectors according to the invention consists of expression vectors comprising either a regulatory polynucleotide or a coding nucleic acid of the invention, or both. Within certain embodiments, expression vectors are employed to express the APM1 polypeptide which can be then purified and, for example be used in ligand screening assays or as an immunogen in order to raise specific antibodies directed against the APM1 protein. In other embodiments, the expression vectors are used for constructing transgenic animals and also for gene therapy. Expression requires that appropriate signals are provided in the vectors, said signals including various regulatory elements, such as enhancers/promoters from both viral and mammalian sources that drive expression of the genes of interest in host cells. Dominant drug selection markers for establishing permanent, stable cell clones expressing the products are generally included in the expression vectors of the invention, as they are elements that link expression of the drug selection markers to expression of the polypeptide.

More particularly, the present invention relates to expression vectors which include nucleic acids encoding a APM1 protein, preferably the APM1 protein of the amino acid sequence of SEQ ID No 6 or variants or fragments thereof, under the control of a regulatory sequence selected among the APM1 regulatory polynucleotides, or alternatively under the control of an exogenous regulatory sequence.

Consequently, preferred expression vectors of the invention are selected from the group consisting of: (a) the APM1 regulatory sequence comprised therein drives the expression of a coding polynucleotide operably linked thereto; (b) the APM1 coding sequence is operably linked to regulation sequences allowing its expression in a suitable cell host and/or host organism.

A recombinant expression vector comprising a nucleic acid selected from the group consisting of SEQ ID No 2, or biologically active fragments or variants thereof, is also part of the present invention.

In a preferred embodiment, a recombinant expression vector of the invention comprises a regulatory nucleotide sequence selected from the group consisting of:

(i) a nucleotide sequence comprising a polynucleotide of SEQ ID NO 2 or a complementary sequence thereto;

(ii) a nucleotide sequence comprising a polynucleotide having at least 95% of nucleotide identity with the nucleotide sequence of SEQ ID No 2 or a complementary sequence thereto;

(iii) a nucleotide sequence comprising a polynucleotide that hybridizes under stringent hybridization conditions with the nucleotide sequence of SEQ ID No 2 or a complementary sequence thereto; and (iv) a biologically active fragment or variant of the polynucleotides in (i), (ii) and (iii).

The invention also encompasses a recombinant expression vector comprising:

a) a nucleic acid comprising a regulatory nucleotide sequence selected from the group consisting of:
 (i) a nucleotide sequence comprising a polynucleotide of SEQ ID NO 2 or a complementary sequence thereto;
 (ii) a nucleotide sequence comprising a polynucleotide having at least 95% of nucleotide identity with the nucleotide sequence of SEQ ID No 2 or a complementary sequence thereto;
 (iii) a nucleotide sequence comprising a polynucleotide that hybridizes under stringent hybridization conditions with the nucleotide sequence of SEQ ID No 2 or a complementary sequence thereto; and
 (iv) a biologically active fragment or variant of the polynucleotides in (i), (ii) and (iii); and b) a polynucleotide encoding a desired polypeptide or nucleic acid of interest, operably linked to the nucleic acid defined in (a) above.

Additionally, the recombinant expression vector described above may also comprise a nucleic acid comprising a 3'-regulatory polynucleotide, preferably a 3'-regulatory polynucleotide of the APM1 gene. The APM1 3'-regulatory polynucleotide may also comprise the 3'-UTR sequence contained in the nucleotide sequence of SEQ ID NO 5.

The 5'-regulatory polynucleotide may also include the 5'-UTR sequence of the APM1 cDNA, or a biologically active fragment or variant thereof.

The invention also pertains to a recombinant expression vector useful for the expression of the APM1 coding sequence, wherein said vector comprises a nucleic acid of SEQ ID No 5.

Another preferred recombinant expression vector consists of a vector for expressing a APM1 coding sequence, wherein said vector comprises a nucleic acid of SEQ ID No 1 or a fragment thereof or a nucleic acid having at least 95% nucleotide identity with a polynucleotide of SEQ ID No 1 or a fragment thereof.

Recombinant vectors comprising a nucleic acid containing a APM1-related biallelic marker is also part of the invention. In a preferred embodiment, said biallelic marker is selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof; optionally, wherein said APM1-related biallelic marker is selected from the group consisting of A1, A2, and A7 or the group consisting of A4 and A8.

Some of the elements which can be found in the vectors of the present invention are described in further detail in the following sections.

1. General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may consist of a chromosomal, non-chromosomal, semi-synthetic and synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosoine binding sites, polyadenylation site, splice donor and acceptor sites, transcriptional termination sequences, and 5'-flanking nontranscribed sequences. DNA sequences derived from the SV40 viral genome, for example SV40 origin, early promoter, enhancer, splice and polyadenylation sites may be used to provide the required non-transcribed genetic elements.

The in vivo expression of a APM1 polypeptide of SEQ ID No 6 or fragments or variants thereof may be useful in order to correct a genetic defect related to the expression of the native gene in a host organism or to the production of a biologically inactive APM1 protein.

Consequently, the present invention also deals with recombinant expression vectors mainly designed for the in vivo production of the APM1 polypeptide of SEQ ID No 6 or fragments or variants thereof by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

2. Regulatory Elements Promoters

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., 1983; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic engineering (Sambrook et al.(1989) And Fuller et al. (1996)).

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

The vector containing the appropriate DNA sequence as described above, more preferably APM1 gene regulatory polynucleotide, a polynucleotide encoding the APM1 polypeptide selected from the group consisting of SEQ ID No 1 or a fragment or a variant thereof and SEQ ID No 5, or both of them, can be utilized to transform an appropriate host to allow the expression of the desired polypeptide or polynucleotide.

3. Selectable Markers

Selectable markers confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

3. Preferred Vectors

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Bacteriophage Vectors

The P1 bacteriophage vector may contain large inserts ranging from about 80 to about 100 kb.

The construction of P1 bacteriophage vectors such as p158 or p158/neo8 are notably described by Sternberg (1992, 1994). Recombinant P1 clones comprising APM1 nucleotide sequences may be designed for inserting large polynucleotides of more than 40 kb (Linton et al., 1993). To generate P1 DNA for transgenic experiments, a preferred protocol is the protocol described by McCormick et al. (1994). Briefly, *E. coli* (preferably strain NS3529) harboring the P1 plasmid are grown overnight in a suitable broth medium containing 25 µg/ml of kanamycin. The P1 DNA is prepared from the *E. coli* by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

To express a P1 clone comprising APM1 nucleotide sequences in a transgenic animal, typically transgenic mice, it is desirable to remove vector sequences from the P1 DNA fragment, for example by cleaving the P1 DNA at rare-cutting sites within the P1 polylinker (Sfil, NAotI or SalI). The P1 insert is then purified from vector sequences on a pulsed-field agarose gel, using methods similar using methods similar to those originally reported for the isolation of DNA from YACs (Schedl et al., 1993a; Peterson et al., 1993). At this stage, the resulting purified insert DNA can be concentrated, if necessary, on a Millipore Ultrafree-MC Filter Unit (Millipore, Bedford, Mass., USA—30,000 molecular weight limit) and then dialyzed against microinjection buffer (10 mM Tris-HCl, pH 7.4; 250 µM EDTA) containing 100 mM NaCl, 30 µM spermine, 70 µM spermidine on a microdyalisis membrane (type VS, 0.025 µM from Millipore). The intactness of the purified P1 DNA insert is assessed by electrophoresis on 1% agarose (Sea Kem GTG; FMC Bio-products) pulse-field gel and staining with ethidium bromide.

Baculovirus Vectors

A suitable vector for the expression of the APM1 polypeptide of SEQ ID No 6 or fragments or variants thereof is a baculovirus vector that can be propagated in insect cells and in insect cell lines. A specific suitable host vector system is the pVL 1392/1393 baculovirus transfer vector (Pharmingen) that is used to transfect the SF9 cell line (ATCC N° CRL 1711) which is derived from *Spodoptera frugiperda*.

Other suitable vectors for the expression of the APM1 polypeptide of SEQ ID No 6 or fragments or variants thereof in a baculovirus expression system include those described by Chai et al.(1993), Vlasak et al.(1983) and Lenhard et al.(1996).

Viral Vectors

In one specific embodiment, the vector is derived from an adenovirus. Preferred adenovirus vectors according to the invention are those described by Feldman and Steg (1996) or Ohno et al.(1994). Another preferred recombinant adenovirus according to this specific embodiment of the present invention is the human adenovirus type 2 or 5 (Ad 2 or Ad 5) or an adenovirus of animal origin (French patent application N° FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., 1989, Julan et al., 1992 and Neda et al., 1991.

Yet another viral vector system that is contemplated by the invention consists in the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

BAC Vectors

The bacterial artificial chromosome (BAC) cloning system (Shizuya et al., 1992) has been developed to stably maintain large fragments of genomic DNA (100–300 kb) in *E. coli*. A preferred BAC vector consists of pBeloBAC11 vector that has been described by Kim et al. (1996). BAC libraries are prepared with this vector using size-selected genomic DNA that has been partially digested using enzymes that permit ligation into either the Bam HI or HindIII sites in the vector. Flanking these cloning sites are T7 and SP6 RNA polymerase transcription initiation sites that can be used to generate end probes by either RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC 11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

5. Delivery of the Recombinant Vectors

In order to effect expression of the polynucleotides and polynucleotide constructs of the invention, these constructs must be delivered into a cell. This delivery may be accomplished in vitro, as in laboratory procedures for transforming cell lines, or in vivo or ex vivo, as in the treatment of certain diseases states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987;), DEAE-dextran (Gopal, 1985), electroporation (Tur-Kaspa et al., 1986; Potter et al., 1984), direct microinjection (Harland et al., 1985), DNA-loaded liposomes (Nicolau et al., 1982; Fraley et al., 1979), and receptor-mediate transfection (Wu and Wu, 1987; 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application N° WO 90/11092 (Vical Inc.) and also in PCT application No. WO 95/11307 (Institut Pasteur, INSERM, Universitéd'Ottawa) as well as in the articles of Tacson et al.(1996) and of Huygen et al.(1996).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al.(1987).

In a further embodiment, the polynucleotide of the invention may be entrapped in a liposome (Gliosh and Bacchawat, 1991; Wong et al., 1980; Nicolau et al., 1987)

In a specific embodiment, the invention provides a composition for the in vivo production of the APM1 protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0,1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired APM1 polypeptide or the desired fragment thereof is reintroduced into the animal body in order to deliver the recombinant protein within the body either locally or systemically.

Cell Hosts

Another object of the invention consists of a host cell that have been transformed or transfected with one of the polynucleotides described therein, and more precisely a polynucleotide either comprising a APM1 regulatory polynucleotide or the coding sequence of the APM1 polypeptide selected from the group consisting of SEQ ID No 1 or a fragment or a variant thereof and SEQ ID No 5. Are included host cells that are transformed (prokaryotic cells) or that are transfected (eukaryotic cells) with a recombinant vector such as one of those described above.

Generally, a recombinant host cell of the invention comprises any one of the polynucleotides or the recombinant vectors described therein.

A preferred recombinant host cell according to the invention comprises a polynucleotide selected from the following group of polynucleotides:
a) a purified or isolated nucleic acid encoding a APM1 polypeptide, or a polypeptide fragment or variant thereof;
b) a purified or isolated nucleic comprising at least 8, preferably at least 15, more preferably at least 25, consecutive nucleotides of a nucleotide sequence selected from the group consisting of:
  1) the nucleotide sequence beginning at the nucleotide in position 1 and ending at the nucleotide in position 4811 of the nucleotide sequence of SEQ ID No 1 or a variant thereof or a sequence complementary thereto; more particularly, the nucleotide sequence beginning at the nucleotide in position 1 and ending at the nucleotide in position 3529 of the nucleotide sequence of SEQ ID No 1 or a variant thereof or a sequence complementary thereto;
  2) the nucleotide sequence beginning at the nucleotide in position 4852 and ending at the nucleotide in position 15142 of the nucleotide sequence of SEQ ID No 1 or a variant thereof or a sequence complementary thereto;
  3) the nucleotide sequence beginning at the nucleotide in position 15366 and ending at the nucleotide in position 16276 of the nucleotide sequence of SEQ ID No 1 or a variant thereof or a sequence complementary thereto; and
  4) the nucleotide sequence beginning at the nucleotide in position 20560 and ending at the nucleotide in position 20966 of the nucleotide sequence of SEQ ID No 1 or a variant thereof or a sequence complementary thereto;
c) a purified or isolated nucleic acid comprising at least 8 consecutive nucleotides, preferably at least 15 of the nucleotide sequence beginning at the nucleotide in position 1 and ending at the nucleotide in position 22 of the nucleotide sequence of SEQ ID No 5 or a variant thereof or a sequence complementary thereto;
d) a purified or isolated nucleic acid comprising an exon of the APM1 gene, a sequence complementary thereto or a variant thereof;
e) a purified or isolated nucleic acid comprising a combination of at least two exons of the APM1 gene, or the sequences complementary thereto wherein the polynucleotides are arranged within the nucleic acid, from the 5' end to the 3' end of said nucleic acid, in the same order than in SEQ ID No 1;
f) a purified or isolated nucleic acid comprising the nucleotide sequence SEQ ID No 2 or the sequences complementary thereto or a biologically active fragment or a variant thereof;
g) a purified or isolated nucleic acid comprising the nucleotide sequence SEQ ID No 3, or the sequence complementary thereto or a biologically active fragment or a variant thereof;

h) a polynucleotide consisting of:
  (1) a nucleic acid comprising a regulatory polynucleotide of SEQ ID No 2 or the sequences complementary thereto or a biologically active fragment or variant thereof;
  (2) a polynucleotide encoding a desired polypeptide or nucleic acid; or
  (3) optionally, a nucleic acid comprising a regulatory polynucleotide of SEQ ID No 3, or the sequence complementary thereto or a biologically active fragment or variant thereof; and i) a DNA construct as described previously in the present specification.

Another preferred recombinant cell host according to the present invention is characterized in that its genome or genetic background (including chromosome, plasmids) is modified by the nucleic acid coding for the APM1 polypeptide of SEQ ID No 5 or fragments or variants thereof.

A further recombinant cell host according to the invention comprises a polynucleotide containing a biallelic marker selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof; optionally, wherein said APM1-related biallelic marker is selected from the group consisting of A1, A2, and A7 or the group consisting of A4 and A8.

Preferred host cells used as recipients for the expression vectors of the invention are the following:
  a) Prokaryotic host cells: *Escherichia coli* strains (I.E.DH5-αstrain), *Bacillus subtilis, Salmonella typhinzuriunt*, and strains from species like Pseudomonas, Streptomyces and Staphylococcus;
  b) Eukaryotic host cells: HeLa cells (ATCC N°CCL2; N°CCL2.1; N°CCL2.2), Cv 1 cells (ATCC N°CCL70), COS cells (ATCC N°CRL1650; N°CRL1651), Sf-9 cells (ATCC N°CRL1711), C127 cells (ATCC N°CRL-1804), 3T3 (ATCC N°CRL-6361), CHO (ATCC N°CCL-61), human kidney 293. (ATCC N°45504; N°CRL-1573) and BHK (ECACC N°84100501; N°84111301); and
  c) other mammalian host cells.

The APM1 gene expression in mammalian, and typically human, cells may be rendered defective, or alternatively it may be proceeded with the insertion of a APM1 genomic or cDNA sequence with the replacement of the APM1 gene counterpart in the genome of an animal cell by a APM1 polynucleotide according to the invention. These genetic alterations may be generated by homologous recombination events using specific DNA constructs that have been previously described.

Host cells that may be used include mammalian zygotes, such as murine zygotes. For example, murine zygotes may undergo microinjection with a purified DNA molecule of interest, for example a purified DNA molecule that has previously been adjusted to a concentration range from 1 ng/mL—for BAC inserts-3 ng/µL—for P1 bacteriophage inserts-in 10 mM Tris-HCl, pH 7.4, 250 µM EDTA containing 100 mM NaCl, 30 µM spermine, and 70 µM spermidine. When the DNA to be microinjected has a large size, polyamines and high salt concentrations can be used in order to avoid mechanical breakage of this DNA, as described by Schedl et al (1993b).

Any of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines include the following: ES-E14TG2a (ATCC n° CRL-1821), ES-D3 (ATCC n° CRL1934 and n° CRL-11632), YS001 (ATCC n° CRL-11776), 36.5 (ATCC n° CRL-11116). To maintain ES cells in an uncommitted state, they are cultured in the presence of growth inhibited feeder cells that provide the appropriate signals to preserve this embryonic phenotype and serve as a matrix for ES cell adherence. Preferred feeder cells consist of primary embryonic fibroblasts that are established from tissue of day 13-day 14 embryos of virtually any mouse strain, that are maintained in culture, such as described by Abbondanzo et al.(1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skill artisan.

Transgenic Animals

The terms "transgenic animals" or "host animals" are used herein designate animals that have their genome genetically and artificially manipulated so as to include one of the nucleic acids according to the invention. Preferred animals are non-human mammals and include those belonging to a genus selected from Mus (e.g. mice), Rattus (e.g. rats) and Oryctogalus (e.g. rabbits) which have their genome artificially and genetically altered by the insertion of a nucleic acid according to the invention. In one embodiment, the invention encompasses non-human host mammals and animals comprising a recombinant vector of the invention or an APM1 gene disrupted by homologous recombination with a knock out vector.

The transgenic animals of the invention all include within a plurality of their cells a cloned recombinant or synthetic DNA sequence, more specifically one of the purified or isolated nucleic acids comprising a APM1 coding sequence, a APM1 regulatory polynucleotide or a DNA sequence encoding an antisense polynucleotide such as described in the present specification.

Preferred transgenic animals according to the invention contain in their somatic cells and/or in their germ line cells a polynucleotide selected from the following group of polynucleotides:
  a) a purified or isolated nucleic acid encoding a APM1 polypeptide, or a polypeptide fragment or variant thereof;
  b) a purified or isolated nucleic comprising at least 8, preferably at least 15, more preferably at least 25, consecutive nucleotides of a nucleotide sequence selected from the group consisting of:
    1) the nucleotide sequence beginning at the nucleotide in position 1 and ending at the nucleotide in position 4811 of the nucleotide sequence of SEQ ID No 1 or a variant thereof or a sequence complementary thereto; more particularly, the nucleotide sequence beginning at the nucleotide in position 1 and ending at the nucleotide in position 3529 of the nucleotide sequence of SEQ ID No 1 or a variant thereof or a sequence complementary thereto;

2) the nucleotide sequence beginning at the nucleotide in position 4852 and ending at the nucleotide in position 15142 of the nucleotide sequence of SEQ ID No 1 or a variant thereof or a sequence complementary thereto;

3) the nucleotide sequence beginning at the nucleotide in position 15366 and ending at the nucleotide in position 16276 of the nucleotide sequence of SEQ ID No 1 or a variant thereof or a sequence complementary thereto; and 4) the nucleotide sequence beginning at the nucleotide in position 20560 and ending at the nucleotide in position 20966 of the nucleotide sequence of SEQ ID No 1 or a variant thereof or a sequence complementary thereto;

c) a purified or isolated nucleic acid comprising at least 8 consecutive nucleotides, preferably at least 15 of the nucleotide sequence beginning at the nucleotide in position 1 and ending at the nucleotide in position 22 of the nucleotide sequence of SEQ ID No 5 or a variant thereof or a sequence complementary thereto;

d) a purified or isolated nucleic acid comprising an exon of the APM1 gene, a sequence complementary thereto or a variant thereof;

e) a purified or isolated nucleic acid comprising a combination of at least two exons of the APM1 gene, or the sequences complementary thereto wherein the polynucleotides are arranged within the nucleic acid, from the 5' end to the 3' end of said nucleic acid, in the same order than in SEQ ID No 1;

f) a purified or isolated nucleic acid comprising the nucleotide sequence SEQ ID No 2 or the sequences complementary thereto or a biologically active fragment or a variant thereof;

g) a purified or isolated nucleic acid comprising the nucleotide sequence SEQ ID No 3, or the sequence complementary thereto or a biologically active fragment or a variant thereof;

h) a polynucleotide consisting of:
  (1) a nucleic acid comprising a regulatory polynucleotide of SEQ ID No 2 or the sequences complementary thereto or a biologically active fragment or variant thereof,
  (2) a polynucleotide encoding a desired polypeptide or nucleic acid; or
  (3) optionally, a nucleic acid comprising a regulatory polynucleotide of SEQ ID No 3, or the sequence complementary thereto or a biologically active fragment or variant thereof; and i) a DNA construct as described previously in the present specification.

The transgenic animals of the invention thus contain specific sequences of exogenous genetic material such as the nucleotide sequences described above in detail.

A further transgenic animals according to the invention contains in their somatic cells and/or in their germ line cells a polynucleotide comprising a biallelic marker selected from the group consisting of A1, A2, A3, A4, A5, A6, A7, A8, A9, A10, A11, A12, A13, A14, A15, A16, A17, A18, A19, A20, A21, A22, A23, A24, A25 and A26, and the complements thereof; optionally, wherein said APM 1-related biallelic marker is selected from the group consisting of A1, A2, and A7 or the group consisting of A4 and A8.

In a first preferred embodiment, these transgenic animals may be good experimental models in order to study the diverse pathologies related to cell differentiation, in particular concerning the transgenic animals within the genome of which has been inserted one or several copies of a polynucleotide encoding a native APM1 protein, or alternatively a mutant APM1 protein.

In a second preferred embodiment, these transgenic animals may express a desired polypeptide of interest under the control of the regulatory polynucleotides of the APM1 gene, leading to good yields in the synthesis of this protein of interest, and eventually a tissue specific expression of this protein of interest.

The design of the transgenic animals of the invention may be made according to the conventional techniques well known from the one skilled in the art. For more details regarding the production of transgenic animals, and specifically transgenic mice, it may be referred to U.S. Pat. No. 4,873,191, issued Oct. 10, 1989, U.S. Pat. No. 5,464,764 issued Nov. 7, 1995 and U.S. Pat. No. 5,789,215, issued Aug. 4, 1998, these documents being herein incorporated by reference to disclose methods producing transgenic mice.

Transgenic animals of the present invention are produced by the application of procedures which result in an animal with a genome that has incorporated exogenous genetic material. The procedure involves obtaining the genetic material, or a portion thereof, which encodes either a APM1 coding sequence, a APM1 regulatory polynucleotide or a DNA sequence encoding a APM1 antisense polynucleotide such as described in the present specification.

A recombinant polynucleotide of the invention is inserted into an embryonic or ES stem cell line. The insertion is preferably made using electroporation, such as described by Thomas et al.(1987). The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that may be used according to the invention is described by Mansour et al.(1988).

Then, the positive cells are isolated, cloned and injected into 3.5 days old blastocysts from mice, such as described by Bradley (1987). The blastocysts are then inserted into a female host animal and allowed to grow to term.

Alternatively, the positive ES cells are brought into contact with embryos at the 2.5 days old 8–16 cell stage (morulae) such as described by Wood et al.(1993) or by Nagy et al.(1993), the ES cells being internalized to colonize extensively the blastocyst including the cells which will give rise to the germ line.

The offspring of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Recombinant Cell Lines Derived from the Transgenic Animals of the Invention

A further object of the invention consists of recombinant host cells obtained from a transgenic animal described herein. In one embodiment the invention encompasses cells derived from non-human host mammals and animals comprising a recombinant vector of the invention or an APM1 gene disrupted by homologous recombination with a knock out vector.

Recombinant cell lines may be established in vitro from cells obtained from any tissue of a transgenic animal according to the invention, for example by transfection of primary cell cultures with vectors expressing onc-genes such as SV40 large T antigen, as described by Chou (1989) and Shay et al.(1991).

Method for Producing an APM1 Polypeptide

It is now easy to produce proteins in high amounts by genetic engineering techniques through expression vectors such as plasmids, phages or phagemids. The polynucleotide that codes for the APM1 protein is inserted in an appropriate expression vector in order to produce the polypeptide of interest in vitro.

Thus, the present invention also concerns a method for a APM1 protein, and especially a polypeptide of SEQ ID No 6, wherein said method comprises:

a) culturing, in an appropriate culture medium, a cell host previously transformed or transfected with the recombinant vector comprising a nucleic acid encoding the APM1 protein;

b) harvesting the culture medium thus conditioned or lyse the cell host, for example by sonication or by an osmotic shock;

c) separating or purifying, from the said culture medium, or from the pellet of the resultant host cell lysate the thus produced polypeptide of interest; and d) optionally characterizing the produced polypeptide of interest.

In a specific embodiment of the above method, the nucleic acid coding for the APM1 protein is inserted in an appropriate vector, optionally after an appropriate cleavage of this amplified nucleic acid with one or several restriction endonucleases. In a preferred embodiment, the nucleic acid encoding for the APM1 protein is selected from a group consisting of SEQ ID No 1 or a fragment thereof and SEQ ID No 5. In a further embodiment, the nucleic acid encoding for the APM1 protein comprises an allele of at least one of the biallelic markers A1 to A26. The nucleic acid coding for the APM1 protein may be the resulting product of an amplification reaction using a pair of primers according to the invention (by SDA, TAS, 3SR NASBA, TMA etc.).

The polypeptides according to the invention may be characterized by binding onto an immunoaffinity chromatography column on which polyclonal or monoclonal antibodies directed to a polypeptide of SEQ ID No 6 have previously been immobilized.

The polypeptides or peptides thus obtained may be purified, for example by high performance liquid chromatography, such as reverse phase and/or cationic exchange HPLC, as described by Rougeot et al.(1994). The reason to prefer this kind of peptide or protein purification is the lack of byproducts found in the elution samples which renders the resultant purified protein or peptide more suitable for a therapeutic use.

Method for Screening Substances Interacting with the Regulatory Sequences of the APM1 Gene The present invention also concerns a method for screening substances or molecules that are able to interact with the regulatory sequences of the APM1 gene, such as for example promoter or enhancer sequences.

Nucleic acids encoding proteins which are able to interact with the regulatory sequences of the APM1 gene, more particularly a nucleotide sequence selected from the group consisting of the polynucleotides of SEQ ID Nos 2 and 3 or a fragment or variant thereof, and preferably a variant comprising one of the biallelic markers of the invention, may be identified by using a one-hybrid system, such as that described in the booklet enclosed in the Matchmaker One-Hybrid System kit from Clontech (Catalog Ref. n° K1603-1), the technical teachings of which are herein incorporated by reference. Briefly, the target nucleotide sequence is cloned upstream of a selectable reporter sequence and the resulting DNA construct is integrated in the yeast genome (*Saccharomyces cerevisiae*). The yeast cells containing the reporter sequence in their genome are then transformed with a library consisting of fusion molecules between cDNAs encoding candidate proteins for binding onto the regulatory sequences of the APM1 gene and sequences encoding the activator domain of a yeast transcription factor such as GAL4. The recombinant yeast cells are plated in a culture broth for selecting cells expressing the reporter sequence. The recombinant yeast cells thus selected contain a fusion protein that is able to bind onto the target regulatory sequence of the APM1 gene. Then, the cDNAs encoding the fusion proteins are sequenced and may be cloned into expression or transcription vectors in vitro. The binding of the encoded polypeptides to the target regulatory sequences of the APM1 gene may be confirmed by techniques familiar to the one skilled in the art, such as gel retardation assays or DNAse protection assays.

Gel retardation assays may also be performed independently in order to screen candidate molecules that are able to interact with the regulatory sequences of the APM1 gene, such as described by Fried and Crothers (1981), Garner and Revzin (1981) and Dent and Latchman (1993), the teachings of these publications being herein incorporated by reference. These techniques are based on the principle according to which a DNA fragment which is bound to a protein migrates slower than the same unbound DNA fragment. Briefly, the target nucleotide sequence is labeled. Then the labeled target nucleotide sequence is brought into contact with either a total nuclear extract from cells containing transcription factors, or with different candidate molecules to be tested. The interaction between the target regulatory sequence of the APM1 gene and the candidate molecule or the transcription factor is detected after gel or capillary electrophoresis through a retardation in the migration.

Method for Screening Ligands that Modulate the Expression of the APM1 Gene

Another subject of the present invention is a method for screening molecules that modulate the expression of the APM1 protein. Such a screening method comprises:

a) cultivating a prokaryotic or an eukaryotic cell that has been transfected with a nucleotide sequence encoding the APM1 protein or a variant or a fragment thereof, placed under the control of its own promoter;

b) bringing into contact the cultivated cell with a molecule to be tested; and c) quantifying the expression of the APM1 protein or a variant or a fragment thereof.

In an embodiment, the nucleotide sequence encoding the APM1 protein or a variant or a fragment thereof comprises an allele of at least one of the biallelic markers A1, A2, A3, A4, A5, A6, A7, A8, A9, A10, A11, A12, A13, A14, A15, A16, A17, A18, A19, A20, A21, A22, A23, A24, A25 and A26, and the complements thereof; optionally, wherein said APM1-related biallelic marker is selected from the group consisting of A1, A2, and A7 or the group consisting of A4 and A8.

Using DNA recombination techniques well known by the one skill in the art, the APM1 protein encoding DNA sequence is inserted into an expression vector, downstream from its promoter sequence. As an illustrative example, the promoter sequence of the APM1 gene is contained in the nucleic acid of SEQ ID No 2.

The quantification of the expression of the APM1 protein may be realized either at the mRNA level or at the protein level. In the latter case, polyclonal or monoclonal antibodies may be used to quantify the amounts of the APM1 protein that have been produced, for example in an ELISA or a RIA assay.

In a preferred embodiment, the quantification of the APM1 mRNA is realized by a quantitative PCR amplification of the cDNA obtained by a reverse transcription of the total mRNA of the cultivated APM1-transfected host cell, using a pair of primers specific for APM1.

The present invention also concerns a method for screening substances or molecules that are able to increase, or in contrast to decrease, the level of expression of the APM1 gene. Such a method may allow the one skilled in the art to select substances exerting a regulating effect on the expression level of the APM1 gene and which may be useful as active ingredients included in pharmaceutical compositions for treating patients suffering from deficiencies in the regulation of expression of the APM1 gene, particularly patients suffering from obesity.

The invention also features a method for screening a candidate substance or molecule for modulation of the expression of the APM1 gene, comprising:

a) providing a recombinant cell host containing a nucleic acid, wherein said nucleic acid comprises a nucleotide sequence of SEQ ID No 2 or a biologically active fragment or variant thereof located upstream a polynucleotide encoding a detectable protein;

b) obtaining a candidate substance; and c) determining the ability of the candidate substance to modulate the expression levels of the polynucleotide encoding the detectable protein.

In a specific embodiment, the nucleic acid comprising a nucleotide sequence of SEQ ID No 2 or a biologically active fragment or variant thereof includes a biallelic marker selected from the group consisting of A1, A2, A3, A4, A5, A6, A7, A8, A9, A10, A11, A12, A13, A14, A15, A16, A17, A18, A19, A20, A21, A22, A23, A24, A25 and A26 or the complements thereof; optionally, wherein said APM1-related biallelic marker is selected from the group consisting of A1, A2, and A7 or the group consisting of A4 and A8.

In a further embodiment, the nucleic acid comprising the nucleotide sequence of SEQ ID No 2 or a biologically active fragment or variant thereof also includes a 5'UTR region of the APM1 cDNA of SEQ ID No 5, or one of its biologically active fragments or variants thereof.

Among the preferred polynucleotides encoding a detectable protein, there may be cited polynucleotides encoding beta galactosidase, green fluorescent protein (GFP) and chloramphenicol acetyl transferase (CAT).

The invention also pertains to kits useful for performing the hereinbefore described screening method. Preferably, such kits comprise a recombinant vector that allows the expression of a nucleotide sequence of SEQ ID No 2 or a biologically active fragment or variant thereof located upstream and operably linked to a polynucleotide encoding a detectable protein or the APM1 protein or a fragment or a variant thereof.

In another embodiment, a method for the screening of a candidate substance or molecule for modulation of the expression of the APM1 gene comprises:

a) providing a recombinant host cell containing a nucleic acid, wherein said nucleic acid comprises a 5'UTR sequence of the APM1 cDNA of SEQ ID No 5, or one of its biologically active fragments or variants, the 5'UTR sequence or its biologically active fragment or variant being operably linked to a polynucleotide encoding a detectable protein;

b) obtaining a candidate substance; and c) determining the ability of the candidate substance to modulate the expression levels of the polynucleotide encoding the detectable protein.

In a specific embodiment of the above screening method, the nucleic acid that comprises a nucleotide sequence selected from the group consisting of the 5'UTR sequence of the APM1 cDNA of SEQ ID No 5 or one of its biologically active fragments or variants, includes a promoter sequence which is endogenous with respect to the APM1 5'UTR sequence.

In another specific embodiment of the above screening method, the nucleic acid that comprises a nucleotide sequence selected from the group consisting of the 5'UTR sequence of the PMI cDNA of SEQ ID No 5 or one of its biologically active fragments or variants, includes a promoter sequence which is exogenous with respect to the APM1 5'UTR sequence defined therein.

In a further preferred embodiment, the nucleic acid comprising the 5'-UTR sequence of the APM1 cDNA or SEQ ID NO 5 or the biologically active fragments thereof includes a biallelic marker selected from the group consisting of A1, A2, A3, A4, A5, A6, A7, A8, A9, A10, A11, A12, A13, A14, A15, A16, A17, A18, A19, A20, A21, A22, A23, A24, A25 and A26or the complements thereof; optionally, wherein said APM1-related biallelic marker is selected from the group consisting of A1, A2, and A7 or the group consisting of A4 and A8.

The invention further deals with a kit for the screening of a candidate substance modulating the expression of the APM1 gene, wherein said kit comprises a recombinant vector that comprises a nucleic acid including a 5'UTR sequence of the APM1 cDNA of SEQ ID No 5, or one of their biologically active fragments or variants, the 5'UTR sequence or its biologically active fragment or variant being operably linked to a polynucleotide encoding a detectable protein.

For the design of suitable recombinant vectors useful for performing the screening methods described above, it will be referred to the section of the present specification wherein the preferred recombinant vectors of the invention are detailed.

Expression levels and patterns of APM1 may be analyzed by solution hybridization with long probes as described in International Patent Application No. WO 97/05277, which is hereby incorporated herein by reference in its entirety including any figures, tables, or references. Briefly, the APM1 cDNA or the APM1 genomic DNA described above, or fragments thereof, is inserted at a cloning site immediately downstream of a bacteriophage (T3, T7 or SP6) RNA polymerase promoter to produce antisense RNA. Preferably, the APM1 insert comprises at least 100 or more consecutive nucleotides of the genomic DNA sequence or the cDNA sequences. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40–50° C. for 16 hours in an 80% formamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of APM1 gene expression may also be performed using arrays. As used herein, the term "array" means a one dimensional, two dimensional, or multidimensional arrangement of a plurality of nucleic acids of sufficient length to permit specific detection of expression of mRNAs capable of hybridizing thereto. For example, the arrays may contain a plurality of nucleic acids derived from genes whose expression levels are to be assessed. The arrays may include the APM1 genomic DNA, the APM1 cDNA sequences or the sequences complementary thereto or fragments thereof, particularly those comprising at least one of the biallelic markers according the present invention, preferably at least one of the biallelic markers A1 to A26. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiment, the fragments are more than 100 nucleotides in length. In some embodiments the fragments may be more than 500 nucleotides in length.

For example, quantitative analysis of APM1 gene expression may be performed with a complementary DNA microarray as described by Schena et al. (1995 and 1996). Full length APM1 cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0.2% SDS for 1 min, twice in water for 1 min and once for 5 min in sodium borohydride solution. The arrays are submerged in water for 2 min at 95° C., transferred into 0.2% SDS for 1 min, rinsed twice with water, air dried and stored in the dark at 25° C.

Cell or tissue mRNA is isolated or commercially obtained and probes are prepared by a single round of reverse transcription. Probes are hybridized to 1 cm$^2$ microarrays under a 14×14 mm glass coverslip for 6–12 hours at 60° C. Arrays are washed for 5 min at 25° C. in low stringency wash buffer (1×SSC/0.2% SDS), then for 10 min at room temperature in high stringency wash buffer (0.1×SSC/0.2% SDS). Arrays are scanned in 0.1×SSC using a fluorescence laser scanning device fitted with a custom filter set. Accurate differential expression measurements are obtained by taking the average of the ratios of two independent hybridizations.

Quantitative analysis of APM1 gene expression may also be performed with full length APM1 cDNAs or fragments thereof in complementary DNA arrays as described by Pietu et al.(1996). The full length APM1 cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the APM1 genomic DNA, the APM1 cDNA, or fragments thereof can be done through high density nucleotide arrays as described by Lockhart et al.(1996) and Sosnowsky et al.(1997). Oligonucleotides of 15–50 nucleotides from the sequences of the APM1 genomic DNA, the APM1 cDNA sequences particularly those comprising at least one of biallelic markers according the present invention, preferably at least one biallelic marker selected from the group consisting of A1 to A26, or the sequences complementary thereto, are synthesized directly on the chip (Lockhart et al., supra) or synthesized and then addressed to the chip (Sosnowski et al., supra). Preferably, the oligonucleotides are about 20 nucleotides in length.

APM1 cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields (Sosnowsky et al., 1997)., the dyes or labeling compounds are detected and quantified. Duplicate hybridizations are performed. Comparative analysis of the intensity of the signal originating from cDNA probes on the same target oligonucleotide in different cDNA samples indicates a differential expression of APM1 mRNA.

Methods for Inhibiting the Expression of an APM1 Gene

Other therapeutic compositions according to the present invention comprise advantageously an oligonucleotide fragment of the nucleic sequence of APM1 as an antisense tool or a triple helix tool that inhibits the expression of the corresponding APM1 gene. A preferred fragment of the nucleic sequence of APM1 comprises an allele of at least one of the biallelic markers A1 to A26.

Antisense Approach

Preferred methods using antisense polynucleotide according to the present invention are the procedures described by Sczakiel et al.(1995).

Preferably, the antisense tools are chosen among the polynucleotides (15–200 bp long) that are complementary to the 5' end of the APM1 mRNA. In another embodiment, a combination of different antisense polynucleotides complementary to different parts of the desired targeted gene are used.

Preferred antisense polynucleotides according to the present invention are complementary to a sequence of the mRNAs of APM1 that contains either the translation initiation codon ATG or a splicing donor or acceptor site.

The antisense nucleic acids should have a length and melting temperature sufficient to permit formation of an intracellular duplex having sufficient stability to inhibit the expression of the APM1 mRNA in the duplex. Strategies for designing antisense nucleic acids suitable for use in gene therapy are disclosed in Green et al., (1986) and Izant and Weintraub, (1984), the disclosures of which are incorporated herein by reference.

In some strategies, antisense molecules are obtained by reversing the orientation of the APM1 coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of APM1 antisense nucleic acids in vivo by operably linking DNA containing the antisense sequence to a promoter in a suitable expression vector.

Alternatively, suitable antisense strategies are those described by Rossi et al.(1991), in the International Applications Nos. WO 94/23026, WO 95/04141, WO 92/18522 and in the European Patent Application No. EP 0 572 287 A2.

An alternative to the antisense technology that is used according to the present invention consists in using ribozymes that will bind to a target sequence via their complementary polynucleotide tail and that will cleave the corresponding RNA by hydrolyzing its target site (namely "hammerhead ribozymes"). Briefly, the simplified cycle of a hammerhead ribozyme consists of (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al.(1995), the specific preparation procedures being referred to in said article being herein incorporated by reference.

Triple Helix Approach

The APM1 genomic DNA may also be used to inhibit the expression of the APM1 gene based on intracellular triple helix formation.

Triple helix oligonucleotides are used to inhibit transcription from a genome. They are particularly useful for studying alterations in cell activity when it is associated with a particular gene.

Similarly, a portion of the APM1 genomic DNA can be used to study the effect of inhibiting APM1 transcription within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from the APM1 genomic DNA are contemplated within the scope of this invention.

To carry out gene therapy strategies using the triple helix approach, the sequences of the APM1 genomic DNA are first scanned to identify 10-mer to 20-mer homopyrimidine or homopurine stretches which could be used in triple-helix based strategies for inhibiting APM1 expression. Following identification of candidate homopyrimidine or homopurine stretches, their efficiency in inhibiting APM1 expression is assessed by introducing varying amounts of oligonucleotides containing the candidate sequences into tissue culture cells which express the APM1 gene.

The oligonucleotides can be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced APM1 expression using techniques such as Northern blotting, RNase protection assays, or PCR based strategies to monitor the transcription levels of the APM1 gene in cells which have been treated with the oligonucleotide.

The oligonucleotides which are effective in inhibiting gene expression in tissue culture cells may then be introduced in vivo using the techniques described above in the antisense approach at a dosage calculated based on the in vitro results, as described in antisense approach.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation see Griffin et al.(1989), which is hereby incorporated by this reference.

Throughout the application it is specifically contemplated that in each case of a list of biallelic markers, or probes, or primers, that list is also envisioned to include all but any one of its members, or all but any two, or all but any three, until there is only one remaining member. The examples that follow are exemplary only, and not to be taken as meant to limit the invention in any way.

EXAMPLES

Example 1

Identification of Biallelic Markers-DNA Extraction

Donors were unrelated and healthy. They presented a sufficient diversity for being representative of a French heterogeneous population. The DNA from 100 individuals was extracted and tested for the detection of the biallelic markers.

30 mL of peripheral venous blood were taken from each donor in the presence of EDTA. Cells (pellet) were collected after centrifugation for 10 minutes at 2000 rpm. Red cells were lysed by a lysis solution (50 mL final volume: 10 mM Tris pH7.6; 5 mM $MgCl_2$; 10 mM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:
- 3 mL TE 10-2 (Tris-HCl 10 mM, EDTA 2 mM) /NaCl 0 4 M
- 200 µL SDS 10%
- 500 µL K-proteinase (2 mg K-proteinase in TE 10-2/NaCl 0.4 M).

For the extraction of proteins, 1 mL saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and was centrifuged for 20 minutes at 2000 rpm. The pellet was dried at 37° C., and was resuspended in 1 mL TE 10-1 or 1 mL water. The DNA concentration was evaluated by measuring the OD at 260 nm (1 unit OD=50 µg/mL DNA).

To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 2

Identification of Biallelic Markers: Amplification of Genomic DNA by PCR

The amplification of specific genomic sequences of the DNA samples of example 1 was carried out on the pool of DNA obtained previously. In addition, 50 individual samples were similarly amplified.

PCR assays were performed using the following protocol:

| | |
|---|---|
| Final volume | 25 μL |
| DNA | 2 ng/μL |
| MgCl$_2$ | 2 mM |
| dNTP (each) | 200 μM |
| primer (each) | 2.9 ng/μL |
| Ampli Taq Gold DNA polymerase | 0.05 unit/μL |
| PCR buffer (10x = 0.1 M TrisHCl pH8.3 0.5 M KCl) | 1x |

Each pair of first primers was designed using the sequence information of the APM1 gene disclosed herein and the OSP software (Hillier & Green, 1991). This first pair of primers was about 20 nucleotides in length and had the sequence corresponding to the SEQ ID positions disclosed in Table 1 in the columns labeled PU and RP.

TABLE 1

| Amplicon | Position of the amplicon in SEQ ID 1 | PU | Position of PU primer in SEQ ID 1 | RP | Position of RP primer in SEQ ID 1 |
|---|---|---|---|---|---|
| 9-27 | 3528–3946 | B1 | 3528–3545 | C1 | 3928–3946 |
| 9-28 | 3892–4321 | B2 | 3892–3911 | C2 | 4303–4321 |
| 99-14402 | 4155–4602 | B3 | 4155–4175 | C3 | 4584–4602 |
| 9-29 | 4223–4642 | B4 | 4223–4242 | C4 | 4623–4642 |
| 9-30 | 4599–5027 | B5 | 4599–4618 | C5 | 5008–5027 |
| 99-14387 | 10990–11442 | B6 | 10990–11008 | C6 | 11423–11442 |
| 99-14389 | 12472–12966 | B7 | 12472–12491 | C7 | 12946–12966 |
| 9-12 | 15073–15520 | B8 | 15073–15092 | C8 | 15503–15520 |
| 9-13 | 15131–15551 | B9 | 15131–15150 | C9 | 15532–15551 |
| 99-14405 | 15759–16211 | B10 | 15759–15776 | C10 | 16191–16211 |
| 9-14 | 16233–16652 | B11 | 16233–16251 | C11 | 16633–16652 |
| 9-15 | 16604–17025 | B12 | 16604–16621 | C12 | 17006–17025 |
| 9-16 | 16982–17402 | B13 | 16982–17001 | C13 | 17384–17402 |
| 9-17 | 17216–17517 | B14 | 17216–17233 | C14 | 17498–17517 |
| 9-18 | 17300–17503 | B15 | 17300–17317 | C15 | 17486–17503 |
| 17-30 | 730–1137 | B16 | 730–752 | C16 | 1117–1137 |
| 17-31 | 4798–5385 | B17 | 4798–4819 | C17 | 5364–5385 |
| 17-32 | 10614–11114 | B18 | 10614–10635 | C18 | 11093–11114 |
| 17-33 | 13843–14517 | B19 | 13843–13865 | C19 | 14496–14517 |
| 17-34 | 13843–14859 | | | C20 | 14839–14859 |
| 17-35 | 14745–15219 | B20 | 14745–14766 | C21 | 15199–15219 |
| 17-36 | 15381–15987 | B21 | 15381–15402 | C22 | 15966–15987 |
| 17-37 | 17201–18261 | B22 | 17201–17222 | C23 | 18240–18261 |
| 17-38 | 18141–19336 | B23 | 18141–18163 | C24 | 19314–19336 |

Preferably, the primers contained a common oligonucleotide tail upstream of the specific bases targeted for amplification which was useful for sequencing.

Primers PU contain the following additional PU 5' sequence: TGTAAAACGACGGCCAGT; primers RP contain the following RP 5' sequence: CAGGAAACAGCTATGACC. The primer containing the additional PU 5' sequence is listed in SEQ ID No 7. The primer containing the additional RP 5' sequence is listed in SEQ ID No 8.

The synthesis of these primers was performed following the phosphoramidite method, on a GENSET UFPS 24.1 synthesizer.

DNA amplification was performed on a Genius II thermocycler. After heating at 95° C. for 10 min, 40 cycles were performed. Each cycle comprised: 30 sec at 95° C., 54° C. for 1 min, and 30 sec at 72° C. For final elongation, 10 min at 72° C. ended the anplification. The quantities of the amplification products obtained were determined on 96-well microtiter plates, using a fluorometer and Picogreen as intercalant agent (Molecular Probes).

Example 3

Identification of Biallelic Markers-Sequencing of Amplified Genomic DNA and Identification of Polymorphisms The sequencing of the amplified DNA obtained in example 2 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software (2.1.2 version) and the above mentioned proprietary "Trace" basecaller).

The sequence data were further evaluated using the above mentioned polymorphism analysis software designed to detect the presence of biallelic markers among the pooled amplified fragments. The polymorphism search was based on the presence of superimposed peaks in the electrophoresis pattern resulting from different bases occurring at the same position as described previously.

15 fragments of amplification were analyzed. In 5 of these segments, 8 biallelic markers were detected. The localization of these biallelic markers are as shown in Table 2.

TABLE 2

| Amplicon | Biallelic marker | Marker Name | Localization in APM1 gene | Polymorphism | Marker position in SEQ ID No 1 |
|---|---|---|---|---|---|
| 9-27 | A1 | 9-27/261 | 5' regulatory region | Allele 1: G<br>Allele 2: C | 3787 |
| 99-14387 | A2 | 99-14387/129 | Intron 1 | Allele 1: A<br>Allele 2: C | 11118 |
| 9-12 | A3 | 9-12/48 | Intron 1 | Allele 1: T<br>Allele 2: C | 15120 |
| 9-12 and 9-13 | A4 | 9-12/124 or 9-13/66 | Exon 2 | Allele 1: T<br>Allele 2: G | 15196 |
| 9-12 and 9-13 | A5 | 9-12/355 or 9-13/297 | Intron 2 | Allele 1: G<br>Allele 2: T | 15427 |
| 9-12 and 9-13 | A6 | 9-12/428 or 9-13/370 | Intron 2 | Allele 1: A<br>Allele 2: G | 15500 |
| 99-14405 | A7 | 99-14405/105 | Intron 2 | Allele 1: G<br>Allele 2: A | 15863 |
| 9-16 | A8 | 9-16/189 | Exon 3 | Allele 1: A | 17170 |

TABLE 2-continued

| Amplicon | Biallelic marker | Marker Name | Localization in APM1 gene | Polymorphism | Marker position in SEQ ID No 1 |
|---|---|---|---|---|---|
| 17-30 | A9 | 17-30-216 | 5' regulatory region | Allele 2: Del Allele 1: A Allele 2: G | 945 |
| 9-27 | A10 | 9-27-211 | 5' regulatory region | Allele 1: A Allele 2: G | 3738 |
| 9-27 | A11 | 9-27-246 | 5' regulatory region | Allele 1: A Allele 2: G | 3773 |
| 17-31 | A12 | 17-31-298 | Intron 1 | Allele 1: A Allele 2: G | 5095 |
| 17-31 | A13 | 17-31-413 | Intron 1 | Allele 1: C Allele 2: T | 5210 |
| 17-32 | A14 | 17-32-24 | Intron 1 | Allele 1: T Allele 2: C | 10637 |
| 99-14387 | A15 | 99-14387-50 | Intron 1 | Allele 1: A Allele 2: C | 11039 |
| 99-14387 | A16 | 99-14387-199 | Intron 1 | Allele 1: A Allele 2: G | 11188 |
| 17-33 | A17 | 17-33-TGAGACT | Intron 1 | Allele 1: no insert Allele 2: TGAGACT insert | 13973 |
| 17-34 | A18 | 17-34-860 | Intron 1 | Allele 1: A Allele 2: G | 14702 |
| 17-34 | A19 | 17-34-915 | Intron 1 | Allele 1: A Allele 2: G | 14757 |
| 17-35 | A20 | 17-35-71 | Intron 1 | Allele 1: C Allele 2: T | 14815 |
| 17-35 | A21 | 17-35-306 | Intron 1 | Allele 1: G Allele 2: T | 15050 |
| 17-36 | A22 | 17-36-47 | Intron 2 | Allele 1: G Allele 2: C | 15680 |
| 17-36 | A23 | 17-36-120 | Intron 2 | Allele 1: C Allele 2: T | 15790 |
| 17-37 | A24 | 17-37-629 | Exon 3 | Allele 1: A Allele 2: G | 17829 |
| 17-37 | A25 | 17-37-811 | Exon 3 | Allele 1: A Allele 2: G | 18011 |
| 17-38 | A26 | 17-38-349 | Exon 3 | Allele 1: C Allele 2: T | 18489 |

Example 4

Validation of the Polymorphisms through Microsequencing

The biallelic markers identified in Example 3 were further confirmed and their respective frequencies were determined through microsequencing. Microsequencing was carried out for each individual DNA sample described in Example 1.

Amplification from genomic DNA of individuals was performed by PCR as described above for the detection of the biallelic markers with the same set of PCR primers (Table 1).

The preferred primers used in microsequencing were about 19 nucleotides in length and hybridized just upstream of the considered polymorphic base. According to the invention, the primers used in microsequencing are detailed in Table 3.

TABLE 3

| Marker Name | Marker | Mis. 1 | Position of mis 1 in SEQ ID NO 1 | Mis. 2 | Position of mis 2 In SEQ ID No 1 |
|---|---|---|---|---|---|
| 9-27/261 | A1 | D1 | 3768–3786 | E1 | 3788–3806 |
| 99-14387/129 | A2 | D2 | 11099–11117 | E2 | 11119–11137 |
| 9-12/48 | A3 | D3 | 15101–15119 | E3 | 15121–15139 |
| 9-12/124 or 9-13/66 | A4 | D4 | 15177–15195 | E4 | 15197–15215 |
| 9-12/355 or 9-13/297 | A5 | D5 | 15408–15426 | E5 | 15428–15446 |
| 9-12/428 or 9-13/370 | A6 | D6 | 15481–15499 | E6 | 15501–15519 |
| 99-14405/105 | A7 | D7 | 15844–15862 | E7 | 15864–15882 |
| 9-16/189 | A8 | D8 | 17151–17169 | E8 | 17171–17189 |
| 17-30-216 | A9 | D9 | 926–944 | E9 | 946–964 |
| 9-27-211 | A10 | D10 | 3719–3737 | E10 | 3739–3757 |
| 9-27-246 | A11 | D11 | 3754–3772 | E11 | 3774–3792 |

TABLE 3-continued

| Marker Name | Marker | Mis. 1 | Position of mis 1 in SEQ ID NO 1 | Mis. 2 | Position of mis 2 In SEQ ID No 1 |
|---|---|---|---|---|---|
| 17-31-298 | A12 | D12 | 5076–5094 | E12 | 5096–5114 |
| 17-31-413 | A13 | D13 | 5191–5209 | E13 | 5211–5229 |
| 17-32-24 | A14 | D14 | 10618–10636 | E14 | 10638–10656 |
| 99-14387-50 | A15 | D15 | 11020–11038 | E15 | 11040–11058 |
| 99-14387-199 | A16 | D16 | 11169–11187 | E16 | 11189–11207 |
| 17-33-TGAGACT | A17 | D17 | 13954–13972 | E17 | 13974–13992 |
| 17-34-860 | A18 | D18 | 14683–14701 | E18 | 14703–14721 |
| 17-34-915 | A19 | D19 | 14738–14756 | E19 | 14758–14776 |
| 17-35-71 | A20 | D20 | 14796–14814 | E20 | 14816–14834 |
| 17-35-306 | A21 | D21 | 15031–15049 | E21 | 15051–15069 |
| 17-36-47 | A22 | D22 | 15661–15679 | E22 | 15681–15699 |
| 17-36-120 | A23 | D23 | 15771–15789 | E23 | 15791–15809 |
| 17-37-629 | A24 | D24 | 17810–17828 | E24 | 17830–17848 |
| 17-37-811 | A25 | D25 | 17992–18010 | E25 | 18012–18030 |
| 17-38-349 | A26 | D26 | 18470–18488 | E26 | 18490–18508 |

Mis 1 and Mis 2 refer to microsequencing primers that hybridize with the non-coding strand of the APM1 gene and with the coding strand of the APM1 gene, respectively.

The microsequencing reaction was performed as follows

After purification of the amplification products, the microsequencing reaction mixture was prepared by adding, in a 20 μL final volume: 10 pmol microsequencing oligonucleotide, 1 U Thermosequenase (Amersham E79000G), 1.25 μL Thermosequenase buffer (260 mM Tris HCl pH 9.5, 65 mM MgCl$_2$), and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C., 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position, each sample is categorized classification as homozygous or heterozygous type based on the height ratio.

Oligonucleotide probes may be used in genotyping biallelic markers by hybridization assays. The nucleic acid sample is contacted with one or more allele specific oligonucleotide probes which, specifically hybridize to one or more alleles associated with a detectable phenotype. The probes are 25-mers with an APM1-related biallelic marker in the center position. Probes used in the hybridization assay may include the probes listed in Table 4.

TABLE 4

| BM | Marker Name | Position range of probes in SEQ ID No genomic | | Probes |
|---|---|---|---|---|
| A1 | 9-27/261 | 3775 | 3799 | P1 |
| A2 | 99-14387/129 | 11106 | 11130 | P2 |
| A3 | 9-12/48 | 15108 | 15132 | P3 |
| A4 | 9-12/124 | 15184 | 15208 | P4 |
| A5 | 9-12/355 | 15415 | 15439 | P5 |
| A6 | 9-12/428 | 15488 | 15512 | P6 |
| A7 | 99-14405/105 | 15851 | 15875 | P7 |
| A8 | 9-16/189 | 17158 | 17182 | P8 |
| A9 | 17-30-216 | 933 | 957 | P9 |
| A10 | 9-27-211 | 3726 | 3750 | P10 |
| A11 | 9-27-246 | 3761 | 3785 | P11 |
| A12 | 17-31-298 | 5083 | 5107 | P12 |
| A13 | 17-31-413 | 5198 | 5222 | P13 |
| A14 | 17-32-24 | 10625 | 10649 | P14 |
| A15 | 99-14387-50 | 11027 | 11051 | P15 |
| A16 | 99-14387-199 | 11176 | 11200 | P16 |
| A17 | 17-33-TGAGACT | 13961 | 13985 | P17 |
| A18 | 17-34-860 | 14690 | 14714 | P18 |
| A19 | 17-34-915 | 14745 | 14769 | P19 |
| A20 | 17-35-71 | 14803 | 14827 | P20 |
| A21 | 17-35-306 | 15038 | 15062 | P21 |
| A22 | 17-36-47 | 15668 | 15692 | P22 |
| A23 | 17-36-120 | 15778 | 15802 | P23 |
| A24 | 17-37-629 | 17817 | 17841 | P24 |
| A25 | 17-37-811 | 17999 | 18023 | P25 |
| A26 | 17-38-349 | 18477 | 18501 | P26 |

Example 5

Preparation of Antibody Compositions to the 56-Glu Variant of APM1

Substantially pure protein or polypeptide is isolated from transfected or transformed cells containing an expression vector encoding the APM1 protein or a portion thereof. The concentration of protein in the final preparation is adjusted, for example, by concentration on an Amicon filter device, to the level of a few micrograms/mL. Monoclonal or polyclonal antibody to the protein can then be prepared as follows:

A. Monoclonal Antibody Production by Hybridoma Fusion

Monoclonal antibody to epitopes in the APM1 protein or a portion thereof can be prepared from murine hybridomas according to the classical method of Kohler, G. and Milstein, C., Nature 256:495 (1975) or derivative methods thereof. Also see Harlow, E., and D. Lane. 1988. Antibodies A Laboratory Manual. Cold Spring Harbor Laboratory. pp. 53–242.

Briefly, a mouse is repetitively inoculated with a few micrograms of the APM1 protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2.

B. Polyclonal Antibody Production by Immunization

Polyclonal antiserum containing antibodies to heterogeneous epitopes in the APM1 protein or a portion thereof can be prepared by immunizing suitable non-human animal with the APM1 protein or a portion thereof, which can be unmodified or modified to enhance immunogenicity. A suitable non-human animal is preferably a non-human mammal is selected, usually a mouse, rat, rabbit, goat, or horse. Alternatively, a crude preparation which has been enriched for APM1 concentration can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, J. et al. J. Clin. Endocrinol. Metab. 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either the monoclonal or the polyclonal protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Example 6

Association between Apm1 Markers and Characteristics in an Obese Population Materials and Methods Patients Subjects of this study were unrelated and lived in the region of Paris. Obese girls were severely obese since early childhood and exceeded the 98$^{th}$ percentile of normal growth curves. Blood sampling and testing of these subjects were performed prior to any weight reduction treatment. At the time of admission, weights and heights were recorded, blood samples were collected, the buffy coat was isolated for DNA preparation and the plasma was separated for biochemical analysis. A summary of their biochemical characteristics is listed in Table 5. In this first study, genotype analysis was performed for markers 9-27/261, 99-14387/129, 9-12/124, 99-14405/105, and 9-16/189.

TABLE 5

Characteristics of Obese Adolescent Girls used in Study 1

| Parameter | Value |
|---|---|
| n | 159 |
| | Mean ± SEM |
| Age (yrs) | 12.1 ± 0.3 |
| Body mass index (kg/m$^2$) | 30.5 ± 0.5 |
| Cholesterol (mg/dl) | 172 ± 3.0 |
| FFA (mM) | 0.612 ± 0.022 |
| Glucose (mg/dl) | 76.3 ± 0.81 |
| Insulin ($\mu$U/ml) | 16.4 ± 0.67 |
| Leptin (ng/ml) | 35.7 ± 1.57 |

A second group of both obese girls and boys was also used to confirm some results of the first study (Table 6). Genotype analysis was performed for markers 9-12/48, 9-12/124, 9-12/355, 99-14405/105, and 9-16/189.

All parents of obese children provided informed consent for biological testing and the use of DNA for genetic analysis. The study protocol was approved by the *Comité Consultatif de Protection des Personnes Participants à la Recherche Clinique*.

TABLE 6

Characteristics of Obese Adolescent Boys and Girls used in Study 2

| Parameter | Value |
|---|---|
| n | 155 |
| Boys | 55 |
| Girls | 100 |
| | Mean ± SEM |
| Age (yrs) | 12.0 ± 0.3 |
| Body mass index (kg/m$^2$) | 29.2 ± 0.5 |
| Cholesterol (mg/dl) | 171 ± 0.02 |
| FFA (mM) | 0.592 ± 0.021 |
| Glucose (mg/dl) | 74.5 ± 0.59 |

TABLE 6-continued

Characteristics of Obese Adolescent Boys and Girls used in Study 2

| Parameter | Value |
| --- | --- |
| n | 155 |
| Boys | 55 |
| Girls | 100 |
| Insulin (μU/ml) | 14.8 ± 0.72 |
| Leptin (ng/ml) | 31.2 ± 1.62 |

DNA Extraction

Blood samples were centrifuged 20 min at 913×g. The middle leukocyte layer was removed and washed twice in large volumes of 10 mM Tris HCl, pH 7.6 containing 5 mM $MgCl_2$ and 10 mM NaCl. To the cell pellet was added 3 ml of 10 mM Tris HCl, pH 7.6 containing 1 mM EDTA and 0.4 mM NaCl, 200 μl 10% (w/v) SDS, and 500 μl proteinase K (Sigma, St. Louis, Mo.; 1 mg/ml). Tubes were placed in a shaking water bath at 42° C. for 5 h. Tubes were then chilled on ice for 10 min. To precipitate proteins, 1 ml of 5 M NaCl was added and the precipitates were pelleted, and the supernatant removed. To precipitate the DNA, isopropanol (5 ml) was added, followed by recentrifugation at 3210×g for 20 min. The supernatant was discarded and 5 ml of 70% ethanol was added to the DNA pellet. After incubating 6 h or overnight at 4° C., the samples were spun at 2800×g for 5 min. The supernatant was poured off and discarded, and the pellet left to air dry. Once dry, 1.5 ml 10 mM Tris HCl containing 10 mM EDTA was added and incubated at room temperature on a rocker platform to rehydrate the DNA. DNA concentration was measured and the DNA was stored at −20° C.

Single Nucleotide Polymorphism (SNP) Identification

Amplicons investigated covered the APM1 gene. Random markers were generated from amplicons derived from BAC sequence positioned in the indicated genomic regions (Table 7). The PCR primers were then used to amplify the corresponding genomic sequence in a pool of DNA from 100 unrelated individuals (blood donors of French origin). PCR reactions (25 ml) contained 2 ng/μl pooled DNA, 2 mM $MgCl_2$, 200 μM of each dNTP, 2.9 ng/μl each primer, 0.05 unit/μl Ampli Taq Gold DNA polymerase (Perkin Elmer, Foster City, Calif.) and 1×PCR buffer (10 mM Tris HCl pH 8.3, 50 mM KCl). Amplification reactions were performed in a PTC200 MJ Research Thermocycler, with initial denaturation at 95° C. for 30 sec, annealing at 54° C. for 1 min, and extension at 72° C. for 30 sec. After cycling, a final elongation step was performed at 72° C. for 10 min. Amplification products from pooled DNA samples were sequenced on both strands by fluorescent automated sequencing on ABI 377 sequences (Perkin Elmer), using a dye-primer cycle analysis and DNA sequence extraction with ABI Prism DNA sequencing Analysis software. Sequence data analysis was automatically processed with AnaPolys (Genset, Paris, France), a software designed to detect the presence of SNPs among pooled amplified fragments. The polymorphism search is based on the presence of superimposed peaks in the electrophoresis pattern from both strands, resulting from two bases occurring at the same position. The detection limit for the frequency of SNPs detected by microsequencing pools of 100 individuals is about 10% for the minor allele, as verified by sequencing pool of known allelic frequencies. However, more than 90% of the SNPs detected by the pooling method have a frequency for minor allele higher than 20%.

TABLE 7

Characteristics of Random SNPs*

| Random SNPs | Chromosomal Localization | Allelic variation | Allele Frequency (%) | Hardy-Weinberg Equilibrium $x^2$ |
| --- | --- | --- | --- | --- |
| A | 7p12–p14 | T → C | 65 | 0.252 |
| B | 13q22 | T → C | 74 | 1.194 |
| C | 14q24.1 | A → G | 54 | 0.027 |
| D | 14q31 | T → C | 62 | 0.322 |
| E | 14q31 | G → C | 64 | 0.092 |
| F | 14q22–q23 | T → A | 79 | 0.594 |
| G | 16q22–q24 | G → A | 54 | 1.166 |
| H | 16q24 | A → G | 62 | 0.656 |
| I | 18p11–p31 | A → G | 51 | 0.319 |
| J | 21q22.8 | A → G | 56 | 0.054 |
| K | 21q22 | C → T | 59 | 1.475 |
| L | 21q22.3 | A → G | 70 | 2.070 |
| M | 21q22.3 | T → C | 60 | 1.709 |
| N | 21q22.1 | A → G | 56 | 1.060 |

*SNPS were identified using a pool of 100 DNA clones, as described in the Experimental Procedures.
The allele frequency and Hardy-Weinberg equilibrium were measured for each marker.

Genotyping

Genotyping of individual DNA samples was performed using microsequencing procedure as follows. Amplification products containing the SNPs were obtained by performing PCR reactions similar as those described for SNP identification. After purification of the amplification products, the microsequencing reaction mixture was prepared by adding in a 20 μl final volume: 10 pmol microsequencing primer (which hybridize just upstream of the polymorphic base), 1 U of Thermosequenase (Amersham Pharmacia Biotech, Piscataway, N.J.) or TaqFS (Perkin Elmer) and the 2 appropriate fluorescent ddNTPs (Perkin Elmer, Dye Terminator Set) complementary to the nucleotides at the polymorphic site of each SNP tested. After 4 minutes at 94° C.; 20 microsequencing cycles of 15 sec at 55° C., 5 sec at 72° C., and 10 sec at 94° C. were carried out in a GeneAmp PCR System 9700 (PE Applied Biosystem). After reaction, the 3'-extended primers were precipitated to remove the unincorporate fluorescent ddNTPs and analysed by electrophoresis on ABI 377 sequencers. Following gel analysis with GENESCAN software (Perkin Elmer), data were automatically processed with AnaMIS (Genset). Genotype data were compiled and checked for scoring accuracy with 32 duplicate samples.

Biochemical Analysis

Plasma biological parameters were determined using commercially available kits and following manufacturer instructions: (triglycerides, total cholesterol, and glucose: Roche Molecular Biochemicals; FFA: Wako Chemical, Neuss, Germany; leptin and insulin: RIA from Linco, St. Charles, Mo.).

Statistical Analysis

Allelic frequencies and $\chi 2$ test of Hardy Weinberg proportions were performed as data were collected (1–3). ANOVA was used for comparison of difference in time series. Two tailed t-test was used to compare the difference at each time point and $\chi 2$ analysis was used for comparison of proportions.

Results

In this example, we refer to 9-27/261 as SNP1, 99-14387/129 as SNP#2, 9-12/124 as SNP#3, 99-14405/105 as SNP#4, and 9-16/189 as SNP#5. The approximate location of the markers on a schematic (not to scale) drawing of the genomic structure of the Apm1 gene is provided in FIG. 1.

The exact location of the markers in the genomic sequence of Apm1 is given in the sequence listing and in Tables 1–4.

The effect of Apm1 polymorphisms on plasma lipid values in obese adolescent girls was examined by separating the study population into 2 groups based on their mean lipid value: one group with values above the mean, and the second group with values below the mean. The genotype frequencies of the two sample groups were then measured and analyzed for statistical significance using the $\chi 2$ test for each lipid parameter. Similar analyses were performed for 14 random markers generated, where the mean and 99.99% confidence interval are indicated as a solid and dotted line, respectively. This served as our negative control.

Figure 2:
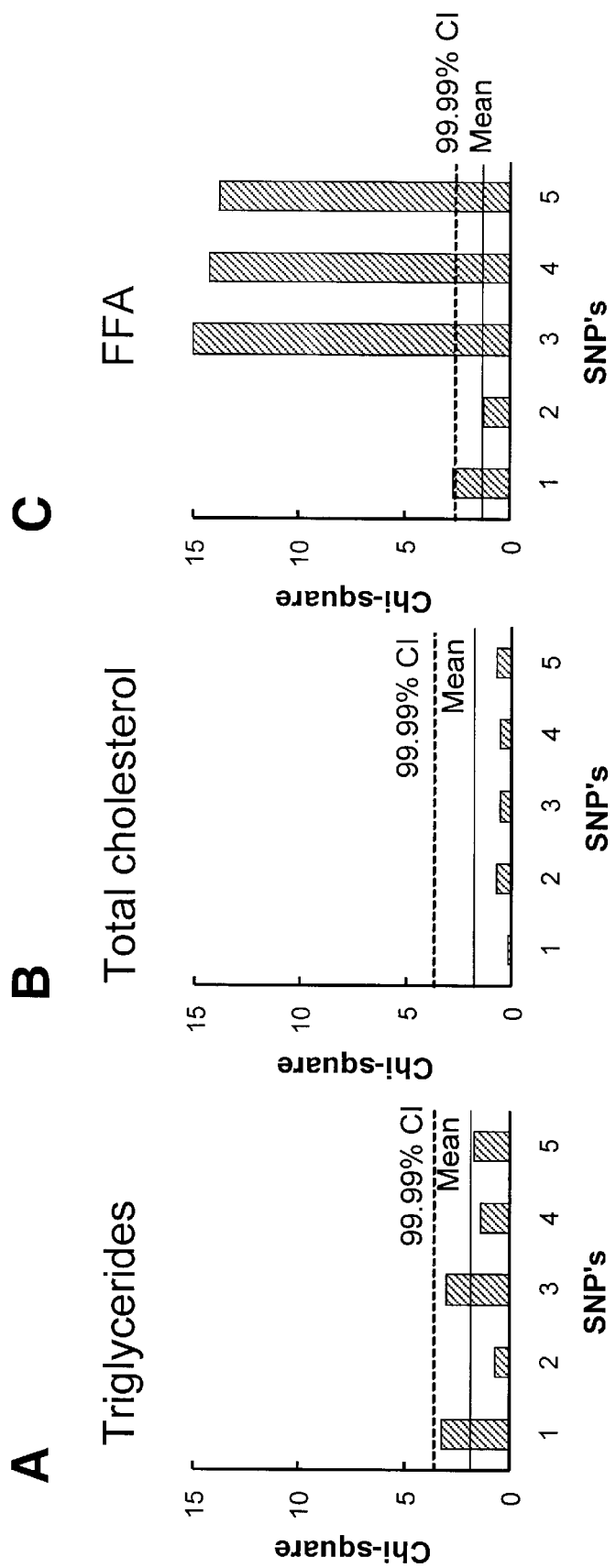
FIGS. 2A, 2B, and 2C are a graphical representation of the effect of Apm1 polymorphisms on plasma lipid values in obese adolescent girls. The mean and 99.99% confidence interval are indicated as a solid and dotted line, respectively.

The results show that the genotype frequencies for SNP# 3–5 are significantly different for obese adolescent girls with low (i.e., below the mean) or high (i.e., above the mean) free fatty acids (FFA) levels (FIG. 2). The effect of Apm1 polymorphism on FFA in obese adolescents girls was also assessed in study 1 by comparing the mean values of FFA between the homozygote populations, with the heterozygotes included with either of the homozygotes. The significance of the difference in FFA levels is shown for SNP# 4 and 5 in FIG. 4. This indicates that high FFA levels are associated with a specific genotype. The results presented in Table 8 show that the significant relationship between plasma FFA and genotype of Apm1 SNP#4 that was observed in a population of obese adolescent girls was not observed with any other parameters. The n value is reduced since all patients in which FFA were not determined were eliminated.

TABLE 8

Effect of ACRP30 SNP #4 (99-14405/105) on Clinical and Biochemical Parameters in Obese Adolescent Girls in Study 1

| Parameter | Total Population | GG | AG + AA | p-value (GG vs AG + AA) |
|---|---|---|---|---|
| n | 106 | 37 | 69 | — |
| | Mean ± SEM | | | |
| Age (yrs) | 11.3 ± 0.3 | 11.2 ± 0.4 | 11.4 ± 0.4 | NS |
| Body mass index (kg/m$^2$) | 29.5 ± 0.5 | 29.4 ± 0.7 | 29.6 ± 0.7 | NS |
| Leptin (ng/ml) | 34.2 ± 1.5 | 33.9 ± 2.6 | 34.4 ± 1.8 | NS |
| Insulin ($\mu$U/ml) | 16.9 ± 0.8 | 17.0 ± 1.1 | 16.8 ± 1.1 | NS |
| Glucose (mg/dl) | 74.6 ± 0.6 | 74.7 ± 1.1 | 74.6 ± 0.8 | NS |
| Triglycerides (mg/dl) | 106.7 ± 5.4 | 96.8 ± 6.4 | 112.0 ± 7.5 | NS |
| Cholesterol (mg/dl) | 172.0 ± 3.6 | 165.3 ± 4.3 | 176.5 ± 5.0 | NS |
| FFA (mM) | 0.612 ± 0.022 | 0.525 ± 0.031 | 0.659 ± 0.029 | 0.0037 |

The comparison of genotype and biochemical characteristics of the study 2 population (mixture of boys and girls) is shown in Table 9. As in Table 8, the FFA are significantly different in the 2 sample groups (AG+AA versus GG). As for Table 8, only those patients with data on FFA were kept in this analysis.

Figure 5:
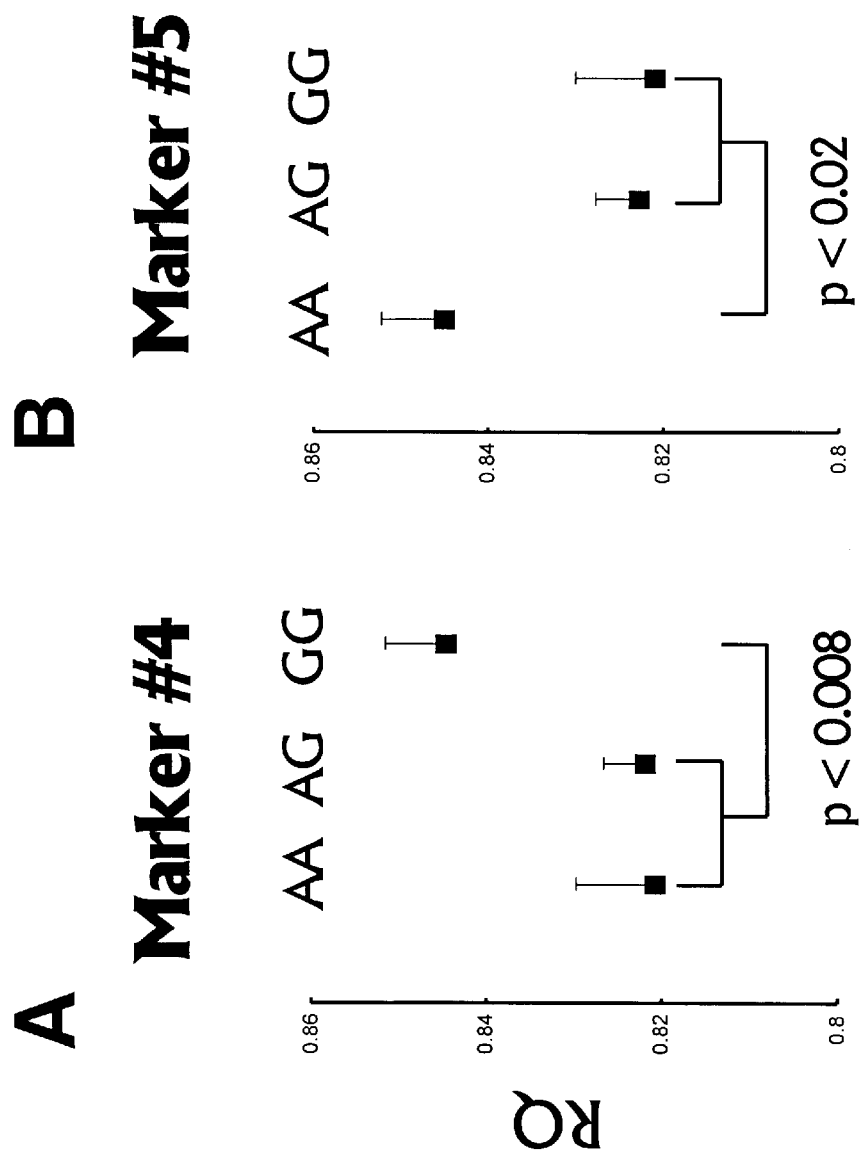
FIGS. 5A and 5B are a graphical representation of the effect of APM1 polymorphism on respiratory quotient in obese adolescents.

The effect of APM1 polymorphism on respiratory quotient in obese adolescents was determined in study 2, where the respiratory quotient was measured and compared to the genotype profile of the SNP#4 and 5, as in FIG. 4. A low respiratory quotient is associated with the same genotype that indicates a high FFA level, and vice versa (FIG. 5). This is true for both markers #4 and 5. These results are also shown in Table 9.

TABLE 9

Effect of ACRP30 SNP 99-14405/105 on Clinical and Biochemical Parameters in Obese Adolescent Boys and Girls

| Parameter | Total Population | GG | AG + AA | p-value (GG vs AG + AA) |
|---|---|---|---|---|
| n | 97 | 37 | 60 | — |
| Boys | 32 | 13 | 19 | — |
| Girls | 65 | 24 | 41 | — |
| | Mean ± SEM | | | |
| Age (yrs) | 11.4 ± 0.3 | 11.1 ± 0.5 | 11.5 ± 0.4 | NS |
| Body mass index (kg/m$^2$) | 29.7 ± 0.6 | 29.4 ± 0.8 | 29.9 ± 0.8 | NS |
| Leptin (ng/ml) | 31.3 ± 1.5 | 29.1 ± 2.6 | 32.6 ± 1.9 | NS |
| Insulin ($\mu$U/ml) | 16.2 ± 0.8 | 15.5 ± 0.9 | 16.6 ± 1.4 | NS |
| Glucose (mg/dl) | 74.9 ± 0.6 | 75.1 ± 1.0 | 74.8 ± 0.8 | NS |
| Triglycerides (mg/dl) | 110.5 ± 0.1 | 106.7 ± 0.1 | 112.7 ± 0.1 | NS |
| Cholesterol (mg/dl) | 167.7 ± 0.03 | 163.5 ± 0.04 | 170.5 ± 0.03 | NS |
| FFA (mM) | 0.599 ± 0.021 | 0.545 ± 0.033 | 0.633 ± 0.027 | 0.046 |
| Respiratory quotient | 0.834 ± 0.005 | 0.848 ± 0.009 | 0.826 ± 0.005 | 0.026 |

The effect of Apm1 polymorphisms on the leptin/BMI relationship in obese adolescent girls was also tested using a similar analysis as for the lipid values reported in FIG. 2, but using leptin/BMI ratio as the parameter. FIG. 3A shows the significant correlation between leptin levels and BMI; this has previously been reported. FIG. 3B shows a significant difference in genotype frequencies for SNP # 1–2.

Figure 6:
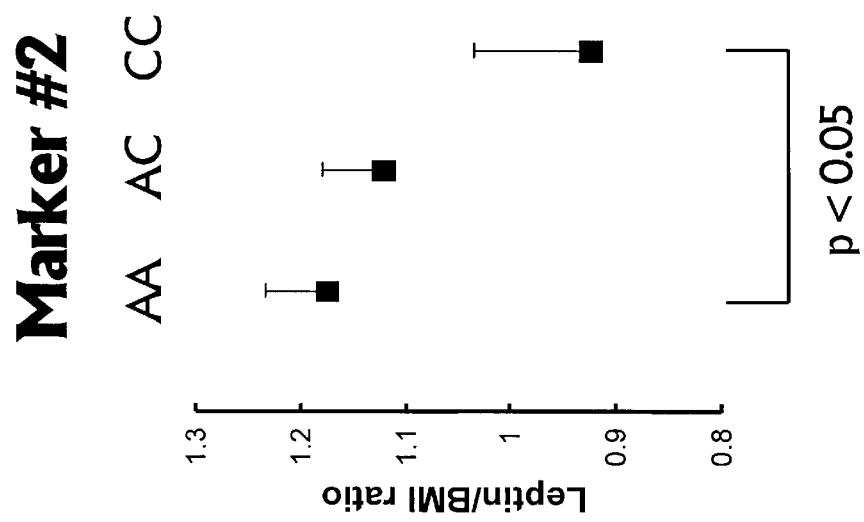
FIG. 6 is a graphical representation of the effect of APM1 on leptin/BMI ratio in obese adolescents girls.

The effect of Apm1 on leptin/BMI ratio in obese adolescents girls was further analyzed using a similar analysis as that described for FIG. 5 using leptin/BMI ratios calculated from those values measured in study 1. The results indicate a significant difference in leptin/BMI ratio between the 2 homozygote populations (FIG. 6). There was a less significant difference (p=0.07), if the heterozygote population was added to the AA population. This increased the n value significantly versus the CC population, and hence, reduced the power of the test. We would expect that with a bigger population size, this may become significant.

Figure 7:
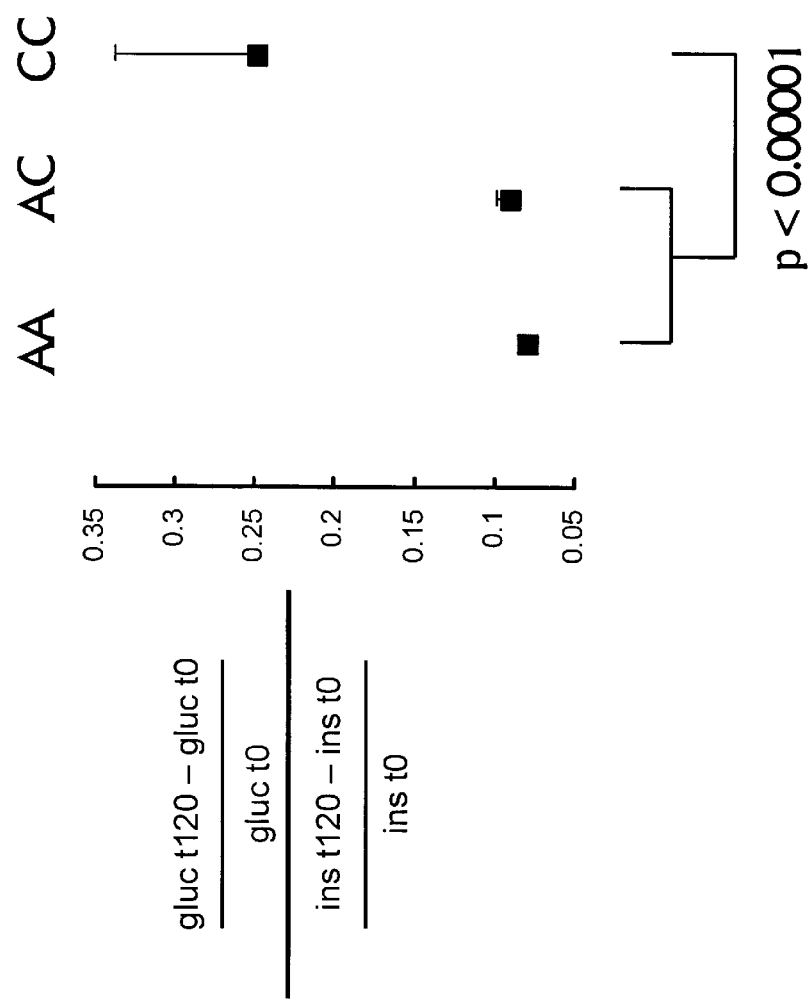
FIG. 7 is a graphical representation of the effect of APM1 polymorphism on glucose tolerance in obese adolescent girls.

The effect of Apm1 polymorphism on glucose tolerance in obese adolescent girls was also determined. The difference in glucose tolerance, calculated as shown on the y-axis, was highly significant between the two homozygote populations of SNP#2 in obese adolescent girls (FIG. 7).

Figure 8:
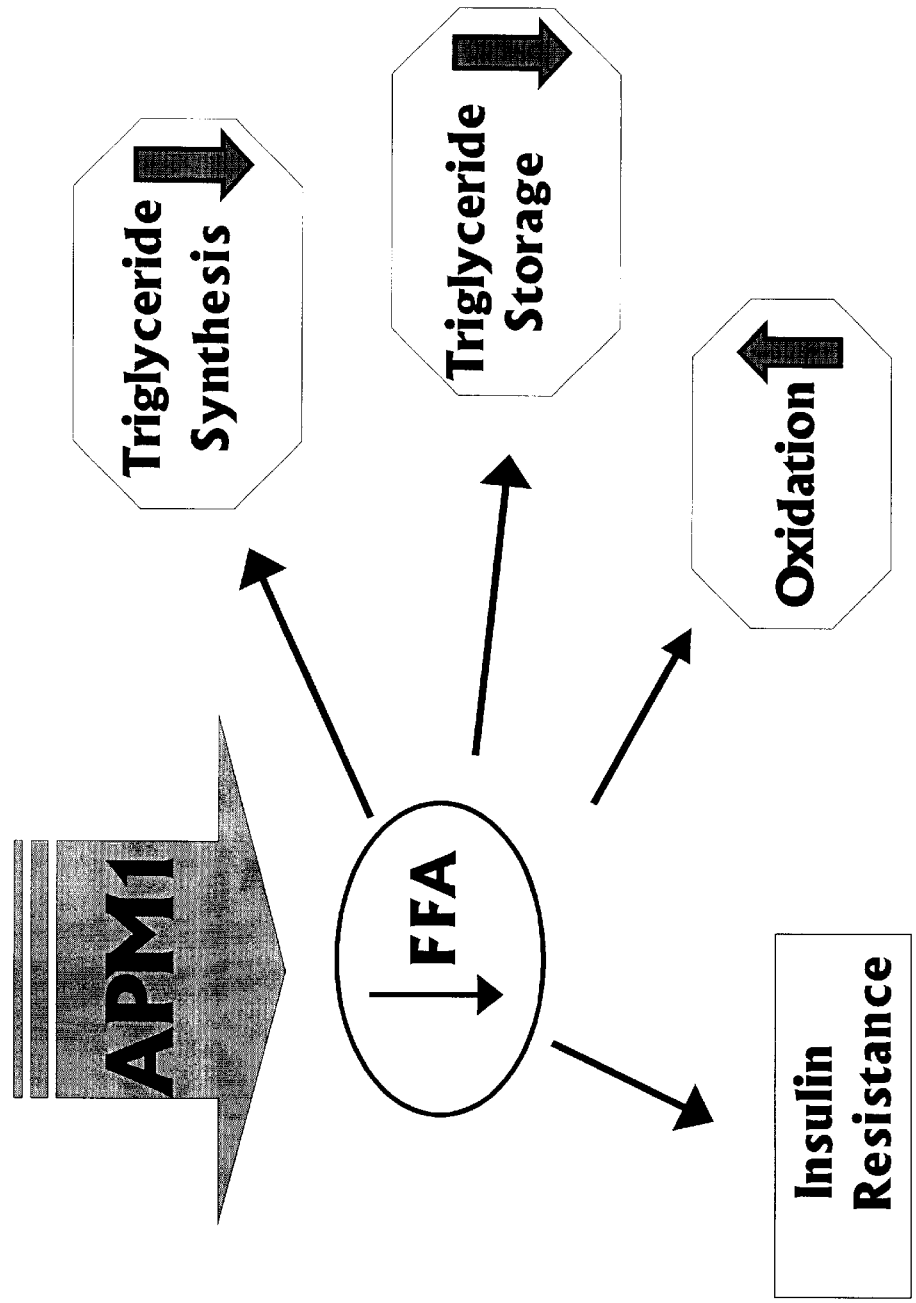
FIG. 8 shows Apm1 function predicted from polymorphism and in vivo analysis.

Apm1 function was predicted from polymorphism and in vivo analysis (FIG. 8). Based on the analysis of the polymorphisms, we would expect that this protein is directly implicated in the regulation of FFA metabolism. In vivo studies indicate that an active form of APM1 does decrease FFA in the circulation. The parallel decrease of plasma triglycerides suggests that the FFA are not being converted to triglycerides, but rather oxidized. The correlation of FFA concentrations with insulin resistance would suggest that insulin resistance would be decreased with lower circulating FFA. This, in turn, would create an environment more responsive to insulin, and hence, improve glucose tolerance.

Overall, these results demonstrate the utility of APM1 markers in assays for detecting a patient's ability or inability to oxidize FFA, particularly those derived from dietary lipid. This inability to oxidize FFA would contribute to increased accumulation of FFA in storage by the adipose tissue, which would lead to the eventual development of obesity.

The presence of FFA is also directly related to insulin resistance. Therefore this would also reflect a patient's ability to manage high levels of glucose, and his/her susceptibility towards the development of type II diabetes.

While preferred embodiments of the invention have been illustrated and described, it will be appreciated that various changes can be made therein by one skilled in the art without departing from the spirit and scope of the invention.

The following references are hereby incorporated herein by reference in their entireties.

REFERENCES

Abbondanzo S. J. et al. (1993) Methods in Enzymology, Academic Press, New York. pp. 803–823.
Ajioka R. S. et al. (1997) *Am. J. Hum. Genet.* 60:1439–1447.
Anton M. (1995) et al., *J. Virol.* 69: 4600–4606.
Araki K et al. (1995) *Proc. Natl. Acad. Sci. USA*. 92(1): 160–4.
Ausubel et al. (1989)Current Protocols in Molecular Biology, Green Publishing Associates and Wiley Interscience, N.Y.
Bates G. P. et al. (1997a) *Hum. Mol. Genet.* 6(10):633–1637.
Bates GP et al. (1997b) *Molecular Medicine today,* 508:515.
Baubonis W. (1993) *Nucleic Acids Res.* 21 (9):2025–9.
Beaucage et al. (1981) *Tetrahedron Lett.* 22:1859–1862.
Bradley A., (1987) Production and analysis of chimeric mice. In:E. J. Robertson (Ed.), Teratocarcinomas and embryonic stem cells: A practical approach. IRL Press, Oxford, pp. 113.
Brown E. L., Belagaje R., Ryan M. J., Khorana H. G. (1979) *Methods Enzymol.* 68:109–151.
Burright et al. (1997) *Brain Pathology.* 7:965–977.
Chai H. et al. (1993) *Biotechnol. Appl. Biochem.* 18:259–273.
Chee et al. (1996) *Science.* 274:610–614.
Chen et al. (1987) *Mol. Cell. Biol.* 7:2745–2752.
Chen and Kwok (1997) *Nucleic Acids Research.* 25:347–353.
Chen et al. (1997) *Proc. Natl. Acad. Sci. USA.* 94(20): 10756–10761.
Chou J. Y. (1989) *Mol. Endocrinol.* 3:1511–1514.
Clark A. G. (1990) *Mol. Biol. Evol.* 7:111–122.
Coles R., Caswell R., and Rubinsztein D. C. (1998) *Hum. Mol. Genet.* 7(5):791–800.
Compton J. (1991) *Nature.* 350(6313):91–92.
Davies S. W., Turmaine M., Cozens B. A., DiFiglia M., Sharp A. H., Ross C. A., Scherzinger E., Feldman and Steg. (1996) *Medecine/Sciences.* 12:47–55.
Dempster et al., (1977) *J. R. Stat. Soc.,* 39B: 1–38.
Dent D. S. and Latchman D. S. (1993) The DNA mobility shift assay. In: *Transcription Factors: A Practical Approach* (Latchman DS, ed:) Oxford: IRL Press. pp1–26.
Eckner R. et al.(1991) *EMBO J.* 10:3513–3522.
Excoffier L. and Slatkin M. (1995) *Mol. Biol. Evol.,* 12(5): 921–927.
Flotte et al. (1992) *Am. J. Respir. Cell Mol. Biol.* 7:349–356.
Fodor et al. (1991) *Science* 251:767–777.
Fraley et al. (1979) *Proc. Natl. Acad. Sci. USA.* 76:3348–3352.
Fried M. and Crothers D. M. (1981) *Nucleic Acids Res.* 9:6505–6525.
Fuller S. A. et al. (1996) *Immunology in Current Protocols in Molecular Biology,* Ausubel et al.Eds, John Wiley & Sons, Inc., USA.
Furth P. A. et al. (1994) *Proc. Natl. Acad. Sci USA.* 91:9302–9306.
Garner M. M. and Revzin A. (1981) *Nucleic Acids Res.*9:3047–3060.
Ghosh and Bacchawat (1991) Targeting of liposomes to hepatocytes, IN: *Liver Diseases, Targeted diagnosis and therapy using specific receptors and ligands.* Wu et al.Eds., Marcel Dekeker, New York, pp. 87–104.
Gopal (1985) *Mol. Cell. Biol.,* 5:1188–1190.
Gossen M. et al. (1992) *Proc. Natl. Acad. Sci. USA.* 89:5547–5551.
Gossen M. et al. (1995) *Science.* 268:1766–1769.
Graham et al. (1973) *Virology* 52:456–457.
Green et al. (1986) *Ann. Rev. Biochem.* 55:569–597.
Griffin et al.(1989) *Science.* 245:967–971.
Grompe, M. et al. (1989) *Proc. Natl. Acad. Sci. U.S.A.* 86:5855–5892.
Grompe, M. (1993) *Nature Genetics.* 5:111–117.
Gu H. et al. (1993) *Cell* 73:1155–1164.
Gu H. et al. (1994) *Science* 265:103–106.
Guatelli J C et al. *Proc. Natl. Acad. Sci. USA.* 35:273–286.
Gura. (1997) *Science* 275:751.
Hacia J. G., et al. (1996) *Nat. Genet.* 14(4):441–447.
Haff L. A. and Smirnov I. P. (1997) *Genonie Research,* 7:378–388.
Hames B. D. and Higgins S. J. (1985) *Nucleic Acid Hybridization: A Practical Approach.* Hames and Higgins Ed., IRL Press, Oxford.
Harju L. et al. (1993) *Clin Chem.,* 39(11 Pt 1):2282–2287.
Harland et al. (1985) *J. Cell. Biol.* 101:1094–1095.
Hawley M. E. et al. (1994) *Am. J. Phys. Anthropol* 18:104.
Hillier L. and Green P. (1991) *Methods Appl.* 1: 124–8.
Hoess et al. (1986) *Nucleic Acids Res.* 14:2287–2300.
Hu E., Liang P., and Spiegelman B. M. (1996) *J. Biol. Chem.* 271:10697–10703.
Huang L. et al. (1996) *Cancer Res* 56(5):1137–1141.
Huygen et al. (1996) *Nature Medicine.* 2(8):893–898.
Izant J. G. and Weintraub H. (1984) *Cell* 36(4):1007–1015.
Julan et al. (1992) *J. Gen. Virol.* 73:3251–3255.
Kanegae Y. et al., *Nuc. Acids Res.* 23:3816–3821.
Khoury J. et al. (1993) *Fundamentals of Genetic Epidemiology,* Oxford University Press, N.Y.
Kim U-J. et al. (1996) *Genomics* 34:213–218.
Klein et al. (1987) *Nature.* 327:70–73.
Koller et al. (1992) *Annu. Rev. Immunol.* 10:705–730.
Kopp M. U., Mello A. J., Manz A., (1998) *Science.* 280 (5366):1046–1048.
Kozal M. J. et al. (1996) *Nat. Med.* 2(7):753–759.
Landegren U. et al. (1998) *Genonie Research,* 8:769–776.
Lander and Schork (1994) *Science.* 265:2037–2048.
Lange K. (1997) *Mathematical and Statistical Methods for Genetic Analysis.* Springer, New York.
Lenhard T. et al. (1996) *Gene.* 169:187–190.
Lin M. W. et al. (1997) *Hum. Genet.* 99(3): 417–420.
Linton M. F. et al. (1993) *J. Clin. Invest.* 92:3029–3037
Liu Z. et al. (1994) *Proc. Natl. Acad. Sci. USA.* 91: 4528–4262.
Livak K. J. and Hainer J. W. (1994) *Hum. Mutat.* 3(4): 379–385.
Lockhart et al. (1996) *Nature Biotechnology* 14:1675–1680.

Mackey K., Steinkamp A., and Chomczynski P. (1998) *Mol Biotechmol.* 9(1):1–5.

Maeda et al. (1996) *Biochem. Biophys. Res. Comm.* 221:286–289

Mangiarini L., Sathasivam K., Mahal A., Mott R., Seller M., and Bates G. P: (1997) *Nat. Genet.* 15(2):197–200.

Mansour S. L. et al. (1988) *Nature.* 336:348–352.

Manz et al. (1993) *Adv. in Chromatogr.* 33:1–66.

Marshall R. L. et al. (1994) *PCR Methods and Applications.* 4:80–84.

McCormick et al. (1994) *Genet. Anal. Tech. Appl.* 11:158–164.

McLaughlin B. A. et al. (1996) *Am. J. Hum. Genet.* 59:561–569.

Montague et al. (1997) *Nature.* 387:903.

Morton N. E. (1955) *Am. J. Hum. Genet.* 7:277–318.

Muzyczka et al. (1992) *Curr. Topics in Micro. and Immunol.* 158:97–129.

Nada S. et al. (1993) *Cell* 73:1125–1135.

Nagy A. et al. (1993) *Proc. Natl. Acad. Sci. USA.* 90: 8424–8428.

Narang S. A., Hsiung H. M. (1979) Brousseau R., *Methods Enzymol.* 68:90–98.

Neda et al. (1991) *J. Biol. Chem.* 266:14143–14146.

Newton et al. (1989) *Nucleic Acids Res.* 17:2503–2516.

Nickerson D. A. et al. (1990) *Proc. Natl. Acad. Sci. U.S.A.* 87:8923–8927.

Nicolau et al. (1982) *Biochim. Biophys. Acta.* 721:185–190.

Nyren P. et al. (1993) *Anal. Biochem.* 208(1):171–175.

O'Reilly et al. (1992) *Baculovirus Expression Vectors: A Laboratory Manual.* W. H. Freeman and Co., New York.

Olno et al. (1994) *Science.* 265:781–784.

Orita et al. (1989) *Proc. Natl. Acad. Sci. U.S.A.* 86: 2776–2770.

Ott J. (1991) *Analysis of Human Genetic Linkage.* John Hopkins University Press, Baltimore.

Pastinen et al. (1997) *Genome Research.* 7:606–614.

Pease S. and William R. S. (1990) *Exp. Cell. Res.* 190:09–211.

Perlin et al. (1994) *Am. J. Hum. Genet.* 55:777–787.

Peterson et al. (1993) *Proc. Natl. Acad. Sci. USA.* 90: 7593–7597.

Pietu et al. (1996) *Genome Research.* 6:492–503.

Potter et al. (1984) *Proc. Natl. Acad. Sci. U.S.A.* 81(22): 7161–7165.

Reid L. H. et al. (1990) *Proc. Natl. Acad. Sci. U.S.A.* 87:4299–4303.

Risch, N. and Merikangas, K. (1996) *Science.* 273:1516–1517.

Robertson E. (1987) "Embryo-Derived Stem Cell Lines." In: E. J. Robertson Ed. *Teratocarcinomas And Embryonic Stem Cells: A Practical Approach.* IRL Press, Oxford, pp. 71.

Rossi et al. (1991) *Pharmacol. Ther.* 50:245–254.

Roth J. A. et al. (1996) *Nature Medicine.* 2(9):985–991.

Rougeot, C. et al. *Eur. J. Biochem.* 219(3):765–773.

Roux et al. (1989) *Proc. Natl. Acad. Sci. U.S.A.* 86:9079–9083.

Ruano et al. (1990) *Proc. Natl. Acad. Sci. U.S.A.* 87:6296–6300.

Sambrook, J., Fritsch, E. F., and T. Maniatis. (1989) *Molecular Cloning: A Laboratory Manual.* 2ed. Cold Spring Harbor Laboratory, Cold Spring Harbor, N.Y.

Samson M, et al. (1996) *Nature,* 382(6593):722–725.

Samulski et al. (1989) *J. Virol.* 63:3822–3828.

Sanchez-Pescador R. (1988) *J. Clin. Microbiol.* 26(10): 1934–1938.

Sandou et al. (1994) *Science.* 265:1875–1878.

Sarkar, G. and Sommer S. S. (1991) *Biotechniques.*

Sauer B. et al. (1988) *Proc. Natl. Acad Sci. U.S.A.* 85:5166–5170.

Schaid D. J. et al. (1996) *Genet. Epidemiol.* 13:423–450.

Schedi A. et al. (1993a) *Nature.* 362:258–261.

Schedi et al. (1 993b) *Nucleic Acids Res.* 21:4783–4787.

Schena et al. (1995) *Science.* 270:467–470.

Schena et al. (1996) *Proc. Natl. Acad. Sci. U.S.A.* 93(20): 10614–10619.

Schneider et al.(1997) *Arlequin: A Software For Population Genetics Data Analysis.* University of Geneva.

Sczakiel G. et al. (1995) *Trends Microbiol.* 3(6):213–217.

Shay J. W. et al. (1991) *Biochem. Biophys. Acta.* 1072:1–7.

Sheffield, V. C. et al. (1991) *Proc. Natl. Acad. Sci. U.S.A.* 49:699–706.

Shizuya et al. (1992) *Proc. Natl. Acad. Sci. U.S.A.* 89:8794–8797.

Shoemaker D. D. et al. (1996) *Nat. Genet.* 14:450–456.

Smith (1957) *Ann. Hum. Genet.* 21:254–276.

Smith et al. (1983) *Mol. Cell. Biol.* 3:2156–2165.

Sosnowski R. G. et al. (1997) *Proc. Natl. Acad. Sci. U.S.A.* 94:1119–1123.

Spielmann S. et al. (1993) *Am. J. Hum. Genet.* 52:506–516.

Spielmann S. and Ewens W. J. (1998) *Am. J. Hum. Genet.* 62:450–458.

Sternberg N. L. (1992) *Trends Genet.* 8:1–16.

Sternberg N. L. (1994) *Mamm. Genome.* 5:397–404.

Syvanen A. C. et al. (1994) *Clin. Chim. Acta.* 226(2): 225–236.

Tacson et al. (1996) *Nature Medicine.* 2(8):888–892.

Te Riele et al. (1990) *Nature.* 348:649–651.

Terwilliger J. D. and Ott J. (1994) *Handbook of Human Genetic Linkage.* John Hopkins University Press, London.

Thomas K. R. et al. (1986) *Cell.* 44:419–428.

Thomas K. R. et al. (1987) *Cell.* 51:503–512.

Tur-Kaspa et al. (1986) *Mol. Cell. Biol.* 6:716–718.

Tyagi et al. (1998) *Nature Biotechnology.* 16:49–53.

Urdea M. S. (1988) *Nucleic Acids Research.* 11:4937–4957.

Urdea M. S. et al.(1991) *Nucleic Acids Symp. Ser.* 24:197–200.

Van der Lugt et al. (1991) *Gene.* 105:263–267.

Vlasak R. et al. (1983) *Eur. J. Biochem.* 135:123–126.

Wabiko et al. (1986) *DNA.*5(4):305–314.

Walker et al. (1996) *Clin. Chem.* 42:9–13.

Wanker E. E., Mangiarini L., and Bates G. P. (1997) *Cell.* 90(3):537–48.

Weir, B. S. (1996) *Genetic data Analysis II: Methods for Discrete population genetic Data, Sinauer Assoc., Inc., Sunderland, Mass. U.S.A.*

White, M. B. et al. (1992) *Genomics.* 12:301–306.

White, M. B. et al. (1997) *Genomics.* 12:301–306.

Wong et al. (1980) *Gene.* 10:87–94.

Wood S. A. et al. (1993) *Proc. Natl. Acad. Sci. U.S.A.* 90:4582–4585.

Wu and Wu (1987) *J. Biol. Chem.* 262:4429–4432.

Wu and Wu (1988) *Biochemistry.* 27:887–892.

Wu et al. (1989) *Proc. Natl Acad. Sci. U.S.A.* 86:2757.

Yagi T. et al. (1990) *Proc. Natl. Acad. Sci. U.S.A.* 87:9918–9922.

Zhao et al. (1998) *Am. J. Hum. Genet.* 63:225–240.

Zou Y. R. et al. (1994) *Curr. Biol.* 4:1099–1103.

Hill, W. G. (1974) in *Heredity,* (Edinburgh), pp. 229–239.

Terwilliger, J. O. (1994) *Handbook for Humun Genetic Linkage* (John Hopkins University Press, Baltimore).

Schneider, S., Kueffer, J. M., Roessli, D., & Excofier, L. (1997) *Arlequin: A software for population genetic data analysis,* 1.1 edition (Genetics and Biometry Laboratory, Department of Anthropology, University of Geneva, Geneva).

What is claimed is:

1. A method of genotyping comprising the steps of:
   a) obtaining a biological sample; and
   b) determining the identity of a nucleotide at a biallelic marker at position 15196 of SEQ ID NO:1 or the complements thereof within said sample.

2. The method of claim 1, wherein said biological sample is obtained from a single subject.

3. The method of claim 2, wherein the identity of the nucleotides at said biallelic marker is determined for both copies of said biallelic marker present in said subject's genome.

4. The method of claim 1, wherein said biological sample is obtained from multiple subjects.

5. The method of claim 1, further comprising amplifying a portion of said sequence comprising the biallelic marker prior to said determining step.

6. The method of claim 1, wherein said determining is performed by a method selected from the group consisting of a hybridization assay, a sequencing assay, a microsequencing assay, and an allele-specific amplification assay.

* * * * *

UNITED STATES PATENT AND TRADEMARK OFFICE
CERTIFICATE OF CORRECTION

PATENT NO. : 6,582,909 B1
DATED : June 24, 2003
INVENTOR(S) : Lydie Bougueleret et al.

It is certified that error appears in the above-identified patent and that said Letters Patent is hereby corrected as shown below:

Column 29,
Line 45, "($^{32}$p," should read -- ($^{32}$P, --.

Column 68,
Line 31, "$\theta 4$=—= frequency" should read -- $\theta 4$= - - = frequency --.
Line 33, "$\theta 3$=—+= frequency" should read -- $\theta 3$= - + = frequency --.
Line 33, "$a_{i\ at\ Mi}$" should read -- $a_i$ at $M_i$ --.
Line 35, "$\theta 2$=+—= frequency" should read -- $\theta 2$= + - = frequency --.

Column 71,
Lines 30-31, "are expect similar" should read -- are expected to present similar --.

Column 77,
Line 42, "2. Regulatory Elements Promoters" should read -- 2. Regulatory Elements Promoters --.

Column 79,
Line 20, "NAotI" should read -- *Not*I --.

Column 81,
Line 42, "(Gliosh" should read -- (Ghosh --.

Column 83,
Line 34, "*typhinzuriunt*" should read -- *typhimurium* --.

Column 90,
Line 20, "PMI cDNA" should read -- *APMI* cDNA --.

Column 102,
Line 12, "Obese Population Materials" should read -- Obese Population Materials and Methods: --.

Column 109,
Line 32, "Olno et al." should read -- Ohno et al. --.

UNITED STATES PATENT AND TRADEMARK OFFICE
CERTIFICATE OF CORRECTION

PATENT NO.     : 6,582,909 B1
DATED          : June 24, 2003
INVENTOR(S)    : Lydie Bougueleret et al.

It is certified that error appears in the above-identified patent and that said Letters Patent is hereby corrected as shown below:

<u>Column 110,</u>
Line 7, "(1 993b)" should read -- (1993b) --.

Signed and Sealed this

Eleventh Day of May, 2004

JON W. DUDAS
*Acting Director of the United States Patent and Trademark Office*